United States Patent
Li

(10) Patent No.: US 11,930,694 B2
(45) Date of Patent: Mar. 12, 2024

(54) POLYMER SEMICONDUCTORS CONTAINING ACRYLYL OR ACRYLYL-LIKE SIDE CHAIN AND THEIR DEVICES

(71) Applicant: UNIVERSITY OF WATERLOO, Waterloo (CA)

(72) Inventor: Yuning Li, Kitchener (CA)

(73) Assignee: UNIVERSITY OF WATERLOO, Waterloo (CA)

( * ) Notice: Subject to any disclaimer, the term of this patent is extended or adjusted under 35 U.S.C. 154(b) by 0 days.

(21) Appl. No.: 17/342,345

(22) Filed: Jun. 8, 2021

(65) Prior Publication Data

US 2021/0384435 A1 Dec. 9, 2021

Related U.S. Application Data

(60) Provisional application No. 63/102,296, filed on Jun. 8, 2020.

(51) Int. Cl.
*H10K 85/10* (2023.01)
*C07D 333/28* (2006.01)
(Continued)

(52) U.S. Cl.
CPC ......... *H10K 85/113* (2023.02); *C07D 333/28* (2013.01); *C08G 61/126* (2013.01);
(Continued)

(58) Field of Classification Search
CPC ............. H01L 51/0036; H01L 51/0043; H01L 51/0566; H01L 51/4253; C07D 333/28;
(Continued)

(56) References Cited

U.S. PATENT DOCUMENTS

| 5,198,153 A | 3/1993 | Angelopoulos et al. |
| 5,892,244 A | 4/1999 | Tanaka et al. |

(Continued)

FOREIGN PATENT DOCUMENTS

| EP | 0 528 662 | 11/1995 |
| EP | 0 889 350 A1 | 1/1999 |

(Continued)

OTHER PUBLICATIONS

Zou et al. (Chin. J. Org. Chem. 2013, 33, 1522-1526).*
(Continued)

*Primary Examiner* — Shane Fang
(74) *Attorney, Agent, or Firm* — Bryan D. Zerhusen, Esq.; Nicholas R. Herrel, Esq.; CANTOR COLBURN LLP

(57) ABSTRACT

The present disclosure provides for the development and applications of monomeric, oligomeric and/or polymeric semiconductor materials comprising a five-membered heteroaromatic unit (e.g., thiophene; furan; selenophene; etc.) that includes an acrylyl or an acrylyl-like (—C=C—CO—) side chain. The semiconductor materials can be used as organic semiconductors for use in electronic, optical, or optoelectronic devices such as organic thin film transistors and organic photovoltaics. The disclosed semiconductor materials (e.g., semiconducting polymer compounds) can be used as high performance semiconductors (e.g., for organic solar cells or organic photovoltaics (OPVs)), and the disclosed semiconductor materials can be used for other devices (e.g., organic thin film transistors (OTFTs) and sensors, etc.).

13 Claims, 18 Drawing Sheets

(51) Int. Cl.
*C08G 61/12* (2006.01)
*H10K 10/46* (2023.01)
*H10K 30/30* (2023.01)

(52) U.S. Cl.
CPC ..... *H10K 85/151* (2023.02); *C08G 2261/124* (2013.01); *C08G 2261/1412* (2013.01); *C08G 2261/1426* (2013.01); *C08G 2261/149* (2013.01); *C08G 2261/18* (2013.01); *C08G 2261/228* (2013.01); *C08G 2261/3223* (2013.01); *C08G 2261/3243* (2013.01); *C08G 2261/91* (2013.01); *C08G 2261/92* (2013.01); *C08G 2261/94* (2013.01); *H10K 10/488* (2023.02); *H10K 30/30* (2023.02)

(58) Field of Classification Search
CPC ............ C08G 61/126; C08G 2261/124; C08G 2261/1412; C08G 2261/1426; C08G 2261/149; C08G 2261/18; C08G 2261/228; C08G 2261/3223; C08G 2261/3243; C08G 2261/91; C08G 2261/92; C08G 2261/94
See application file for complete search history.

(56) References Cited

U.S. PATENT DOCUMENTS

| | | | |
|---|---|---|---|
| 5,998,804 | A | 12/1999 | Suh et al. |
| 6,723,394 | B1 | 4/2004 | Sirringhaus et al. |
| 7,095,044 | B2 | 8/2006 | Brown et al. |
| 2003/0021913 | A1 | 1/2003 | O'Neill et al. |
| 2007/0102696 | A1 | 5/2007 | Brown et al. |
| 2008/0286566 | A1* | 11/2008 | Prakash .............. H01L 51/5036 428/690 |

FOREIGN PATENT DOCUMENTS

| | | | | |
|---|---|---|---|---|
| JP | 2011246503 | * | 12/2011 | ........... Y02E 10/542 |
| WO | WO 1996/021659 | | 7/1996 | |

OTHER PUBLICATIONS

Lee et al. (Macromol. Chem. Phys. 2010, 211, 2490-2496).*
Inganas, O., Organic Photovoltaics over Three Decades, Adv. Mater. Jun. 2018, 30, 1800388, (pp. 1 to 26).
Li, G., et al., Polymer solar cells, Feb. 2012, Nature Photon 6, 153-161 (2012).
Liu, Y., et al., Enhancing the Performance of Non-Fullerene Organic Solar Cells Using Regioregular Wide-Bandgap Polymers, Macromolecules 2018, 51, 21, 8646-8651 Publication Date: Oct. 22, 2018, https://doi.org/10.1021/acs.macromol.8b01677 Copyright @ 2018 American Chemical Society.
Lu, Luyao, et al., Recent Advances in Bulk Heterojunction Polymer Solar Cells, Chemical Reviews, Chem. Rev. Aug. 2015, 115, 12666-12731.
Park, Gl, et al., Eco-Friendly Solvent-Processed Fullerene-Free Polymer Solar Cells with over 9.7% Efficiency and Long-Term erformance Stability, Advanced Enery Materials, Adv. Energy Mater. Jun. 2017, 7, 1700566 (pp. 1-10).
Yao H, Cui., et al., 14.7% Efficiency Organic Photovoltaic Cells Enabled by Active Materials with a Large Electrostatic Potential Difference. J Am Chem Soc. May 15, 2019;141(19): 7743-7750. doi: 10.1021/jacs.8b12937. Epub May 3, 2019. PMID: 31017418.

* cited by examiner

FIGURE 11A
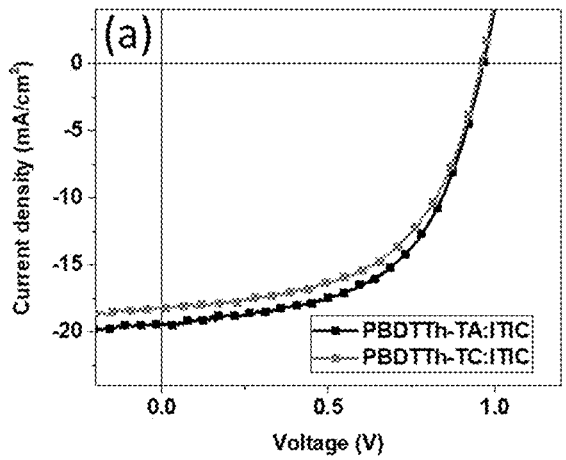
FIGURE 11B
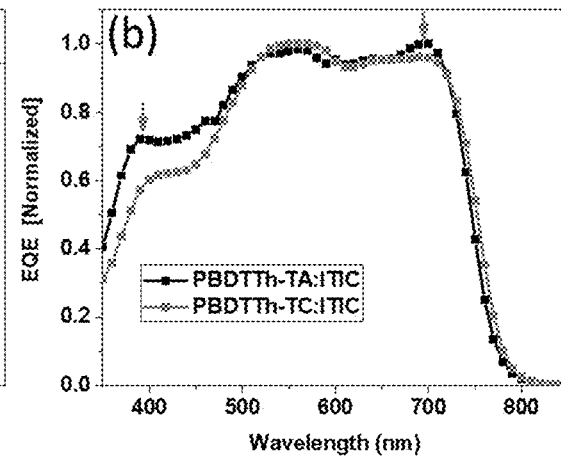
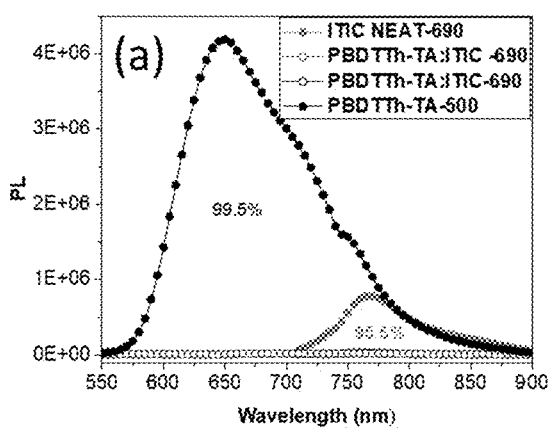
FIGURE 12A
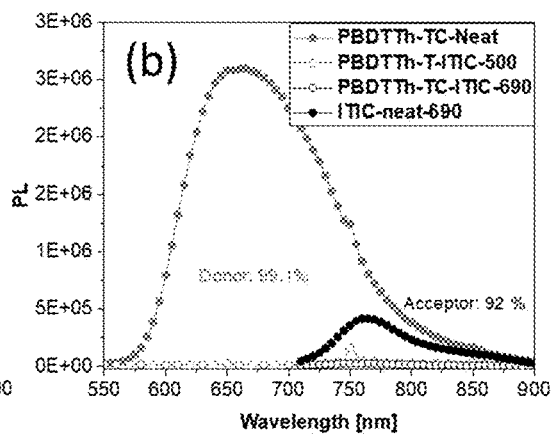
FIGURE 12B FIGURE 13A
FIGURE 13B
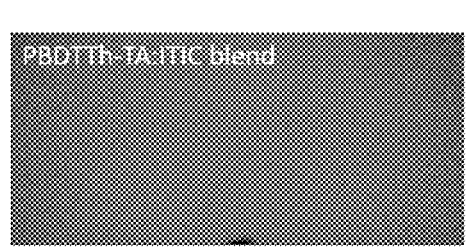
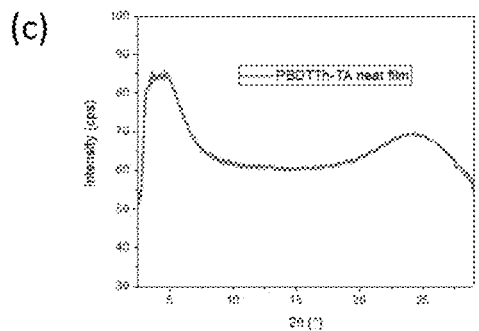
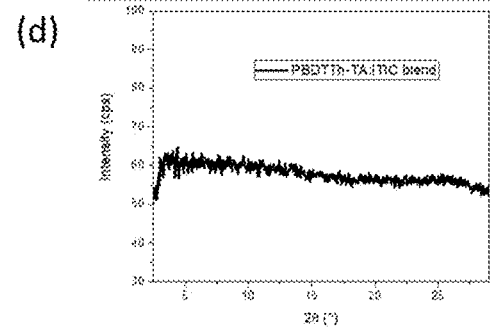
FIGURE 13C
FIGURE 13D

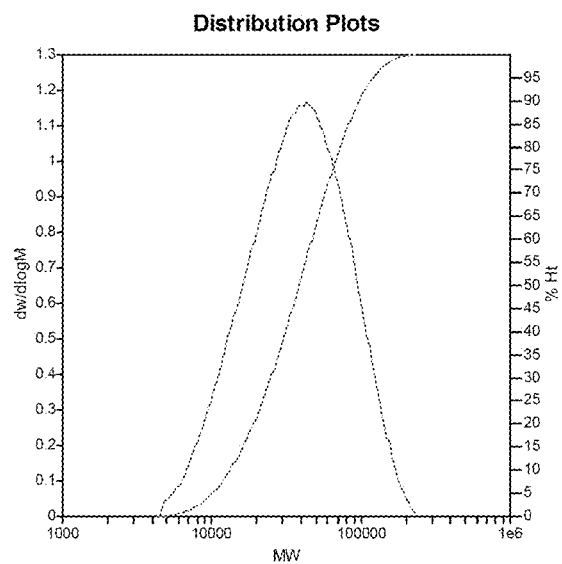 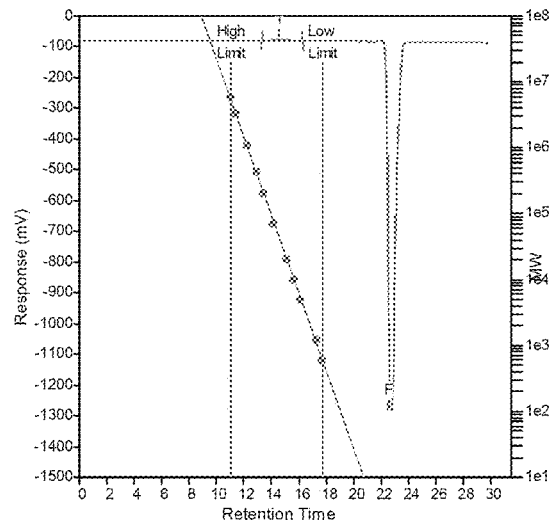
FIGURE 14A  FIGURE 14B

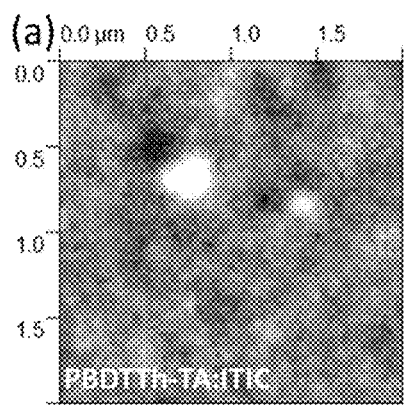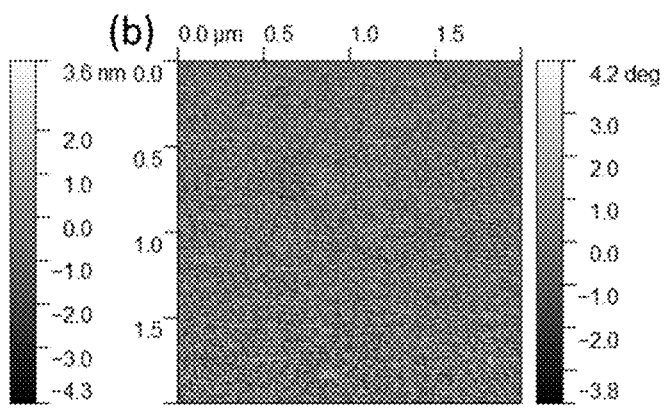
FIGURE 16A
FIGURE 16B

POLYMER SEMICONDUCTORS CONTAINING ACRYLYL OR ACRYLYL-LIKE SIDE CHAIN AND THEIR DEVICES

CROSS-REFERENCE TO RELATED APPLICATIONS

The present application claims priority benefit to U.S. Provisional Application Ser. No. 63/102,296, which was filed on Jun. 8, 2020, the entire contents of which are incorporated herein by reference in their entirety.

FIELD OF THE DISCLOSURE

The present disclosure relates to semiconductor materials and systems/methods for utilizing and fabricating the semiconductor materials and, more particularly, to monomeric, oligomeric and/or polymeric semiconductor materials having a five-membered heteroaromatic unit (e.g., thiophene; furan; selenophene; etc.) that is substituted with an acrylyl or an acrylyl-like (—C=C—CO—) side chain.

BACKGROUND

Organic electronics can be manufactured at lower costs as compared to conventional silicon-based electronics and are suitable for widespread applications including displays, radio-frequency identification (RFID) tags, chemo-/biosensors, memory devices, solar cells, photodiodes, etc. In addition, organic semiconductors can be processed at low temperatures and deposited on plastic substrates to enable light-weight, flexible, and/or ultra-thin electronic devices. For solar cell applications, in particular, the cost of the polymer donor semiconductor materials can be important for the wide spread application of polymer solar cells. Although a number of polymer donors have achieved high power conversion efficiencies (PCE) over 10%, the synthesis of those polymer donors can involve numerous steps and have high synthetic complexity (SC) (R. Po, et al., *Macromolecules,* 2015, 48: 453-461), which can result in high costs of the polymer solar cells. One polymer donor, which has a low SC, is regioregular head-to-tail poly(3-hexylthiophene) (RR-P3HT). However, RR-P3HT performs poorly when high performing small molecule acceptors, e.g., ITIC ($C_{94}H_{82}N_4O_2S_4$) and its derivatives, as well as polymer acceptors, e.g., PNDI(2OD)2T, are used (M. Zhang, et al., *Advanced Materials,* 2014, 26, 5880-5885) due to its too high HOMO (highest occupied molecular orbital) energy level and/or other incompatible properties with the ITIC derivatives. Thus, an interest exists for improved organic electronic materials (e.g., improved polymer donor semiconductor materials).

These and other inefficiencies and opportunities for improvement are addressed and/or overcome by the materials, systems, methods, assemblies and devices of the present disclosure.

SUMMARY

The present disclosure provides advantageous semiconductor materials, and improved systems and methods for utilizing and fabricating the semiconductor materials. More particularly, the present disclosure provides monomeric, oligomeric and/or polymeric semiconductor materials having a five-membered heteroaromatic unit (e.g., thiophene; furan; selenophene; etc.) that is substituted with an acrylyl or an acrylyl-like (—C=C—CO—) side chain.

The present disclosure provides for semiconducting polymer compounds comprising a five-membered heteroaromatic unit (e.g., thiophene; furan; selenophene; etc.) that is substituted with an acrylyl or acrylyl-like (—C=C—CO—) side chain. The disclosed semiconducting polymer compounds can be used as high performance polymer semiconductors (e.g., for organic solar cells or organic photovoltaics (OPVs)), and the disclosed semiconducting polymer compounds can be used for other devices (e.g., organic thin film transistors (OTFTs) and sensors, etc.).

In exemplary embodiments, the present disclosure provides polymeric semiconductor materials comprising a five-membered heteroaromatic unit that is substituted with an acrylyl or acrylyl-like (—C=C—CO—) side chain, and the polymeric semiconductor materials can be utilized for electronic devices such as, without limitation, OPVs, organic thin-film transistors (OTFTs), sensors, etc.

Another objective is to develop OPVs, OTFTs, sensors, and other electronic devices comprising the disclosed polymer semiconductors having a five-membered heteroaromatic unit that is substituted with an acrylyl or acrylyl-like (—C=C—CO—) side chain.

The present disclosure also provides for a mixture or blend comprising one or more of the disclosed polymer semiconducting compounds, and one or more compounds or polymers having semiconducting, charge transport, hole transport, electron transport, hole blocking, electron blocking, electrically conducting, photo-conducting or light emitting properties.

Further, the present disclosure provides for a formulation comprising the disclosed polymer semiconducting compound and an organic solvent.

Furthermore, the present disclosure provides for the use of the disclosed organic semiconducting compound as charge transport, semiconducting, electrically conducting, photo-conducting or light emitting material in optical, electro-optical, electronic, electroluminescent or photoluminescent components or devices.

Additionally, the present disclosure provides for charge transport, semiconducting, electrically conducting, photo-conducting or light emitting materials comprising the disclosed organic semiconducting compound.

The present disclosure also provides for a component or device comprising such polymer semiconducting compound, the component or device being selected from the group consisting of organic field effect transistors (OFET), thin film transistors (TFT), integrated circuits (IC), logic circuits, capacitors, radio frequency identification (RFID) tags, devices or components, organic light emitting diodes (OLED), organic light emitting transistors (OLET), flat panel displays, backlights of displays, organic photovoltaic devices (OPV), organic solar cells (OSC), photodiodes, laser diodes, photoconductors, organic photodetectors (OPD), electrophotographic devices, electrophotographic recording devices, organic memory devices, sensor devices, charge injection layers, charge transport layers or interlayers in polymer light emitting diodes (PLEDs), Schottky diodes, planarizing layers, antistatic films, polymer electrolyte membranes (PEM), conducting substrates, conducting patterns, electrode materials in batteries, alignment layers, biosensors, biochips, security markings, security devices, or components or devices for detecting and discriminating DNA sequences.

The present disclosure further relates to conjugated polymers comprising one or more repeating units which comprise the five-membered heteroaromatic unit (e.g., thiophene; furan; selenophene; etc.) that is substituted with an acrylyl or acrylyl-like (—C=C—CO—) side chain, and one or more groups selected from aryl and heteroaryl groups.

The present disclosure further relates to monomers comprising the five-membered heteroaromatic unit that is substituted with an acrylyl or acrylyl-like (—C=C—CO—) side chain.

The present disclosure also relates to small molecules comprising the disclosed fused-ring moiety, and one or more inert groups.

The present disclosure further relates to the use of a polymer, formulation, mixture or polymer blend of the present disclosure as charge transport, semiconducting, electrically conducting, photo-conducting or light emitting material, or in an optical, electro-optical, electronic, electroluminescent or photoluminescent device, or in a component of such a device or in an assembly comprising such a device or component.

The optical, electro-optical, electronic, electroluminescent and photoluminescent devices include, without limitation, organic field effect transistors (OFET), organic thin film transistors (OTFT), organic light emitting diodes (OLED), organic light emitting transistors (OLET), organic photovoltaic devices (OPV), organic photodetectors (OPD), organic solar cells, laser diodes, Schottky diodes, photoconductors and photodetectors.

The components of the above devices include, without limitation, charge injection layers, charge transport layers, interlayers, planarizing layers, antistatic films, polymer electrolyte membranes (PEM), conducting substrates and conducting patterns.

The assemblies comprising such devices or components include, without limitation, integrated circuits (IC), radio frequency identification (RFID) tags or security markings or security devices containing them, flat panel displays or backlights thereof, electrophotographic devices, electrophotographic recording devices, organic memory devices, sensor devices, biosensors and biochips.

Other objectives and advantages of the present disclosure will become readily apparent from the following discussion.

Any combination or permutation of embodiments is envisioned. Additional advantageous features, functions and applications of the disclosed materials, systems, methods, assemblies and devices of the present disclosure will be apparent from the description which follows, particularly when read in conjunction with the appended figures. All references listed in this disclosure are hereby incorporated by reference in their entireties.

BRIEF DESCRIPTION OF THE DRAWINGS

The following figures are exemplary embodiments wherein the like elements are numbered alike.

Features and aspects of embodiments are described below with reference to the accompanying drawings, in which elements are not necessarily depicted to scale.

Figure 1:
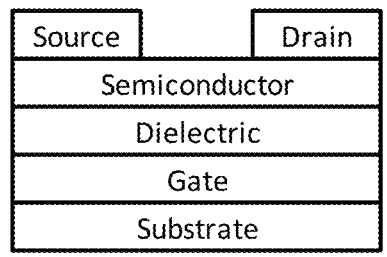

Exemplary embodiments of the present disclosure are further described with reference to the appended figures. It is to be noted that the various features, steps, and combinations of features/steps described below and illustrated in the figures can be arranged and organized differently to result in embodiments which are still within the scope of the present disclosure. To assist those of ordinary skill in the art in making and using the disclosed systems, methods and devices, reference is made to the appended figures, wherein:

FIG. 1 depicts an exemplary bottom gate/top contact organic thin film transistor (OTFT) structure.

Figure 2:
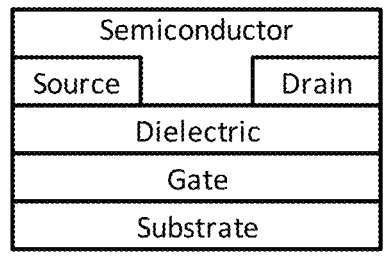

FIG. 2 depicts an exemplary bottom gate/bottom contact OTFT structure.

Figure 3:
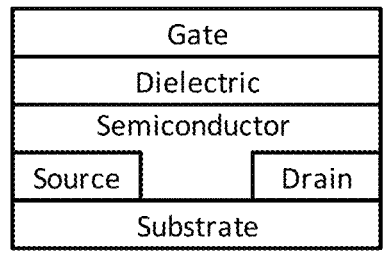

FIG. 3 depicts an exemplary top gate/bottom contact OTFT structure.

Figure 4:
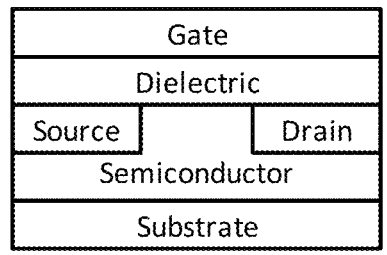

FIG. 4 depicts an exemplary top gate/top contact OTFT structure.

Figure 5:
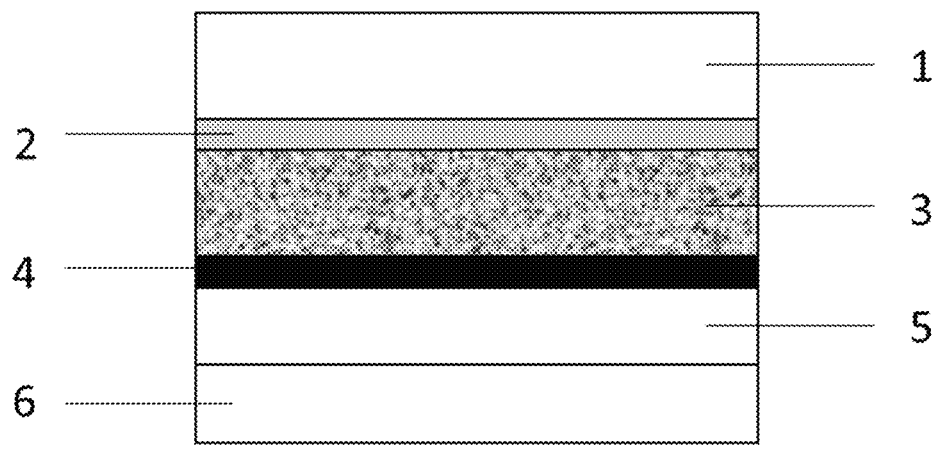

FIG. 5 depicts an exemplary organic photovoltaic device (OPV) structure where 1 is the cathode, 2 is electron transport layer, 3 is the donor-acceptor semiconductor blend layer, 4 is the hole transport layer, 5 is the transparent conductor layer, and 6 is a transparent substrate.

Figure 6:
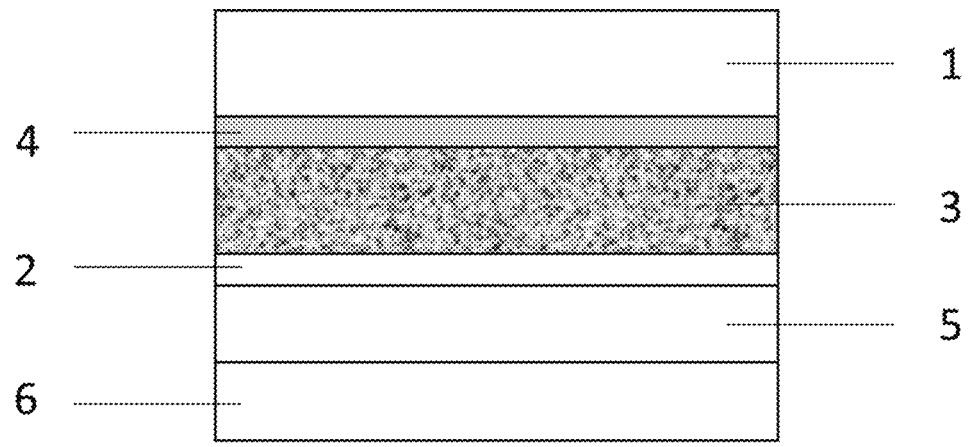

FIG. 6 depicts an exemplary inverted OPV structure where 1 is the cathode, 2 is electron transport layer, 3 is the donor-acceptor semiconductor blend layer, 4 is the hole transport layer, 5 is the transparent conductor layer, and 6 is a transparent substrate.

Figure 7:
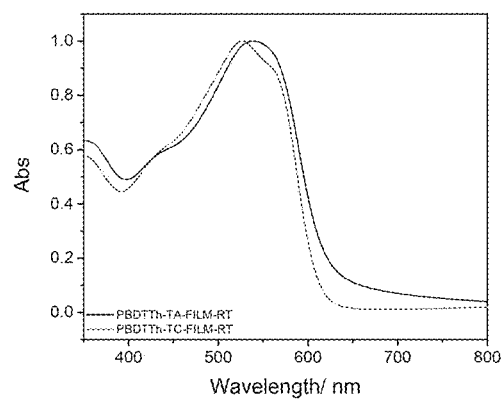

FIG. 7 shows UV-Vis spectra of PBDTTh-TA and PBDTTh-TC in the film.

Figure 8:
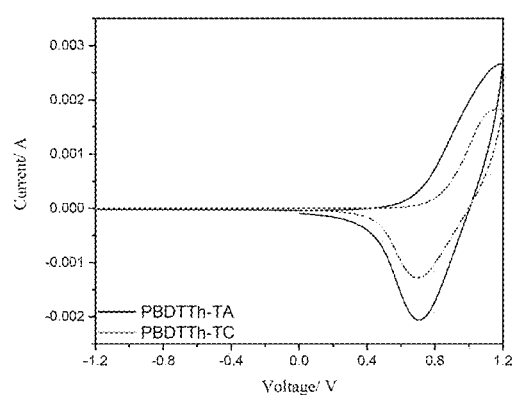

FIG. 8 shows a cyclic voltammogram of PBDTTh-TA and PBDTTh-TC.

Figure 9A:
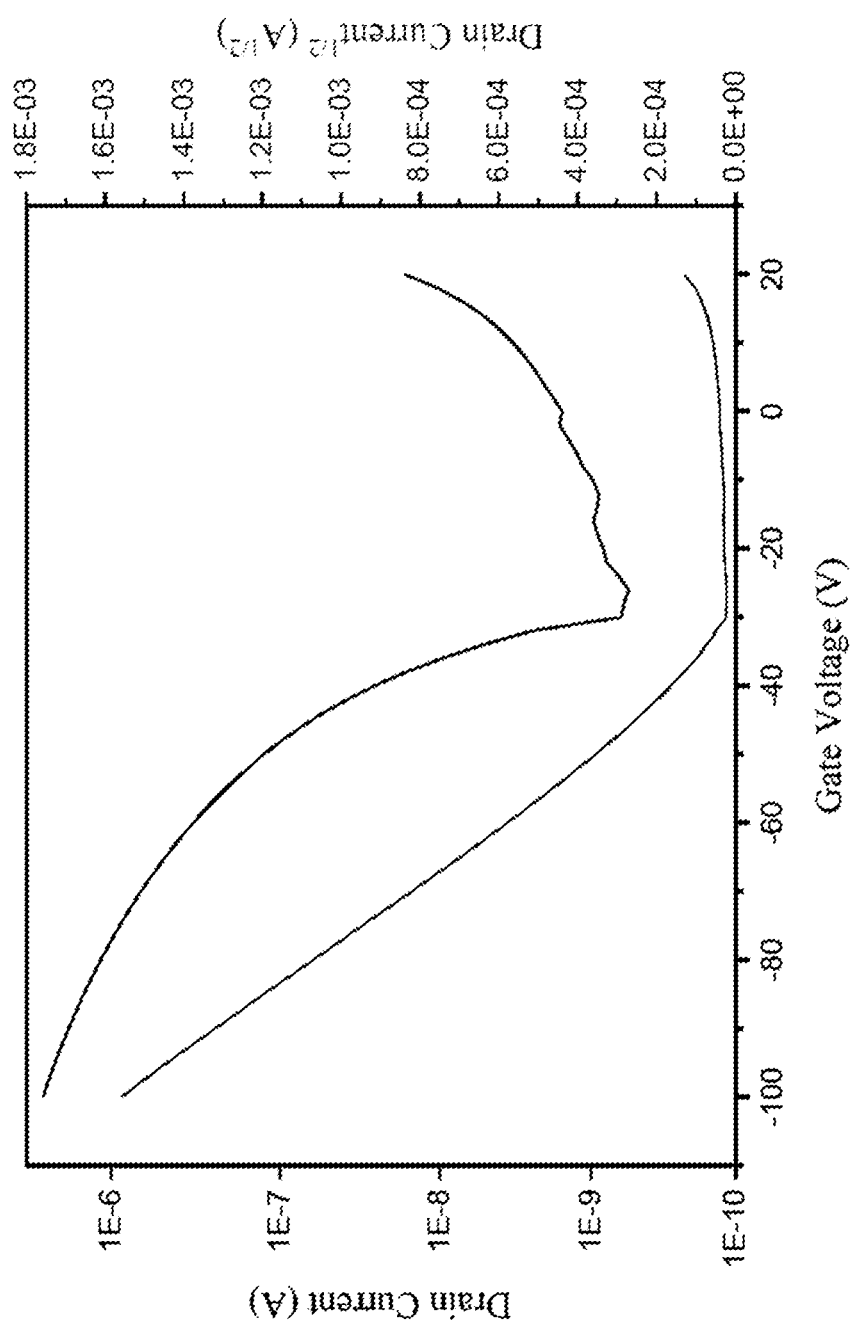
Figure 9B:
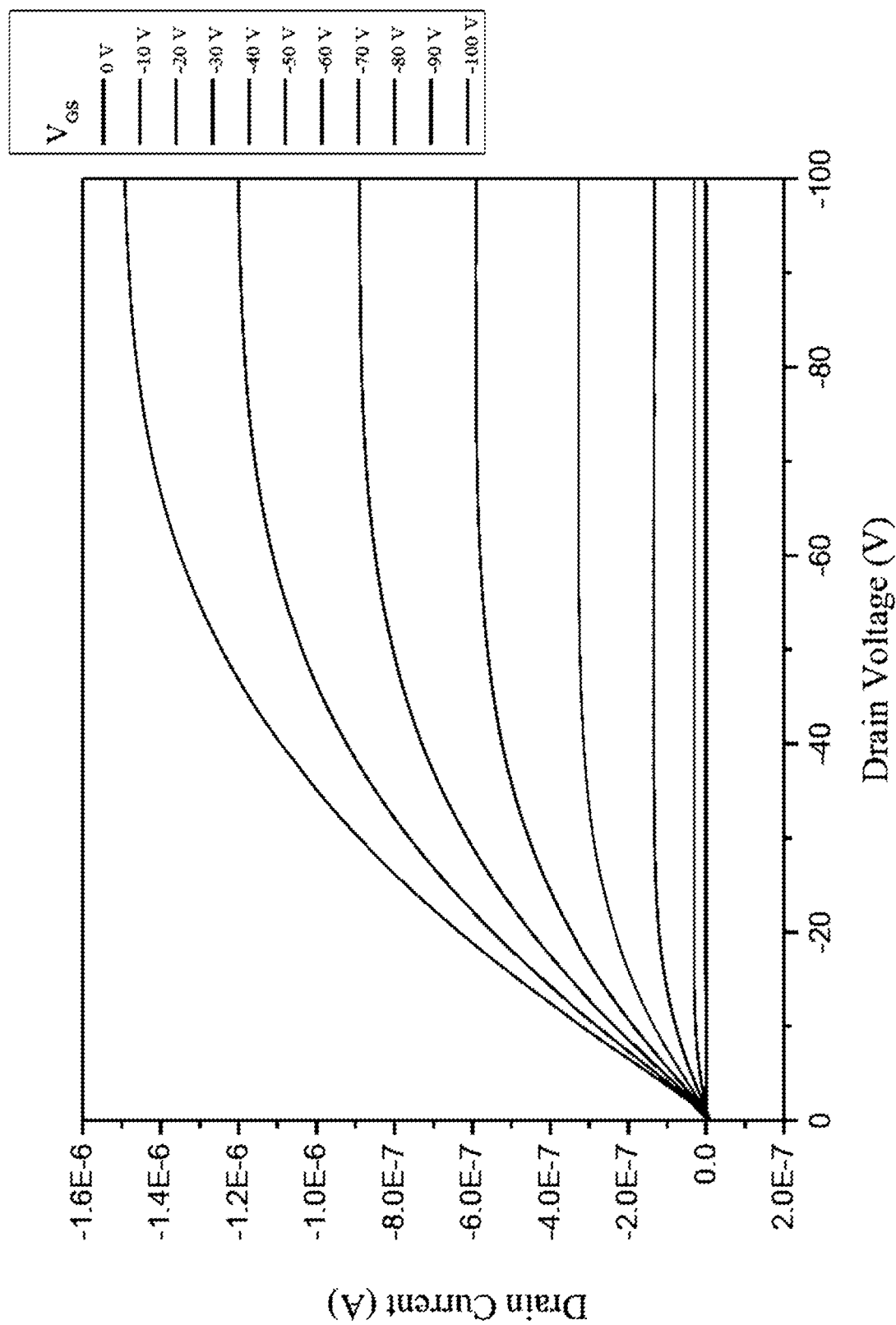

FIGS. 9A and 9B show the (FIG. 9A) power transfer and (FIG. 9B) power output characteristics of prepared OTFT devices of PBDTTh-TA.

Figure 10A:
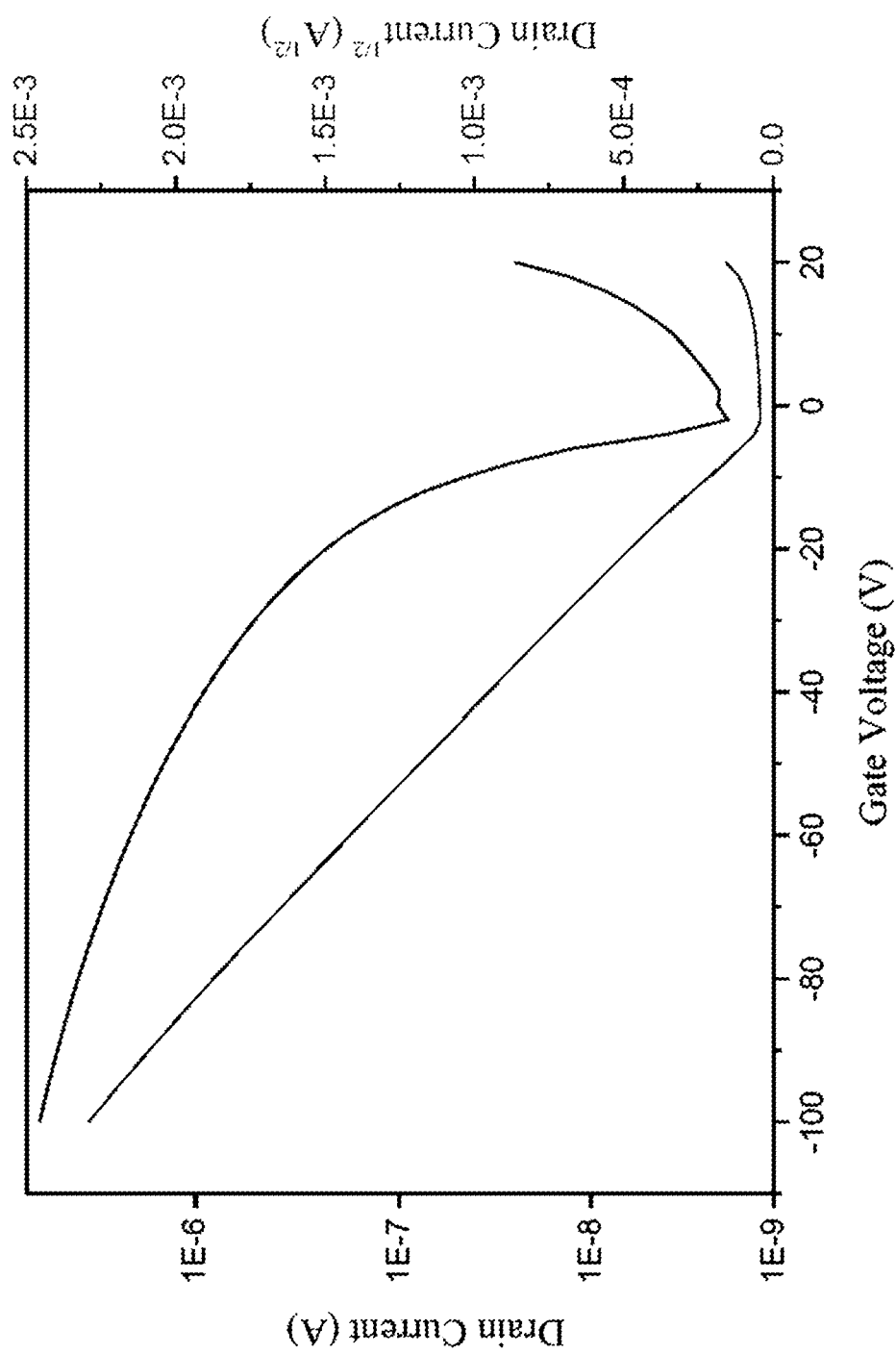
Figure 10B:
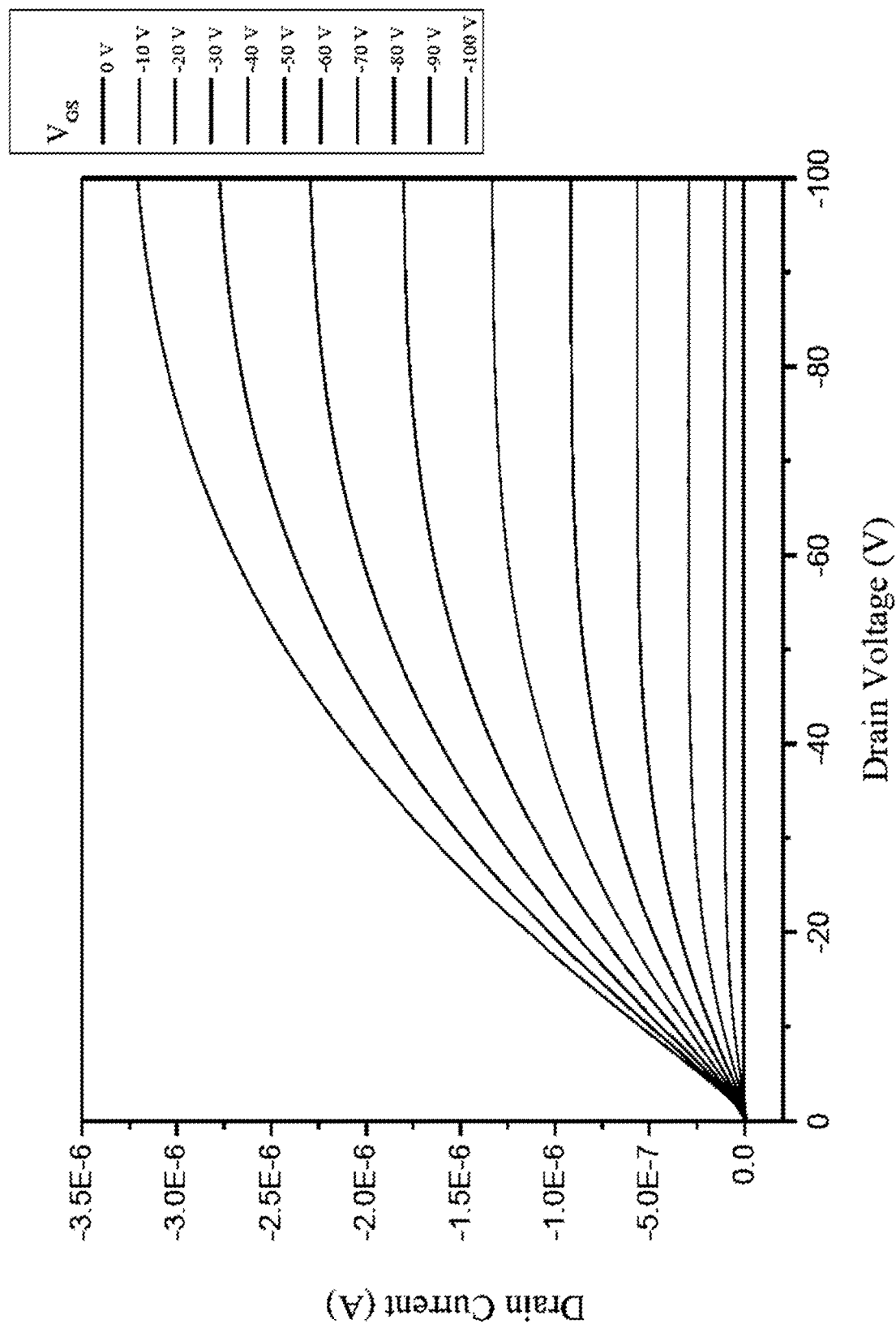

FIGS. 10A and 10B show the (FIG. 10A) power transfer and (FIG. 10B) power output characteristics of prepared OTFT devices.

FIGS. 11A and 11B show (FIG. 11A) J-V and (FIG. 11B) EQE curves of PBDTTh-TA:ITIC and PBDTTh-TA:ITIC-based devices.

FIGS. 12A and 12B show photoluminescence (PL) quenching data for PBDTTh-TA (FIG. 12A) and PBDTTh-TC (FIG. 12B) polymers for neat and blend films on glass; the excitation wavelength was 500 nm for donor and 690 nm for acceptor excitation.

FIGS. 13A-13D show grazing incidence XRD images of (FIG. 13A) neat PBDTTh-TA film on Silicon substrate; (FIG. 13B) PBDTTh-TA:ITIC blend film in device; corresponding out-of-plane line cuts are shown in (FIG. 13C) and (FIG. 13D), respectively.

FIGS. 14A-14B show HT-GPC data of polymer PBDTTh-TA.

Figures 15A, 15B:
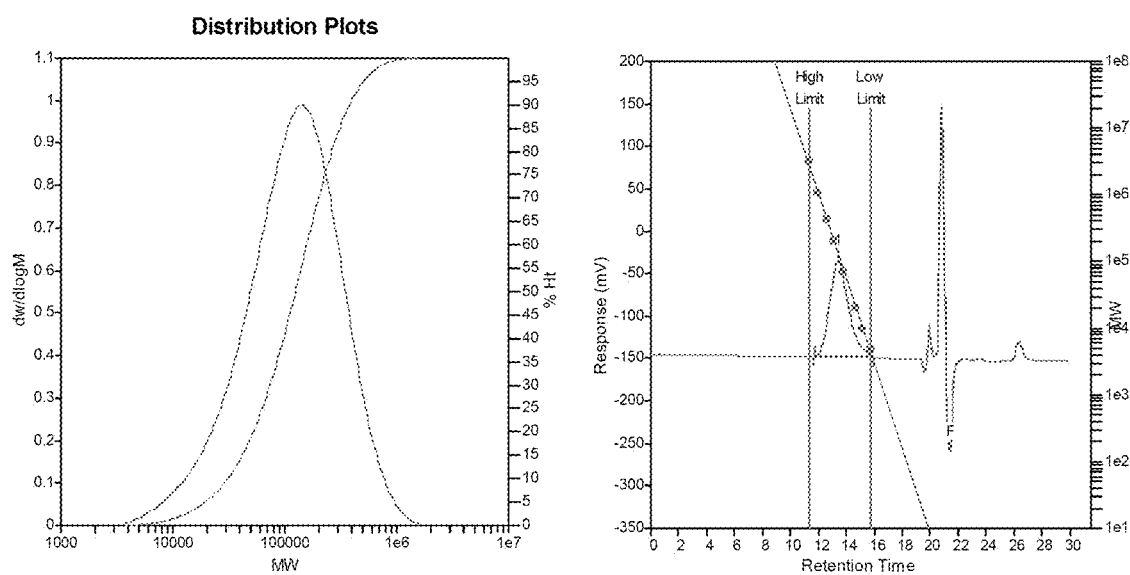

FIGS. 15A-15B show HT-GPC data of polymer PBDTTh-TC.

FIGS. 16A and 16B show AFM height (FIG. 16A) and phase image (FIG. 16B) of PBDTTh-TA:ITIC blend film; RMS roughness of the film was 1.02 nm.

Figure 17:
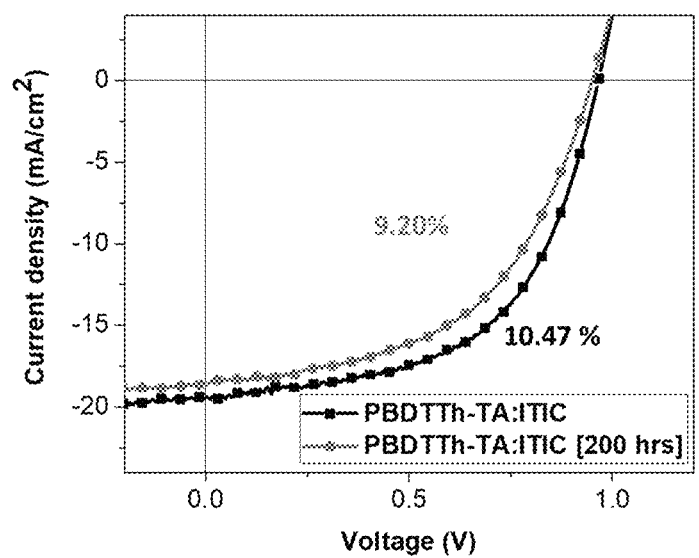

FIG. 17 shows photovoltaic performance stability of a PBDTTh-TA:ITIC device (unencapsulated) after 200 hours in air.

Figure 18:
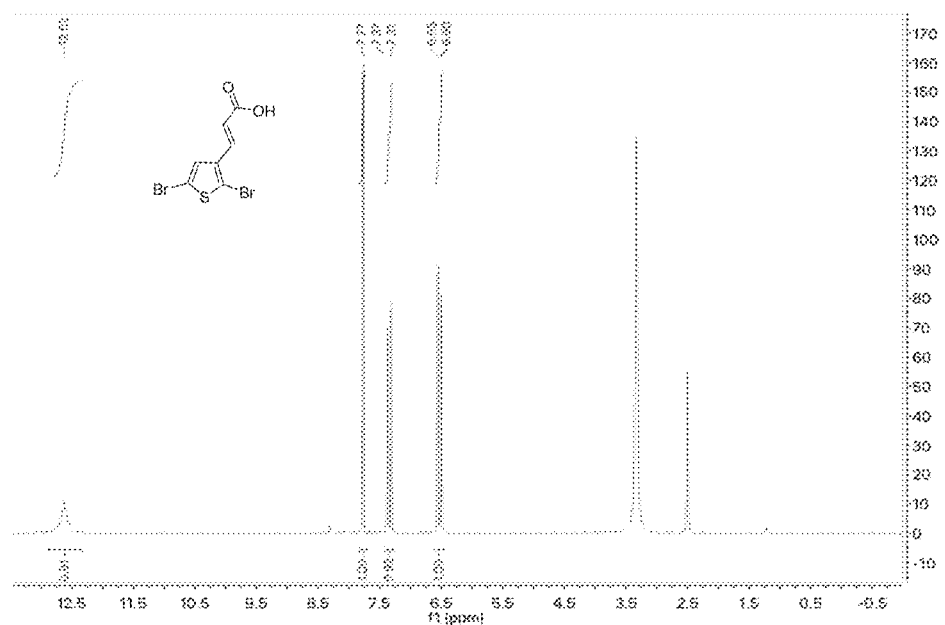

FIG. 18 shows $^1$H NMR (300 MHz, DMSO) spectra of (E)-3-(2,5-dibromothiophen-3-yl) acrylic acid ("2" from Scheme 2 below).

Figure 19:
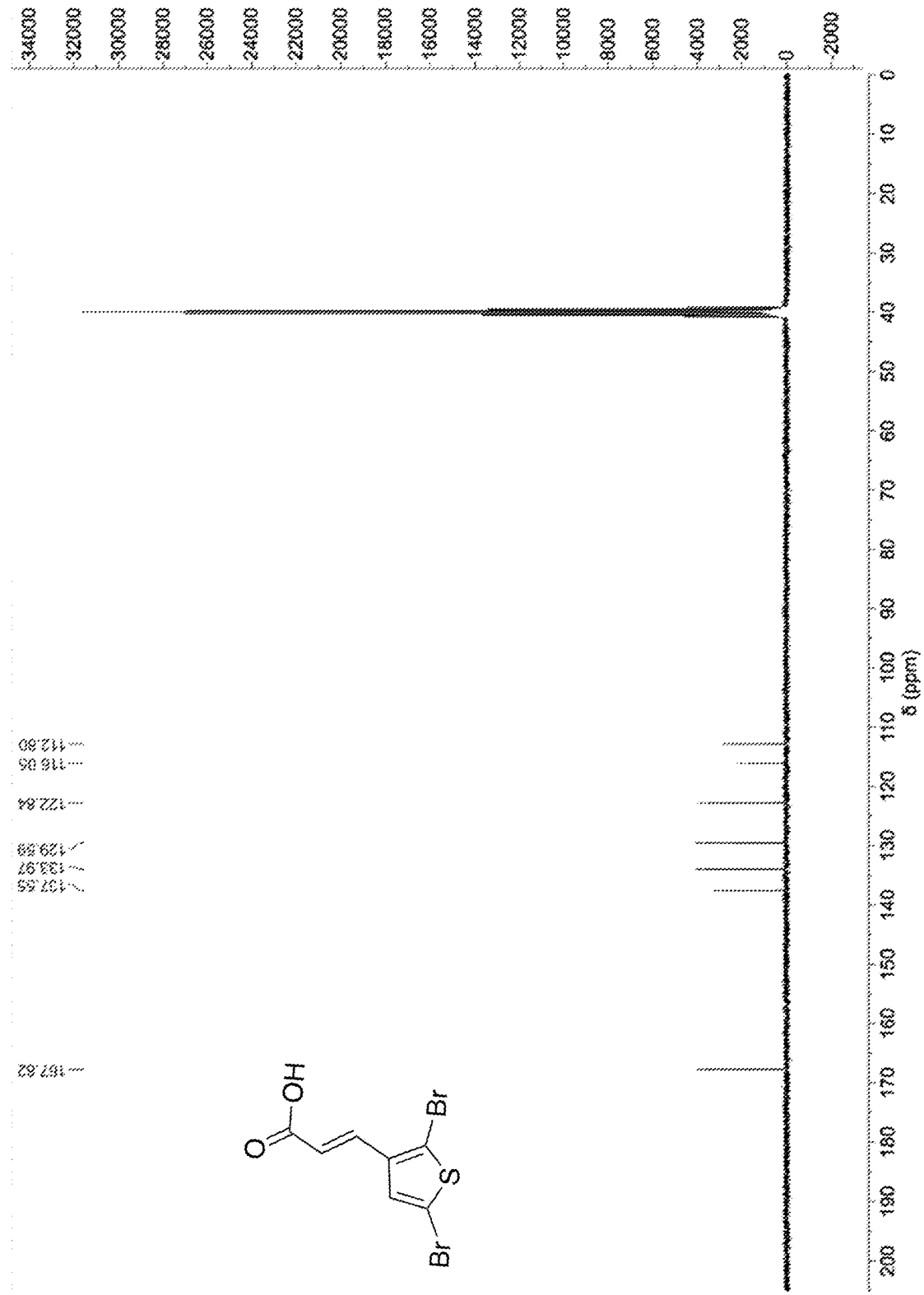

FIG. 19 shows $^{13}$C NMR (300 MHz, DMSO) spectra of (E)-3-(2,5-dibromothiophen-3-yl) acrylic acid ("2" from Scheme 2 below).

Figure 20:
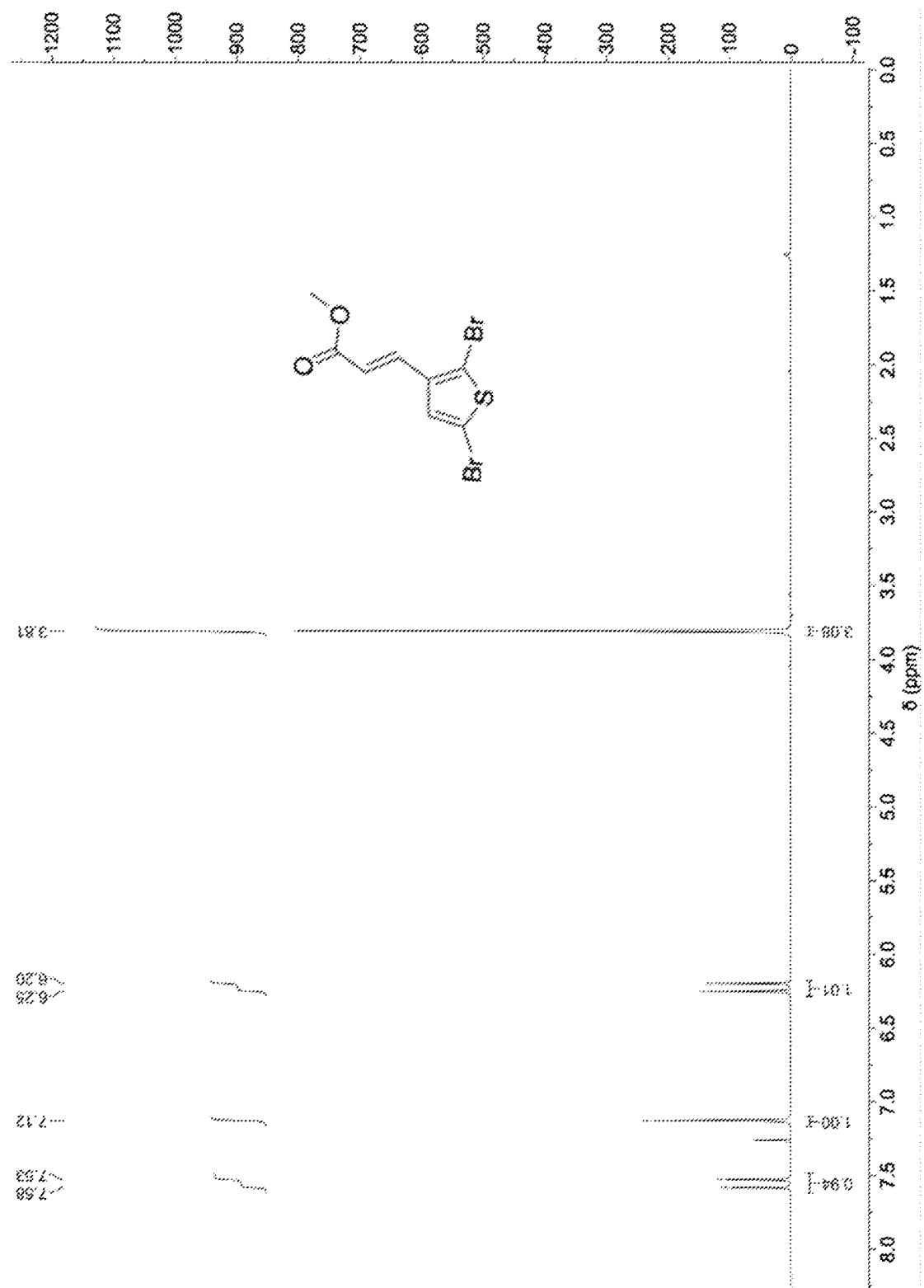

FIG. 20 shows $^1$H NMR (300 MHz, CDCl$_3$) spectra of methyl (E)-3-(2,5-dibromothiophen-3-yl) acrylate ("3" from Scheme 2 below).

Figure 21:
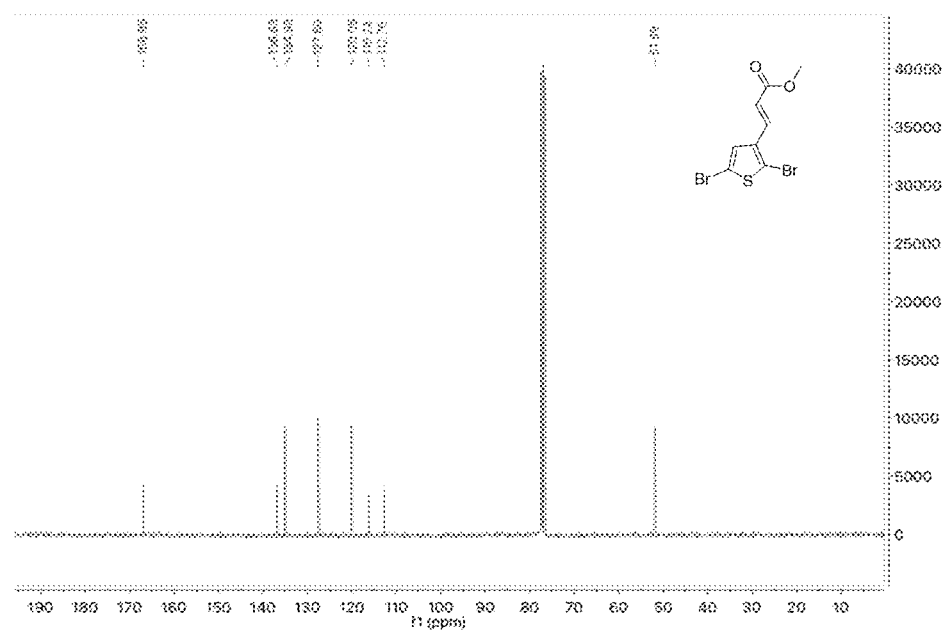

FIG. 21 shows $^{13}$C NMR (300 MHz, CDCl$_3$) spectra of methyl (E)-3-(2,5-dibromothiophen-3-yl) acrylate ("3" from Scheme 2 below).

Figure 22:
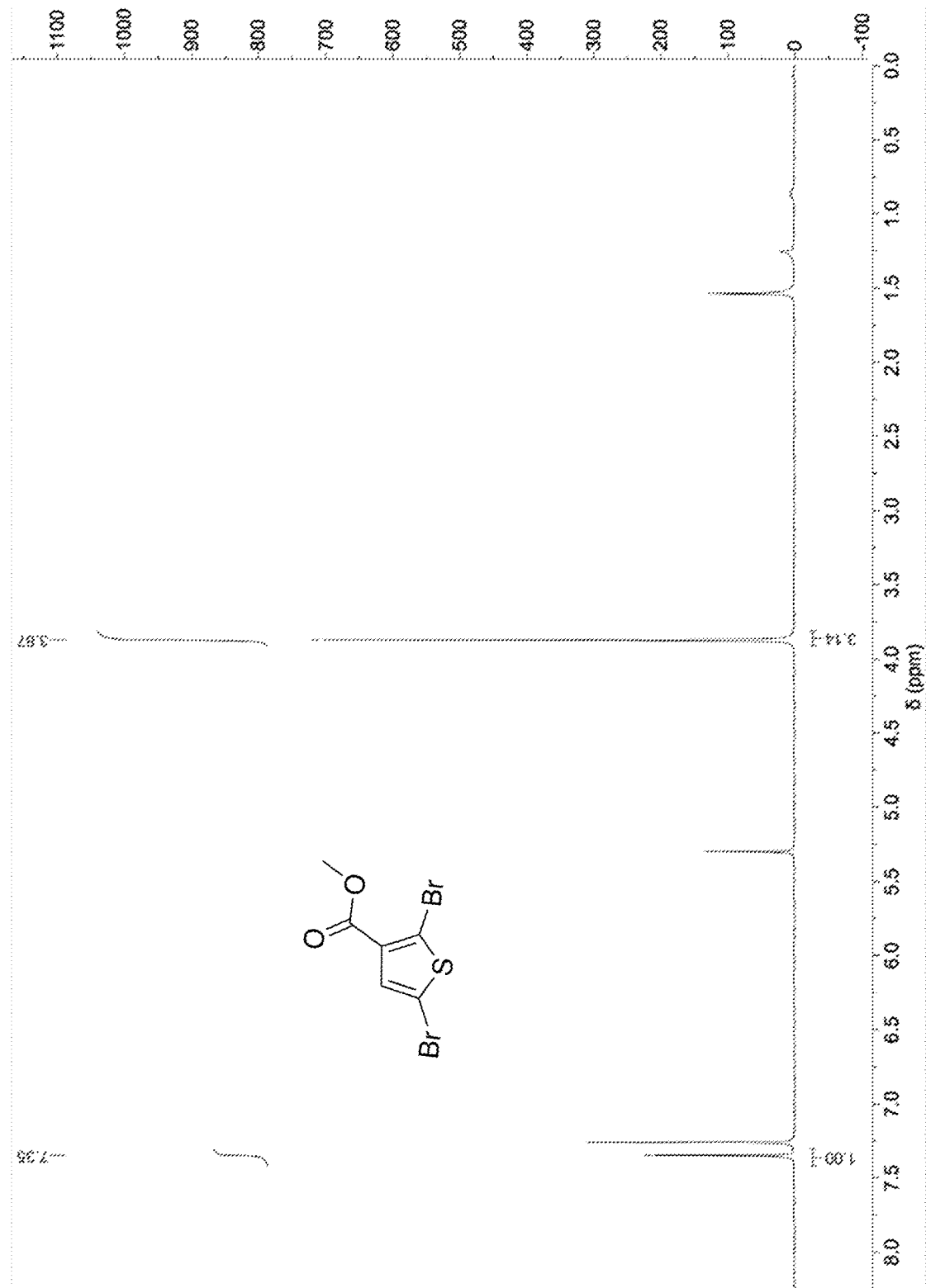

FIG. 22 shows $^1$H NMR (300 MHz, CDCl$_3$) spectra of methyl 2,5-dibromothiophene-3-carboxylate ("6" from Scheme 2 below).

DETAILED DESCRIPTION

The exemplary embodiments disclosed herein are illustrative of advantageous semiconductor materials, and assemblies/systems of the present disclosure and methods/techniques thereof. It should be understood, however, that the disclosed embodiments are merely exemplary of the present disclosure, which may be embodied in various forms. Therefore, details disclosed herein with reference to exemplary semiconductor materials and associated processes/techniques of assembly and use are not to be interpreted as limiting, but merely as the basis for teaching one skilled in the art how to make and use the advantageous semiconductor materials of the present disclosure.

The present disclosure provides improved semiconductor materials, and advantageous systems and methods for utilizing and fabricating the semiconductor materials.

In exemplary embodiments, the present disclosure provides monomeric, oligomeric and/or polymeric semiconductor materials having a five-membered heteroaromatic unit (e.g., thiophene; furan; selenophene; etc.) that is substituted with an acrylyl or an acrylyl-like (—C=C—CO—) side chain.

For the purposes of the present disclosure the term "substituted" is used to denote substitution, e.g., replacement of a hydrogen, by a substituent selected from the group consisting of halogen atoms, alkyl having from 1 to 60 carbon atoms, alkyl having from 1 to 60 carbon atoms wherein at least one of the hydrogen atoms is replaced by a halogen atom, alkyl having from 1 to 60 carbon atoms wherein at least one of the methylene moieties ($CH_2$) is replaced by an oxygen atom, aryl having from 5 to 20 ring atoms with the ring atoms being independently of each other selected from the group consisting of carbon and heteroatoms, and aryl having from 5 to 20 ring atoms with the ring atoms being independently of each other selected from the group consisting of carbon and heteroatoms and at least one hydrogen is replaced by a halogen atom.

For the purposes of the present disclosure the term "polymer" will be understood to mean a molecule of high relative molecular mass, the structure of which essentially comprises the multiple repetition of units derived, actually or conceptually, from molecules of low relative molecular mass (Pure Appl. Chem., 1996, 68, 2291). The term "oligomer" will be understood to mean a molecule of intermediate relative molecular mass, the structure of which essentially comprises a small plurality of units derived, actually or conceptually, from molecules of lower relative molecular mass (Pure Appl. Chem., 1996, 68, 2291). In a preferred meaning as used herein a polymer will be understood to mean a compound having greater than 1, e.g., at least 2 repeat units, preferably greater than or equal to 5 repeat units, and an oligomer will be understood to mean a compound with greater than 1 and less than 10, preferably less than 5, repeat units.

Further, as used herein, the term "polymer" will be understood to mean a molecule that encompasses a backbone (also referred to as "main chain") of one or more distinct types of repeat units (the smallest constitutional unit of the molecule) and is inclusive of the commonly known terms "oligomer", "copolymer", "homopolymer" and the like. Further, it will be understood that the term polymer is inclusive of, in addition to the polymer itself, residues from initiators, catalysts and other elements attendant to the synthesis of such a polymer, where such residues are understood as not being covalently incorporated thereto. Further, such residues and other elements, while normally removed during post polymerization purification processes, are typically mixed or co-mingled with the polymer such that they generally remain with the polymer when it is transferred between vessels or between solvents or dispersion media.

As used herein, the terms "repeat unit", "repeating unit" and "monomeric unit" are used interchangeably and will be understood to mean the constitutional repeating unit (CRU), which is the smallest constitutional unit the repetition of which constitutes a regular macromolecule, a regular oligomer molecule, a regular block or a regular chain (Pure Appl. Chem., 1996, 68, 2291). As further used herein, the term "unit" will be understood to mean a structural unit which can be a repeating unit on its own, or can together with other units form a constitutional repeating unit.

As used herein, a "terminal group" will be understood to mean a group that terminates a polymer backbone. The expression "in terminal position in the backbone" will be understood to mean a divalent unit or repeat unit that is linked at one side to such a terminal group and at the other side to another repeat unit. Such terminal groups include endcap groups or reactive groups that are attached to a monomer forming the polymer backbone which did not participate in the polymerization reaction, like for example a group having the meaning of $R^e$ or $R^f$ as defined below.

As used herein, the term "endcap group" will be understood to mean a group that is attached to, or replacing, a terminal group of the polymer backbone. The endcap group can be introduced into the polymer by an endcapping process. Endcapping can be carried out for example by reacting the terminal groups of the polymer backbone with a monofunctional compound ("endcapper") like for example an alkyl- or arylhalide, an alkyl- or arylstannane or an alkyl- or arylboronate. The endcapper can be added for example after the polymerization reaction. Alternatively the endcapper can be added in situ to the reaction mixture before or during the polymerization reaction. In situ addition of an endcapper can also be used to terminate the polymerization reaction and thus control the molecular weight of the forming polymer. Typical endcap groups are for example H, phenyl and alkyl having from 1 to 60 carbon atoms.

As used herein, the terms "donor" or "donating" and "acceptor" or "accepting" will be understood to mean an electron donor and electron acceptor, respectively. "Electron donor" will be understood to mean a chemical entity that donates electrons to another compound or another group of atoms of a compound. "Electron acceptor" will be understood to mean a chemical entity that accepts electrons transferred to it from another compound or another group of atoms of a compound. See also International Union of Pure and Applied Chemistry, Compendium of Chemical Technology, Gold Book, Version 2.3.2, 19 Aug. 2012, pages 477 and 480.

As used herein, the term "n-type" or "n-type semiconductor" will be understood to mean an extrinsic semiconductor in which the conduction electron density is in excess of the mobile hole density, and the term "p-type" or "p-type semiconductor" will be understood to mean an extrinsic semiconductor in which mobile hole density is in excess of the conduction electron density (see also, J. Thewlis, Concise Dictionary of Physics, Pergamon Press, Oxford, 1973).

As used herein, the term "leaving group" will be understood to mean an atom or group (which may be charged or uncharged) that becomes detached from an atom in what is considered to be the residual or main part of the molecule taking part in a specified reaction (see also Pure Appl. Chem., 1994, 66, 1134).

As used herein, the term "conjugated" will be understood to mean a compound (for example a polymer) that contains mainly C atoms with sp$^2$-hybridisation (or optionally also sp-hybridization), and wherein these C atoms may also be replaced by hetero atoms. In the simplest case this is for example a compound with alternating C—C single and double (or triple) bonds, but is also inclusive of compounds with aromatic units like for example 1,4-phenylene. The term "mainly" in this connection will be understood to mean that a compound with naturally (spontaneously) occurring defects, or with defects included by design, which may lead to interruption of the conjugation, is still regarded as a conjugated compound. See also International Union of Pure and Applied Chemistry, Compendium of Chemical Technology, Gold Book, Version 2.3.2, 19 Aug. 2012, pages 322-323.

As used herein, unless stated otherwise the molecular weight is given as the number average molecular weight $M_n$ or weight average molecular weight $M_w$, which is determined by gel permeation chromatography (GPC) against polystyrene standards in eluent solvents such as tetrahydrofuran, trichloromethane (TCM, chloroform), chlorobenzene or 1,2,4-trichlorobenzene. Unless stated otherwise, 1,2,4-trichlorobenzene is used as solvent. The molecular weight distribution ("MWD"), which may also be referred to as polydispersity index ("PDI"), of a polymer is defined as the ratio $M_w/M_n$. The degree of polymerization, also referred to as total number of repeat units, m (or n), will be understood to mean the number average degree of polymerization given as m (or n)=$M_n/M_u$, wherein $M_n$ is the number average molecular weight and $M_u$ is the molecular weight of the single repeat unit, see J. M. G. Cowie, *Polymers: Chemistry & Physics of Modern Materials*, Blackie, Glasgow, 1991.

The present disclosure relates to the development and applications of monomeric, oligomeric and/or polymeric semiconductor materials comprising a five-membered heteroaromatic unit (e.g., thiophene; furan; selenophene; etc.) that comprises an acrylyl or an acrylyl-like (—C=C—CO—) side chain as shown in (I):

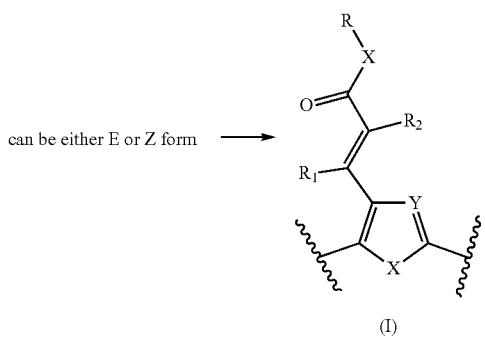

can be either E or Z form (I)

It is noted that the acrylyl or the acrylyl-like (—C=C—CO—) side chain can be either in the E form, or in the Z form.

As shown in (I), X is oxygen (O), sulphur (S), selenium (Se), or NR (R is hydrogen (H), or an optionally substituted hydrocarbon with about 1 to about 60 carbon (C) atoms (such as, for example, alkyl, substituted alkyl, alkenyl, substituted alkenyl, alkynyl, substituted alkynyl, aryl, substituted aryl, alkoxy, and substituted alkoxy), cyano (CN), nitro, or halogen, or any other suitable group, or any suitable substituent, such as F, Cl, or CN).

As shown in (I), Y is CR" (R" is hydrogen (H), or an optionally substituted hydrocarbon with about 1 to about 60 carbon (C) atoms (such as, for example, alkyl, substituted alkyl, alkenyl, substituted alkenyl, alkynyl, substituted alkynyl, aryl, substituted aryl, alkoxy, and substituted alkoxy), cyano (CN), nitro, or halogen, or any other suitable group, or any suitable substituent, such as F, Cl, or CN) or N.

As shown in (I), R, $R_1$ or $R_2$ is hydrogen (H), or an optionally substituted hydrocarbon with about 1 to about 60 carbon (C) atoms (such as, for example, alkyl, substituted alkyl, alkenyl, substituted alkenyl, alkynyl, substituted alkynyl, aryl, substituted aryl), F, Cl, or CN, or any suitable group.

An alkyl or alkoxy radical, e.g., where the terminal $CH_2$ group is replaced by —O—, can be straight-chain or branched. Suitable examples of such alkyl and alkoxy radical are methyl, ethyl, propyl, butyl, pentyl, hexyl, heptyl, octyl, nonyl, decyl, undecyl, dodecyl, tridecyl, tetradecyl, pentadecyl, methoxy, ethoxy, propoxy, butoxy, pentoxy, hexoxy, heptoxy, octoxy, nonoxy, decoxy, undecoxy, dodecoxy, tridecoxy or tetradecoxy. Preferred alkyl and alkoxy radicals have from 1 to 40 carbon atoms. Suitable examples of such preferred alkyl and alkoxy radicals may be selected from the group consisting of methyl, ethyl, propyl, butyl, pentyl, hexyl, heptyl, octyl, nonyl, decyl, undecyl, dodecyl, methoxy, ethoxy, propoxy, butoxy, pentoxy, hexoxy, heptoxy, octoxy, nonoxy, decoxy, undecoxy, and dodecoxy.

An alkenyl group, wherein one or more $CH_2$ groups are replaced by —CH=CH— can be straight-chain or branched. It preferably has 2 to 40 C atoms and accordingly is preferably vinyl, prop-1-enyl, or prop-2-enyl, but-1-enyl, but-2-enyl or but-3-enyl, pent-1-enyl, pent-2-enyl, pent-3-enyl or pent-4-enyl, hex-1-enyl, hex-2-enyl, hex-3-enyl, hex-4-enyl or hex-5-enyl, hept-1-enyl, hept-2-enyl, hept-3-enyl, hept-4-enyl, hept-5-enyl or hept-6-enyl, oct-1-enyl, oct-2-enyl, oct-3-enyl, oct-4-enyl, oct-5-enyl, oct-6-enyl or oct-7-enyl, non-1-enyl, non-2-enyl, non-3-enyl, non-4-enyl, non-5-enyl, non-6-enyl, non-7-enyl or non-8-enyl, dec-1-enyl, dec-2-enyl, dec-3-enyl, dec-4-enyl, dec-5-enyl, dec-6-enyl, dec-7-enyl, dec-8-enyl or dec-9-enyl.

Especially preferred alkenyl groups are $C_2$-$C_{20}$-1E-alkenyl, $C_4$-$C_{20}$-3E-alkenyl, $C_5$-$C_{20}$-4-alkenyl, and $C_6$-$C_{20}$-5-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Alkenyl groups having up to 12 C atoms are generally preferred.

The terms "aryl" and "heteroaryl" as used herein preferably mean a mono-, bi- or tricyclic aromatic or heteroaromatic group with 4 to 30 ring C atoms that may also comprise condensed rings and is optionally substituted with one or more groups L, wherein L is selected from halogen, —CN, —NC, —NCO, —NCS, —OCN, —SCN, —C(=O)NR$^0$R$^{00}$, —C(=O)X$^0$, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, or carbyl or hydrocarbyl with 1 to 60 C atoms that is optionally substituted and optionally comprises one or more heteroatoms, and is preferably alkyl, alkoxy, thiaalkyl, alkylcarbonyl, alkoxycarbonyl or alkoxycarbonyloxy with 1 to 40 C atoms that is optionally fluorinated, and R$^0$, R$^{00}$ and X$^0$ have the meanings given above and below.

Very preferred substituents L are selected from halogen, most preferably F, or alkyl, alkoxy, oxaalkyl, thioalkyl, fluoroalkyl and fluoroalkoxy with 1 to 24 C atoms or alkenyl, and alkynyl with 2 to 24 C atoms.

Especially preferred aryl and heteroaryl groups are phenyl, phenyl wherein one or more CH groups are replaced by N, naphthalene, thiophene, selenophene, thienothiophene, dithienothiophene, fluorene and oxazole, all of which can be unsubstituted, mono- or polysubstituted with L as defined above. Very preferred rings are selected from pyrrole, preferably N-pyrrole, furan, pyridine, preferably 2- or 3-pyridine, pyrimidine, pyridazine, pyrazine, triazole, tetrazole, pyrazole, imidazole, isothiazole, thiazole, thiadiazole, isoxazole, oxazole, oxadiazole, thiophene, preferably 2-thiophene, selenophene, preferably 2-selenophene, thieno[3,2-b]thiophene, thieno[2,3-b]thiophene, furo[3,2-b]furan, furo[2,3-b]furan, seleno[3,2-b]selenophene, seleno[2,3-b]selenophene, thieno[3,2-b]selenophene, thieno[3,2-b]furan, indole, isoindole, benzo[b]furan, benzo[b]thiophene, benzo[1,2-b;4,5-b']dithiophene, benzo[2,1-b;3,4-b']dithiophene, quinole, 2-methylquinole, isoquinole, quinoxaline, quinazoline, benzotriazole, benzimidazole, benzothiazole, benzisothiazole, benzisoxazole, benzoxadiazole, benzoxazole, benzothiadiazole, all of which can be unsubstituted, mono- or polysubstituted with L as defined above. Further examples of aryl and heteroaryl groups are those selected from the groups shown hereinafter.

Specifically, (I) is one of the following exemplary structures:

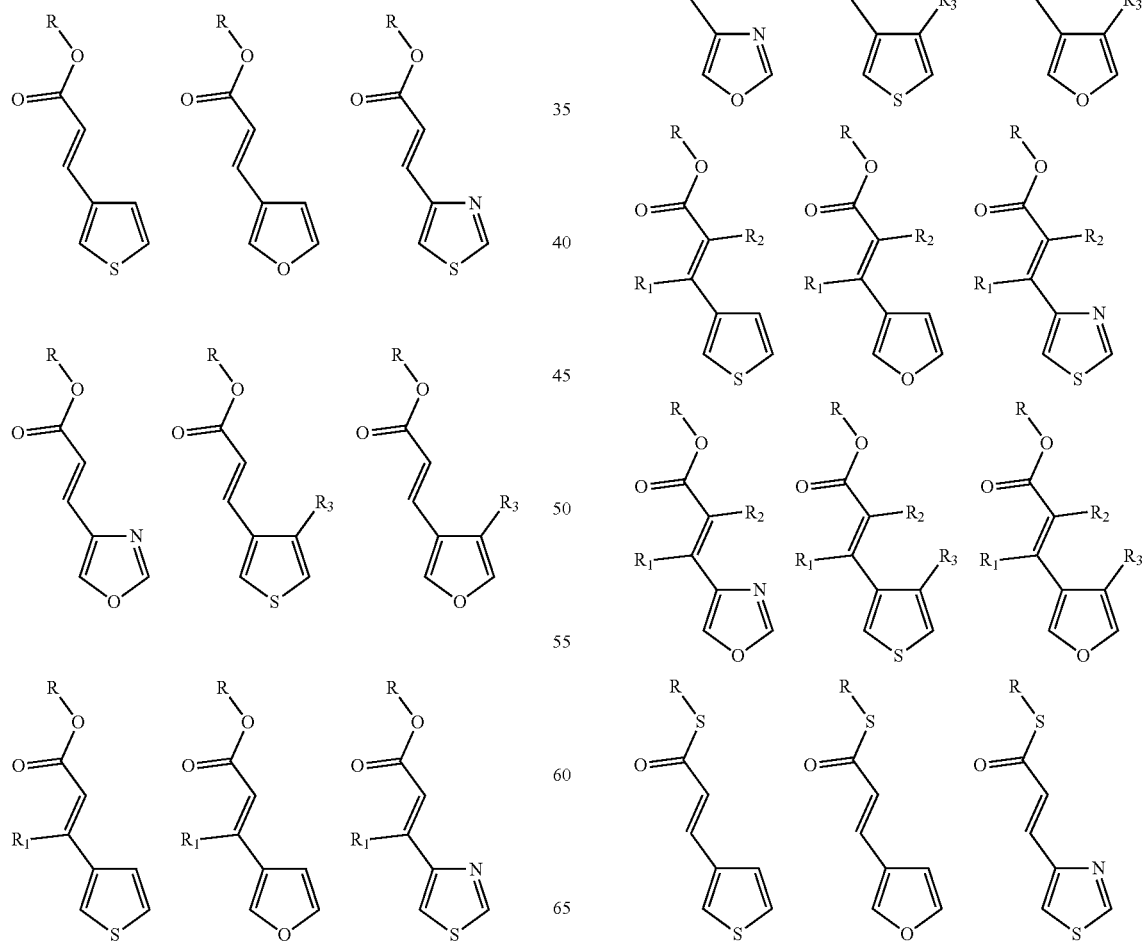

-continued

-continued

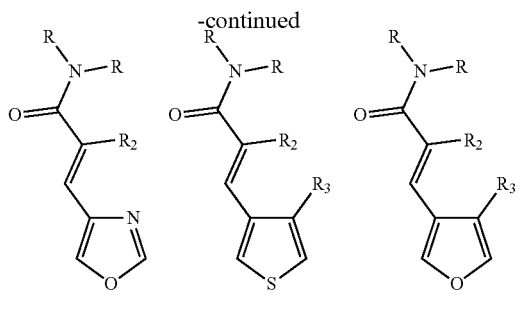

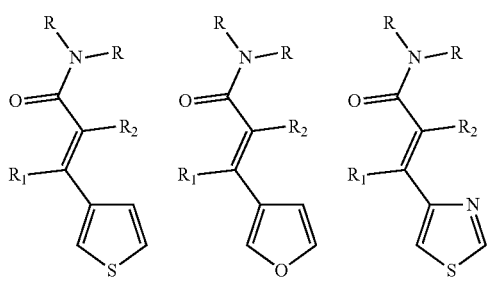

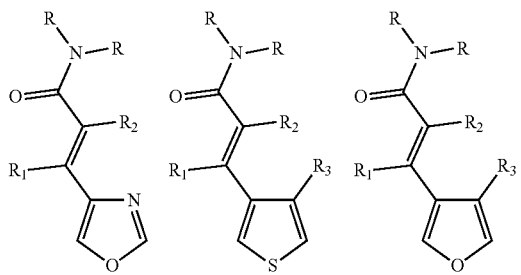

wherein:

R is hydrogen or an optionally substituted hydrocarbon with 1 to 60 carbon atoms such as, for example, alkyl, substituted alkyl, alkenyl, substituted alkenyl, alkynyl, substituted alkynyl, aryl, and substituted aryl), or any other suitable group;

$R_1$, $R_2$, and $R_3$ is an optionally substituted hydrocarbon with 1 to 60 carbon atoms such as, for example, alkyl, substituted alkyl, alkenyl, substituted alkenyl, alkynyl, substituted alkynyl, aryl, and substituted aryl), F, Cl, CN, or any other suitable group;

each structure can be further substituted, where is applicable, with one or more suitable groups independently selected from an optionally substituted hydrocarbon with 1 to 60 carbon atoms (such as, for example, alkyl, substituted alkyl, alkenyl, substituted alkenyl, alkynyl, substituted alkynyl, aryl, substituted aryl, alkoxy, and substituted alkoxy), cyano (CN), nitro, or halogen, or any other suitable group.

More specifically, this invention relates to the development of monomeric, oligomeric and polymeric semiconductor materials comprising a moiety (I) with the following general structure (PI):

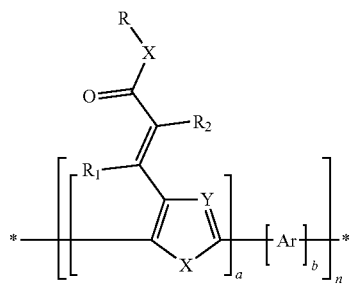

(PI)

wherein:

X, Y, R, $R_1$ and $R_2$ are defined as above;

a is an integer from 1 to 20;

b is an integer from 0 (zero) to 20;

the unit Ar and the unit (I) can be connected in a random or alternating manner, e.g., (PI) can be a random copolymer, an alternating copolymer, or a block copolymer;

n is a number from about 1 to 1,000,000;

the terminal "*" can be hydrogen, bromine or any other suitable group or moiety.

Ar is independently (e.g., in the case of b greater than 1, each Ar may have a different structure from the other) a π-conjugated moiety selected from, but not restricted to, the following structures and a combination of them:

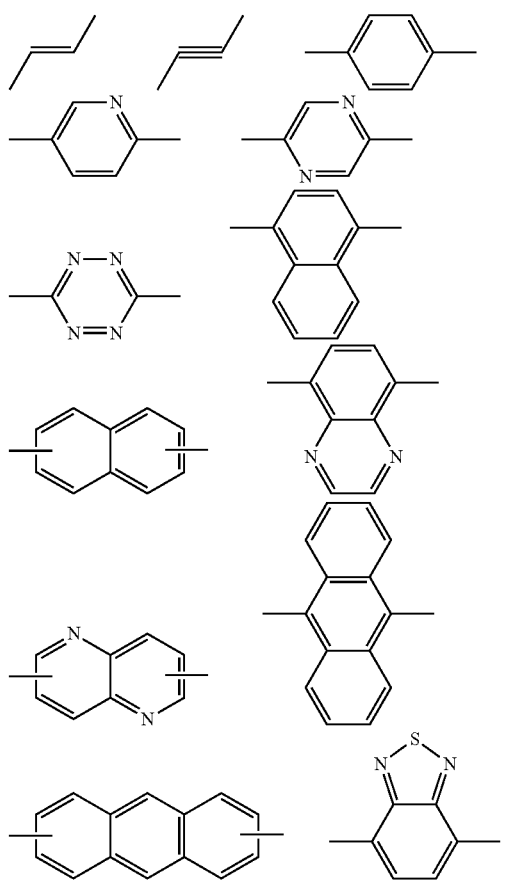

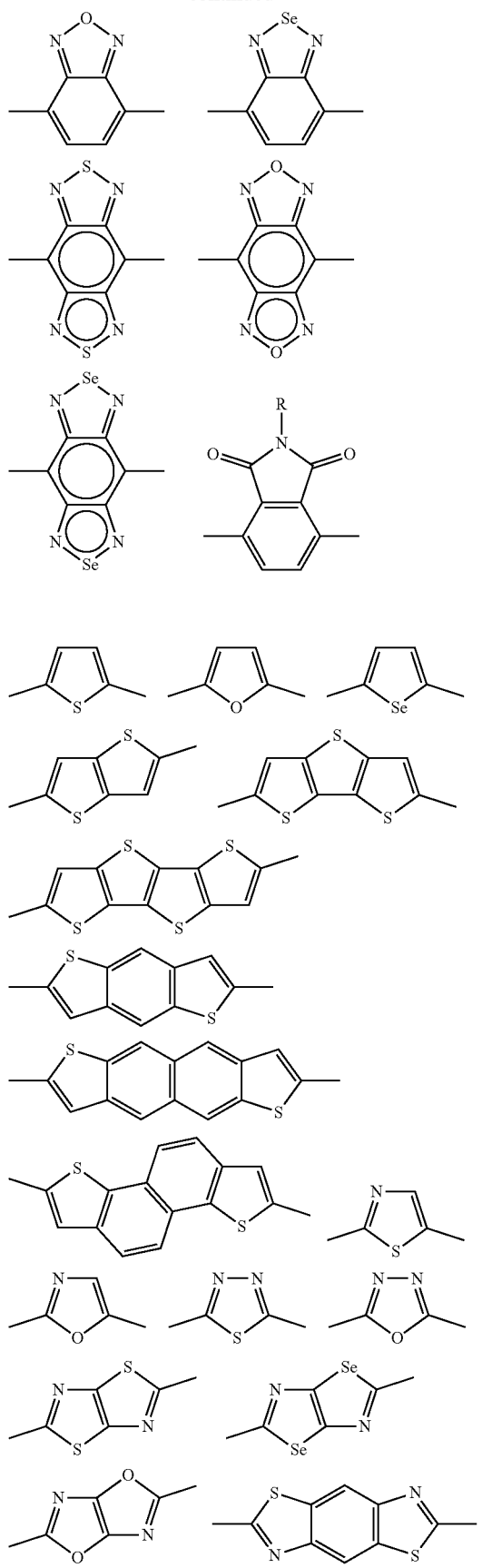
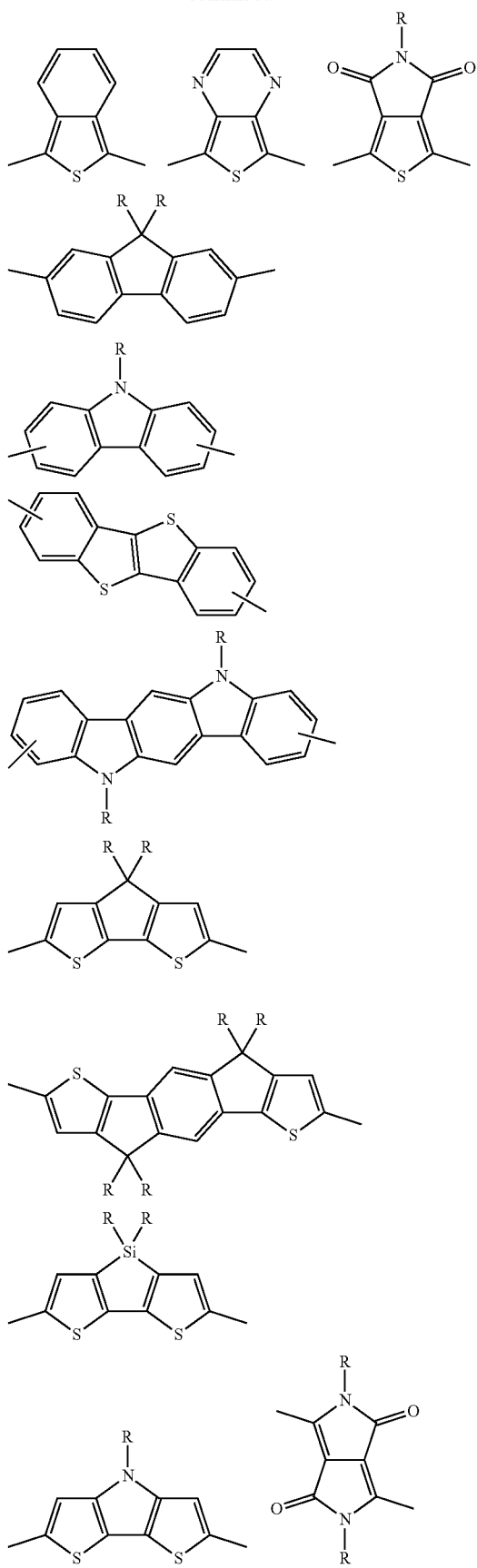

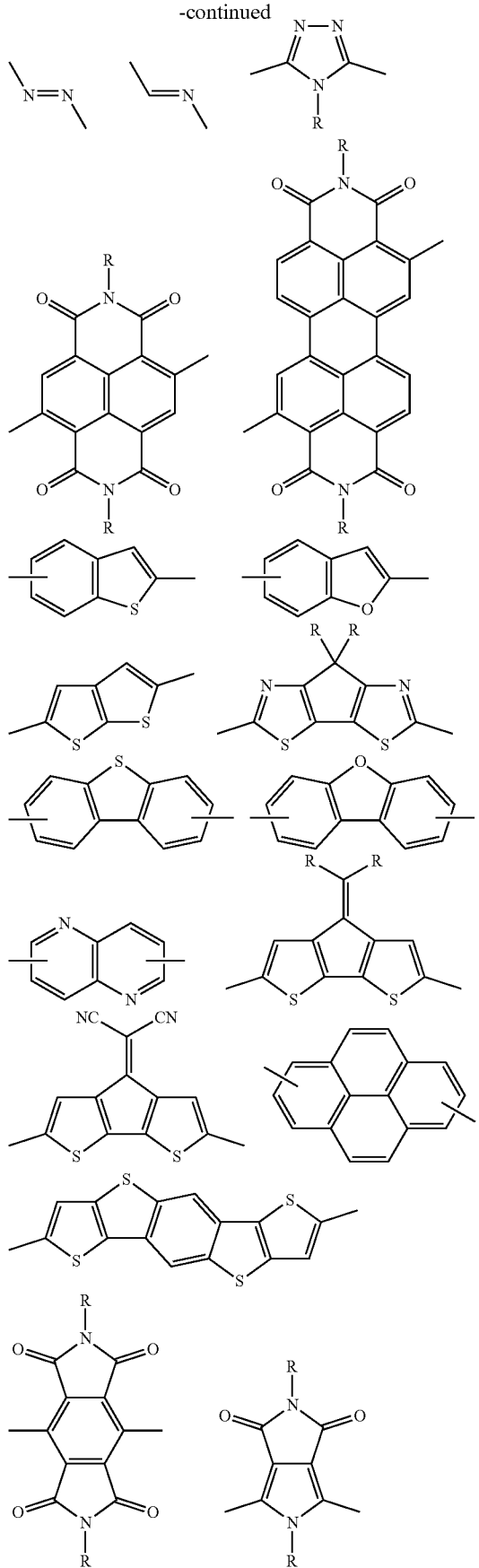
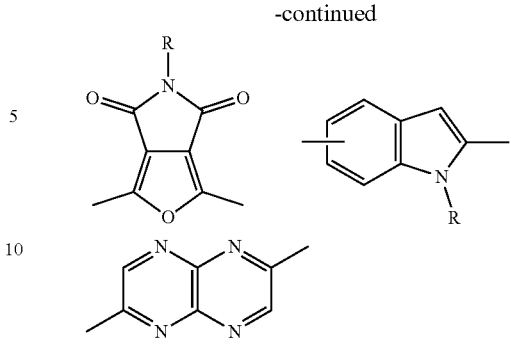

wherein each structure can be substituted, where is applicable, with one or more suitable groups independently selected from an optionally substituted hydrocarbon with 1 to 60 carbon atoms (such as, for example, alkyl, substituted alkyl, alkenyl, substituted alkenyl, alkynyl, substituted alkynyl, aryl, substituted aryl, alkoxy, and substituted alkoxy), cyano (CN), nitro, or halogen, or any other suitable group;

R is independently hydrogen, an optionally substituted hydrocarbon with 1 to 60 carbon atoms (such as, for example, alkyl, substituted alkyl, alkenyl, substituted alkenyl, alkynyl, substituted alkynyl, aryl, or substituted aryl), or any other suitable group.

Preferred embodiments of the present invention are illustrated in structures (1) through (186):

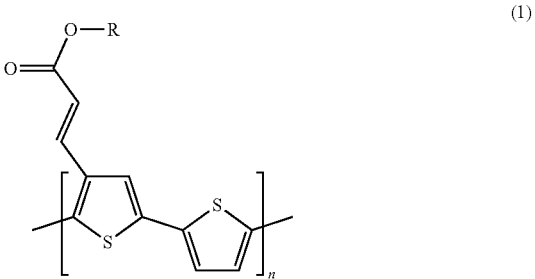

(1)

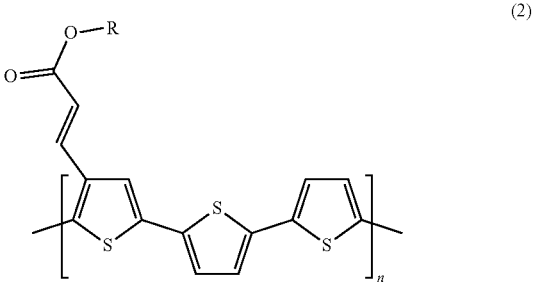

(2)

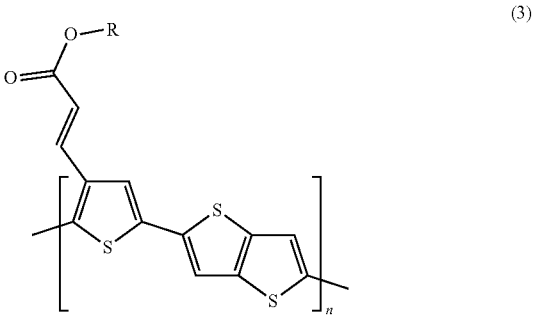

(3)

-continued
(4)
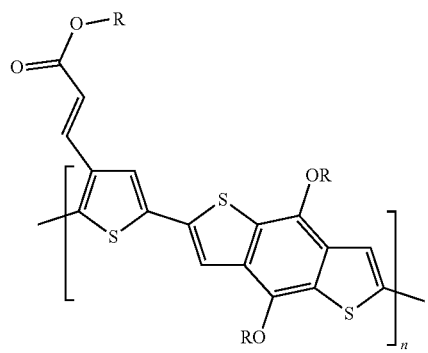
(5)
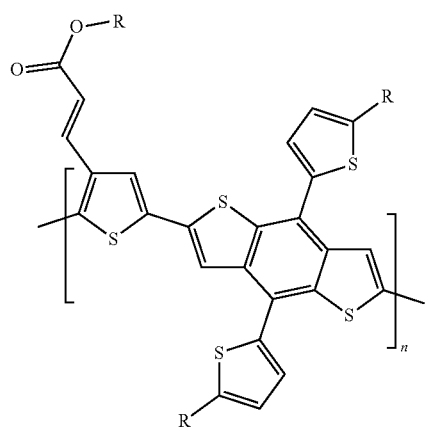
(6)
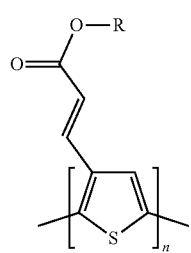
(7)
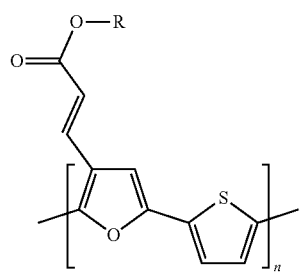
(8)
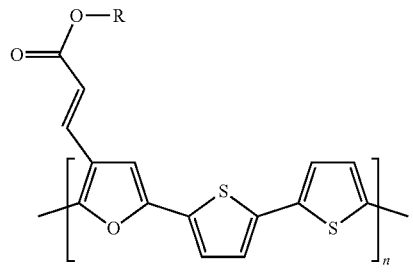
-continued
(9)
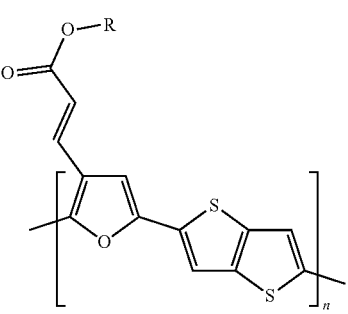
(10)
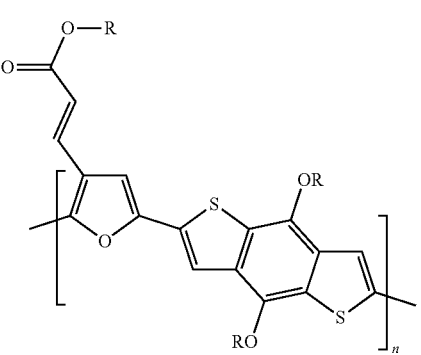
(11)
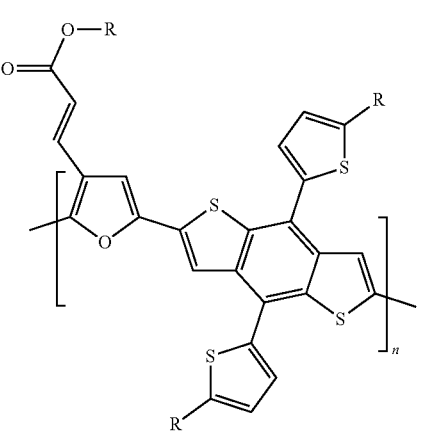
(12)
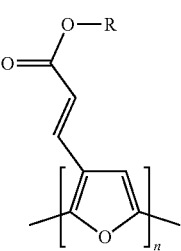
(13)
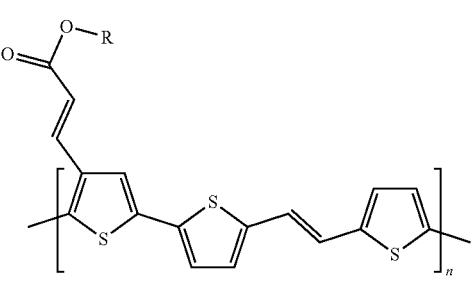

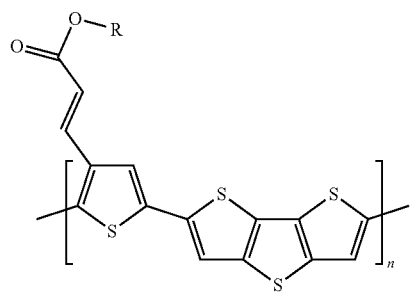
(14)
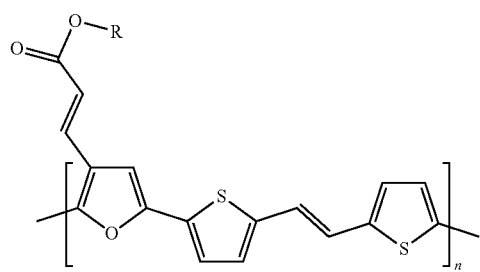
(15)
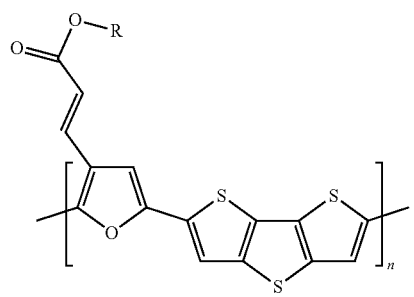
(16)
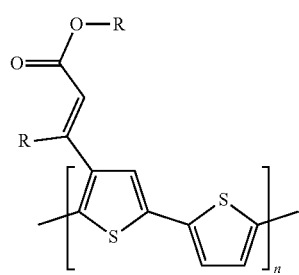
(17)
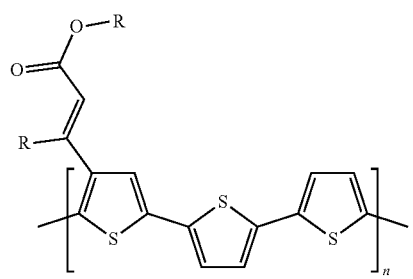
(18)
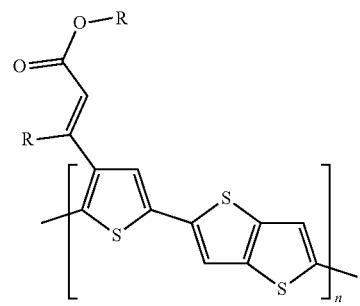
(19)
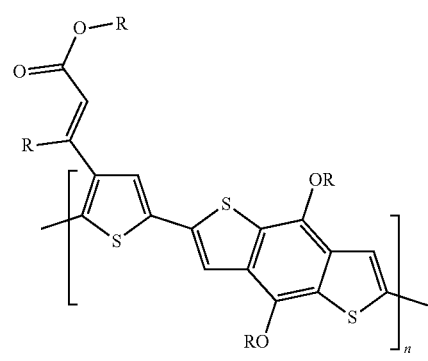
(20)
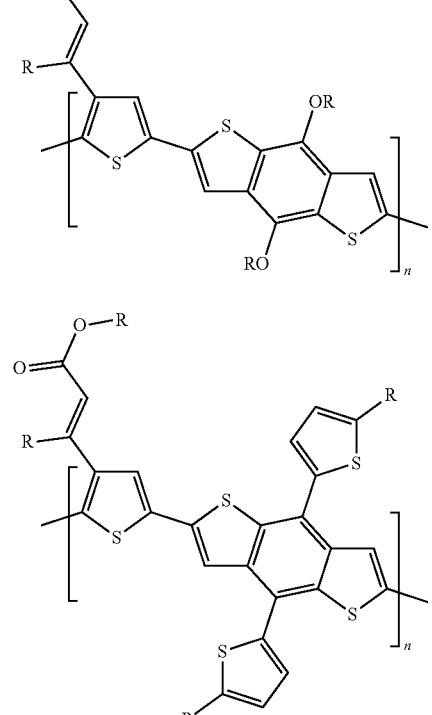
(21)
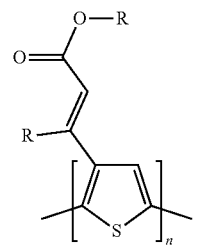
(22)
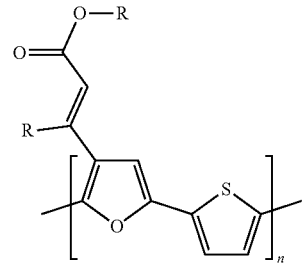
(23)

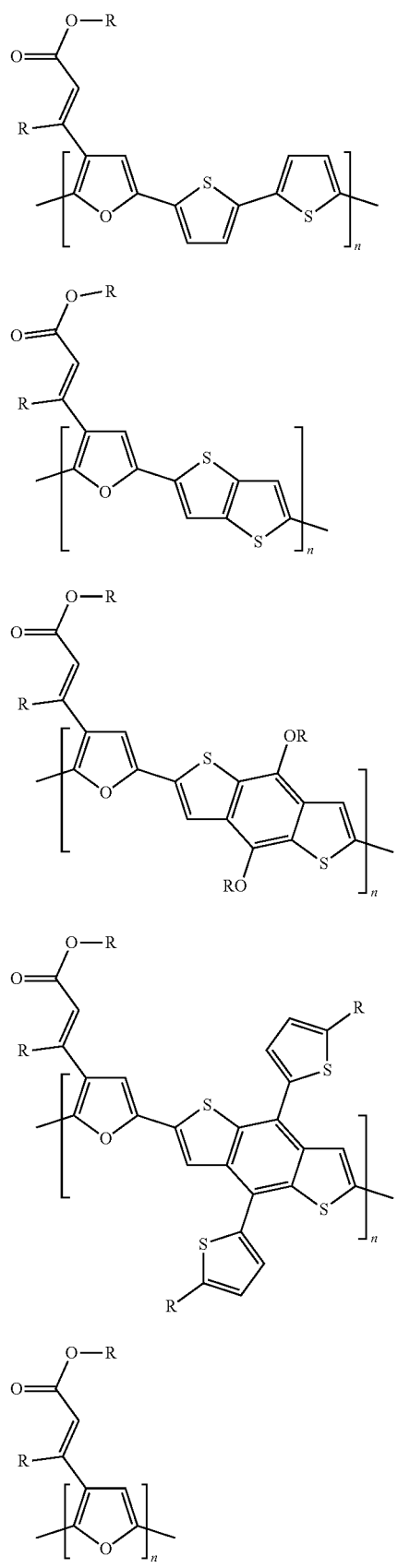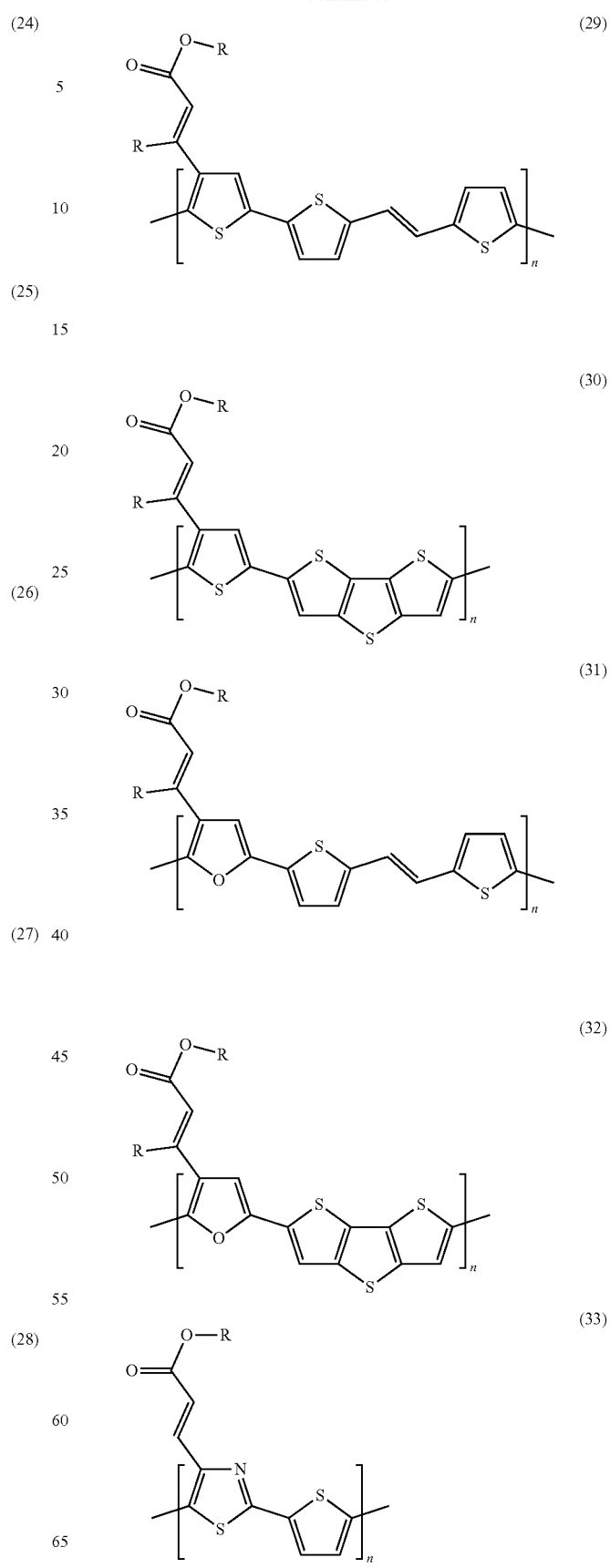

-continued
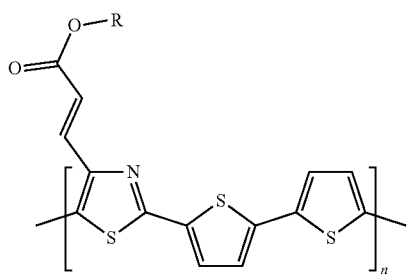
(34)
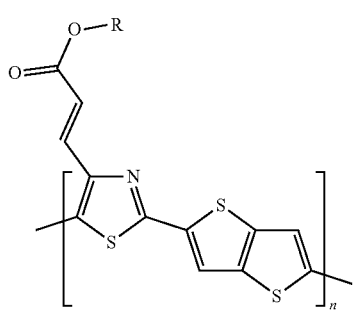
(35)
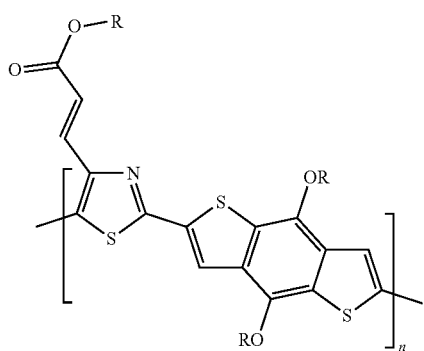
(36)
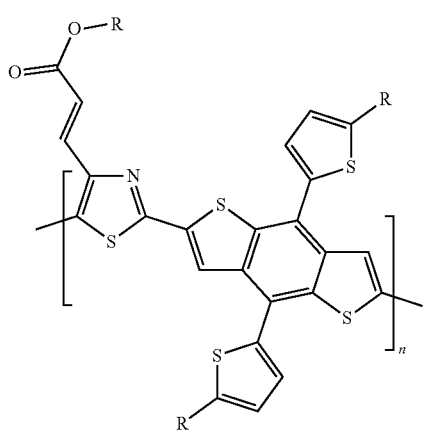
(37)
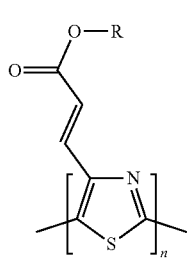
(38)
-continued
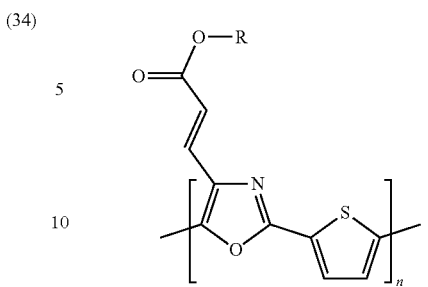
(39)
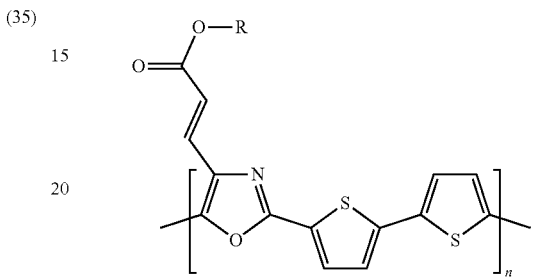
(40)
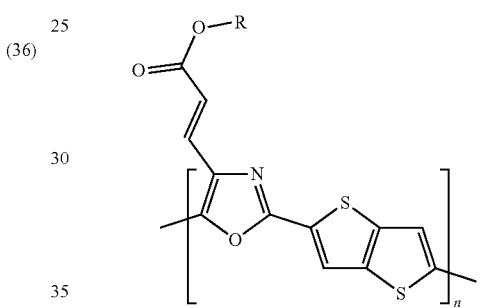
(41)
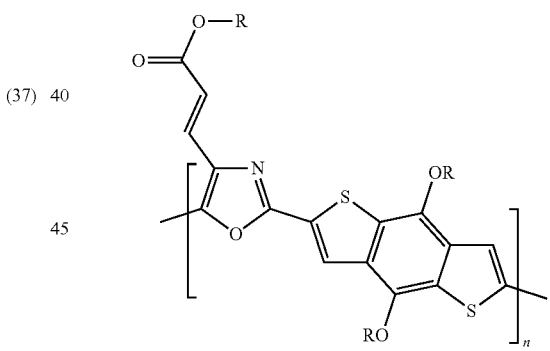
(42)
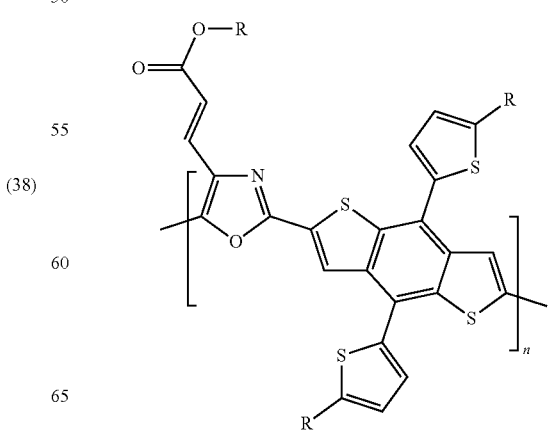
(43)

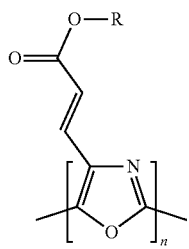
(44)
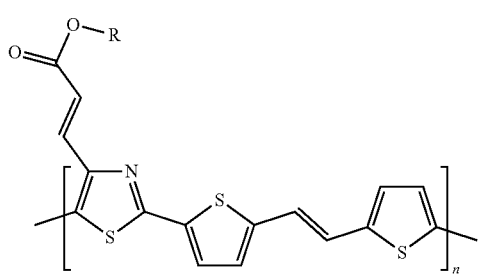
(45)
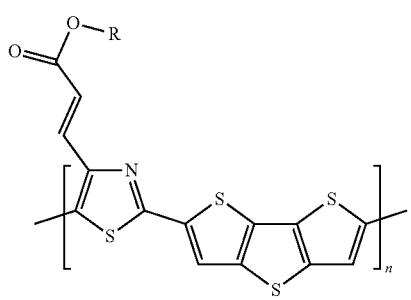
(46)
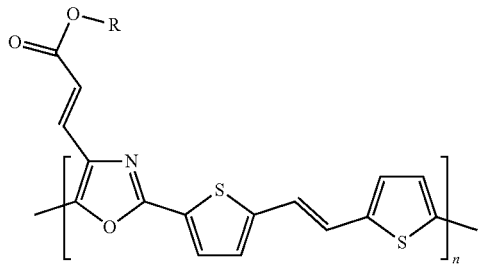
(47)
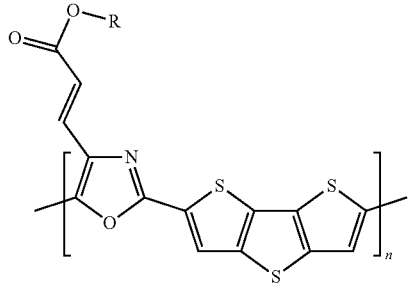
(48)
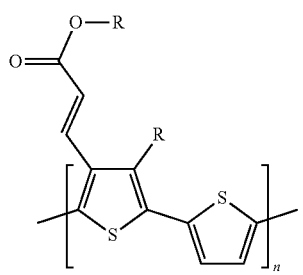
(49)
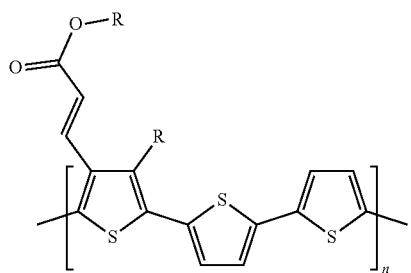
(50)
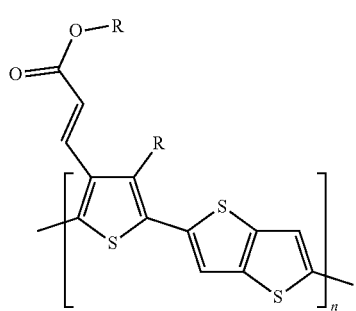
(51)
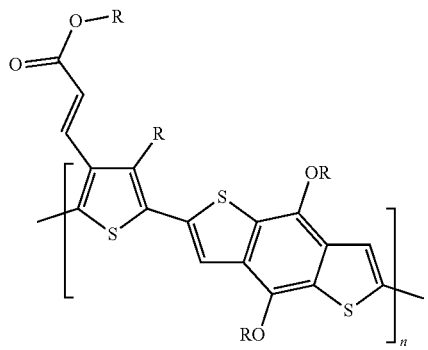
(52)
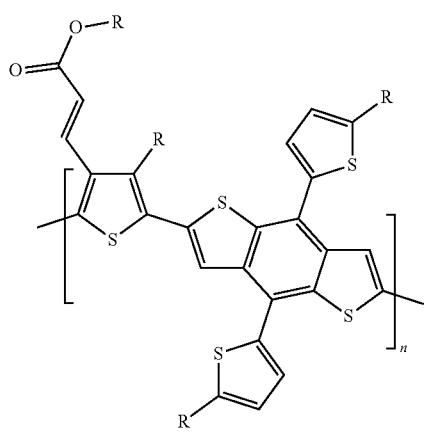
(53)

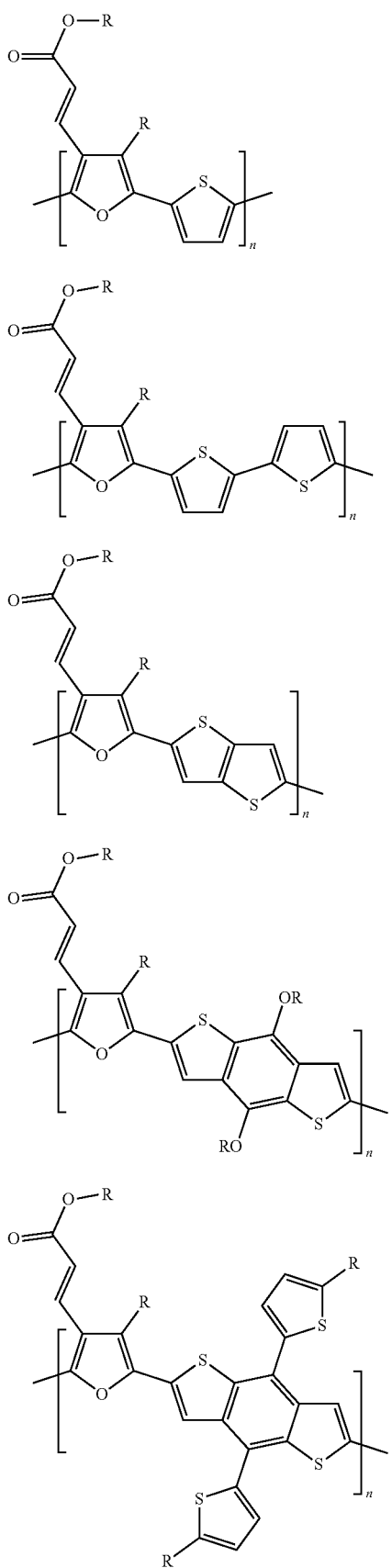
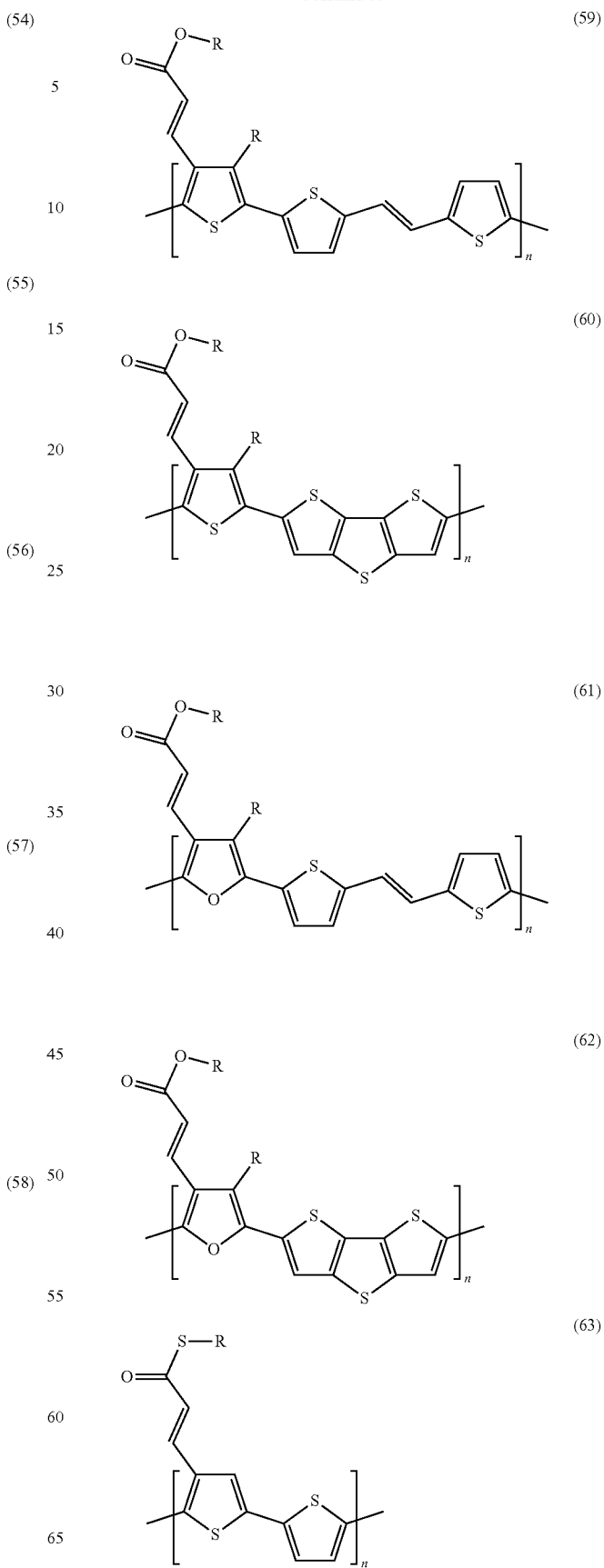

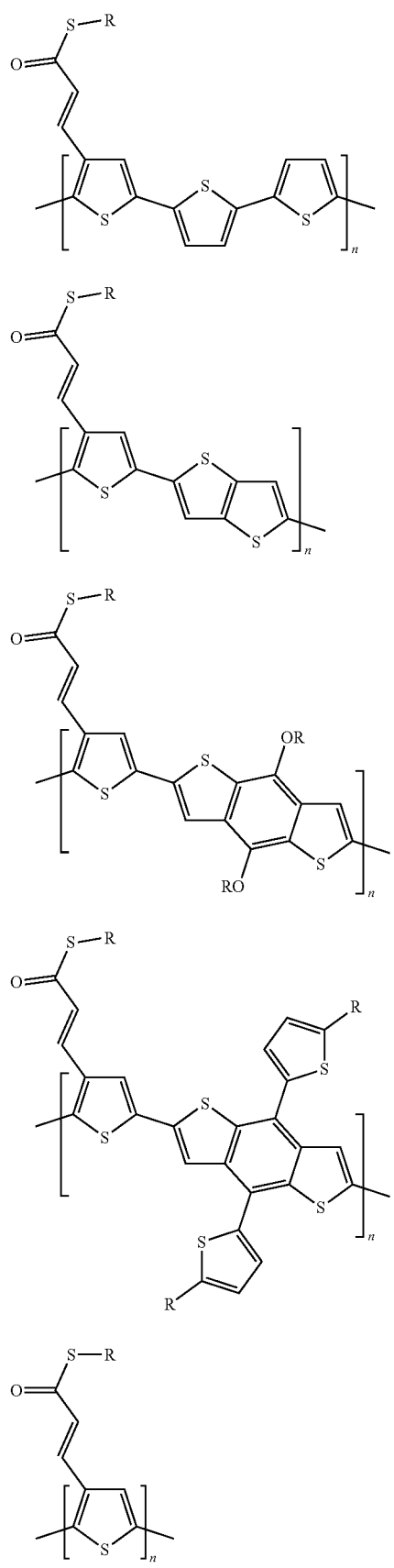
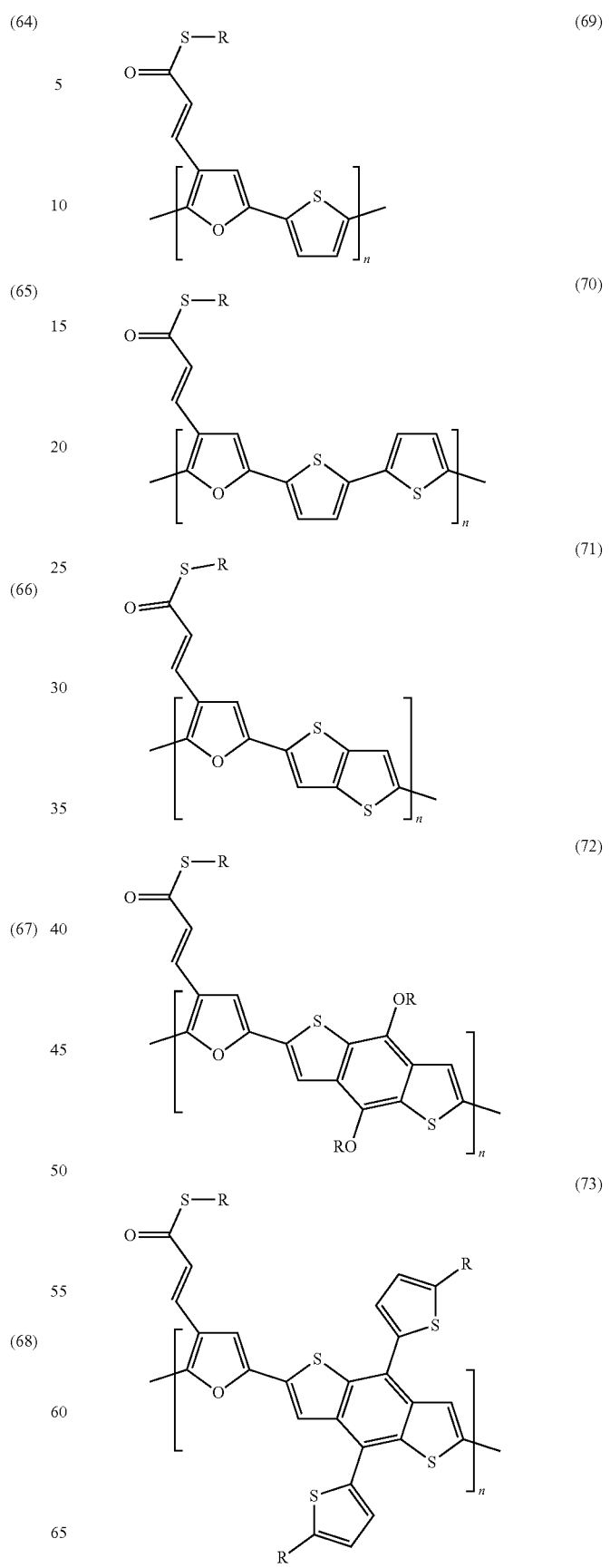

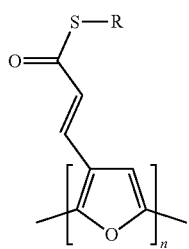
(74)
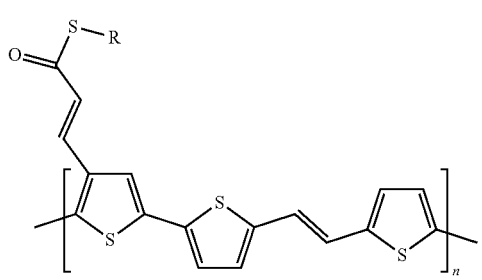
(75)
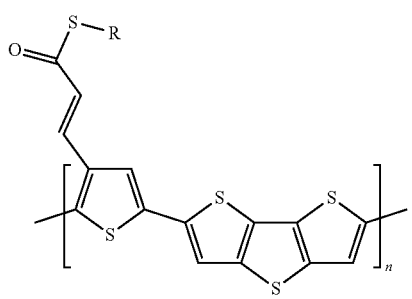
(76)
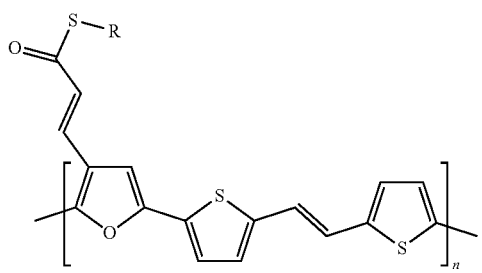
(77)
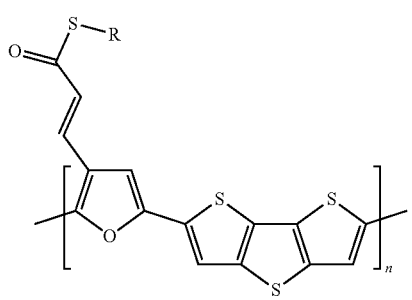
(78)
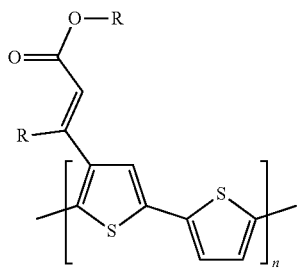
(79)
(80)
(81)
(82)
(83)

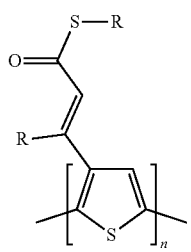
(84)
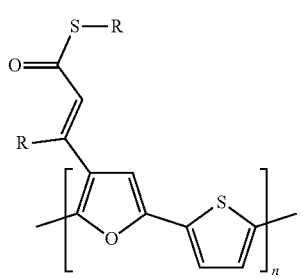
(85)
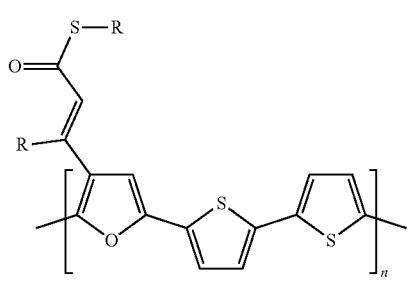
(86)
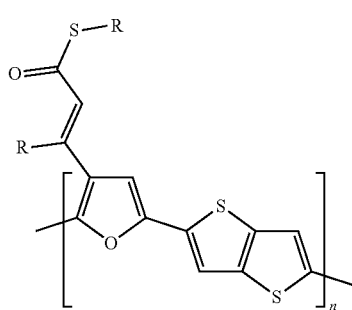
(87)
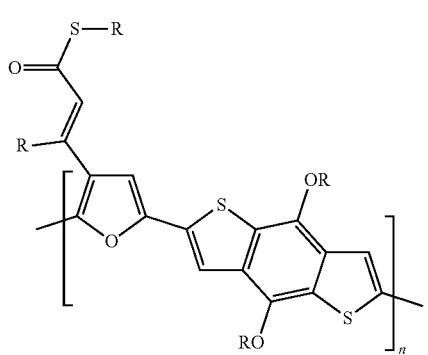
(88)

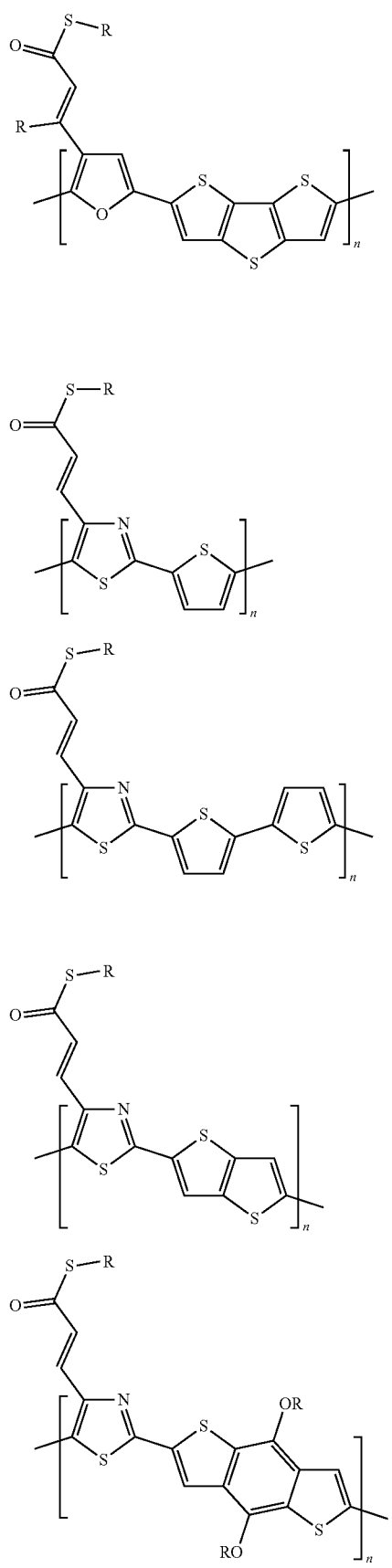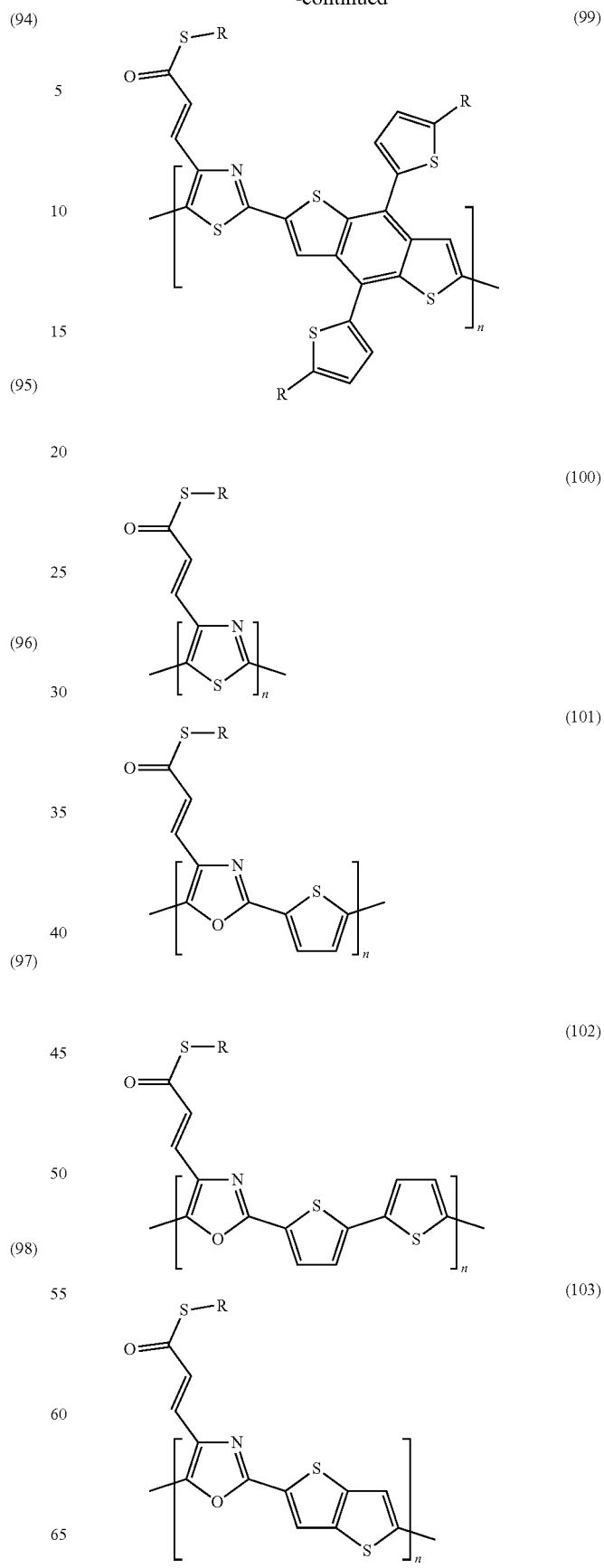

(104)
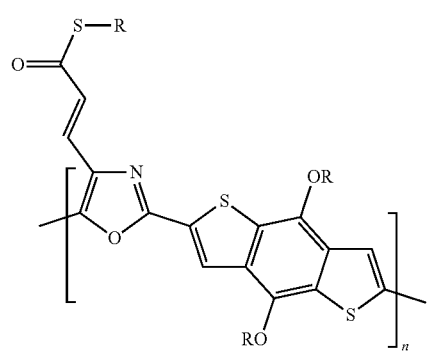
(105)
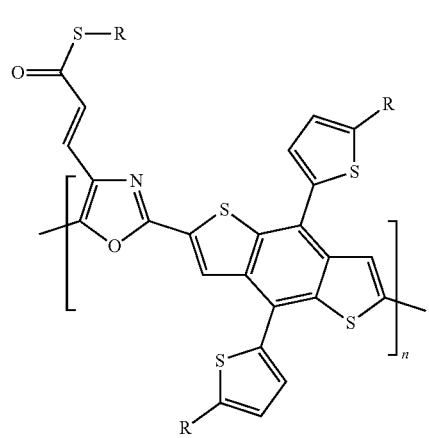
(106)
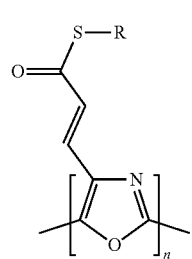
(107)
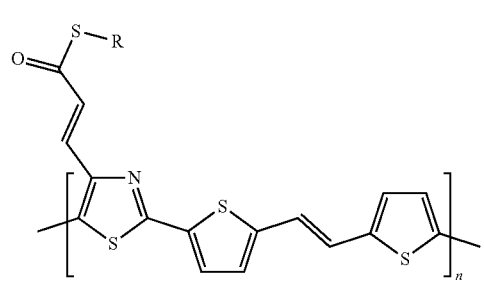
(108)
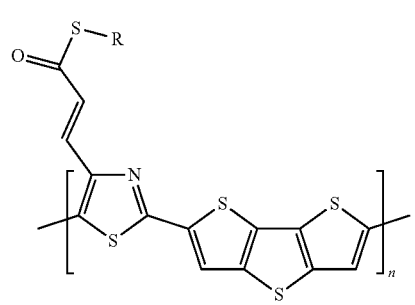
(109)
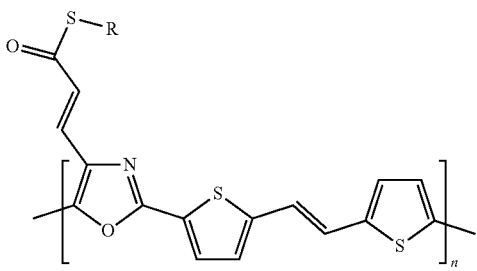
(110)
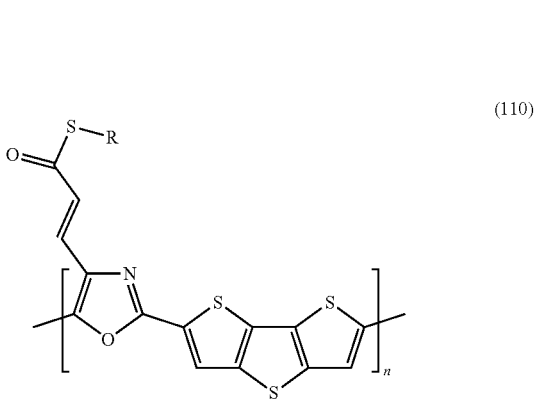
(111)
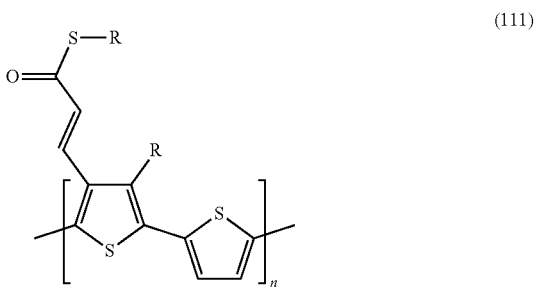
(112)
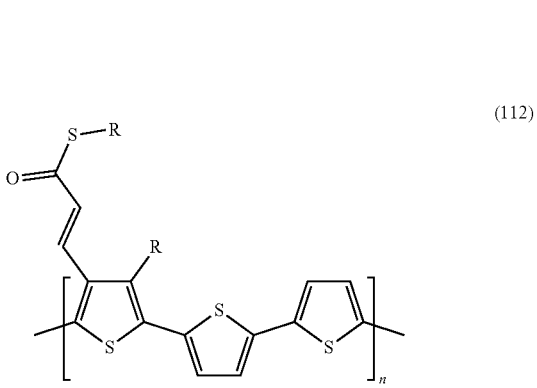
(113)
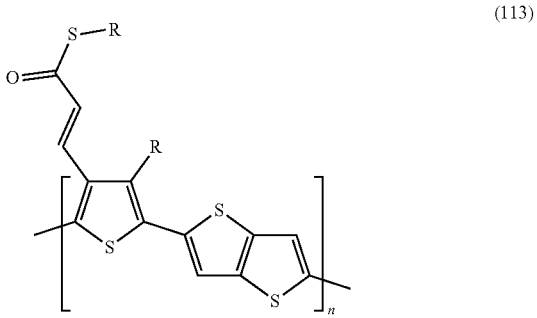

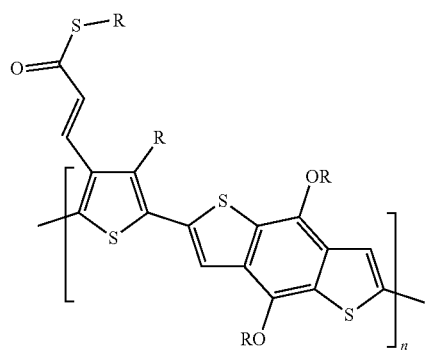
(114)
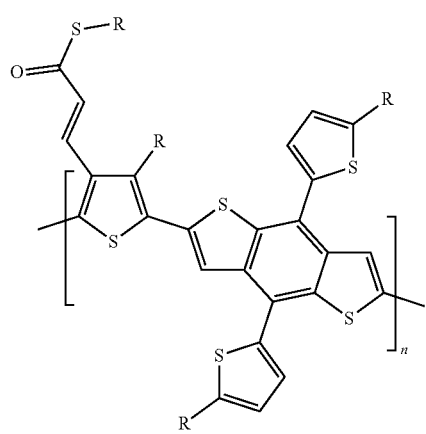
(115)
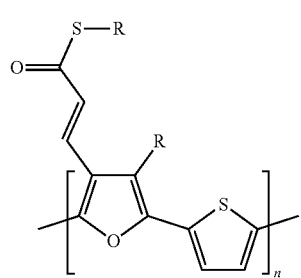
(116)
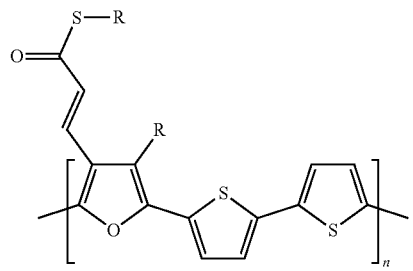
(117)
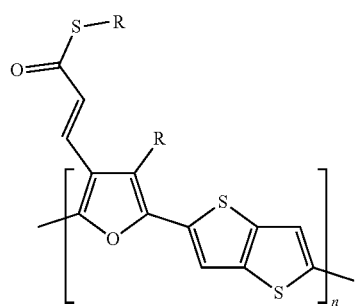
(118)
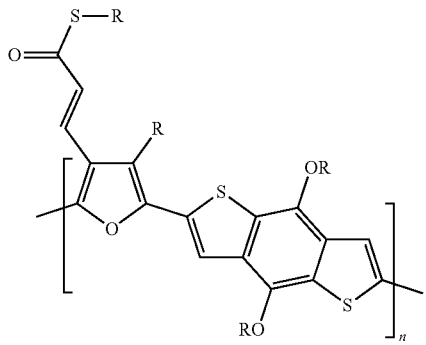
(119)
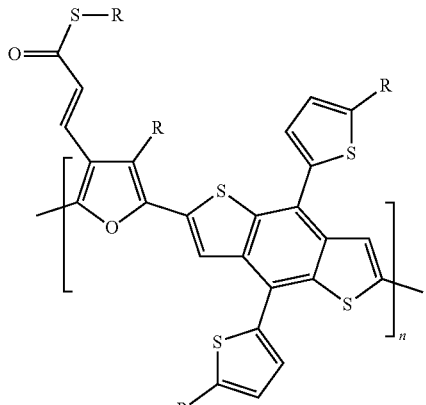
(120)
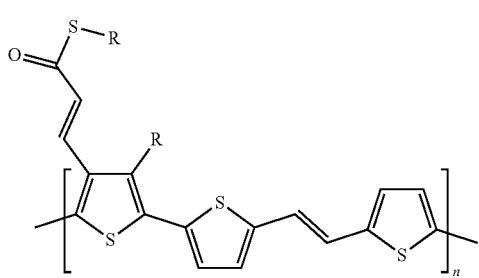
(121)
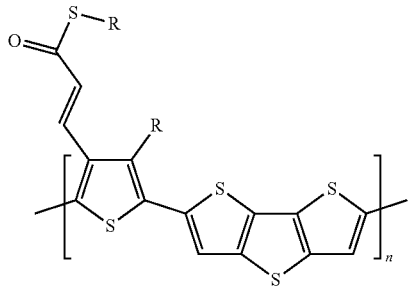
(122)
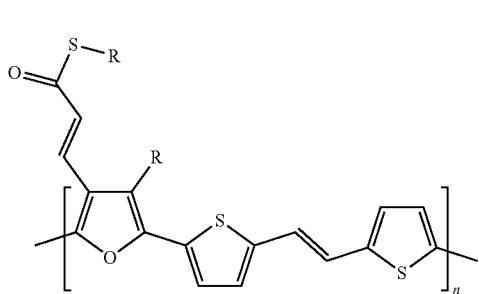
(123)

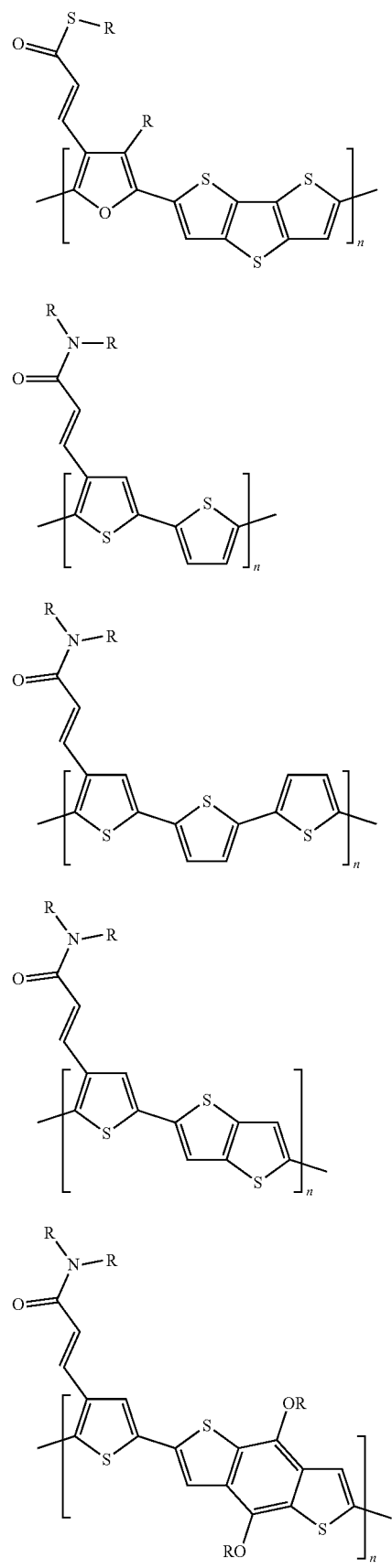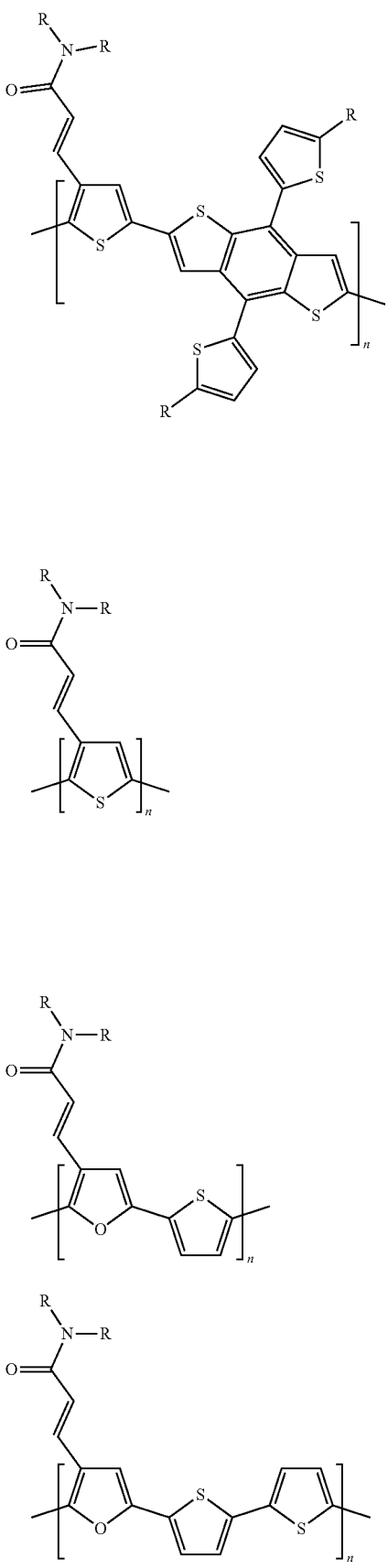

(133)
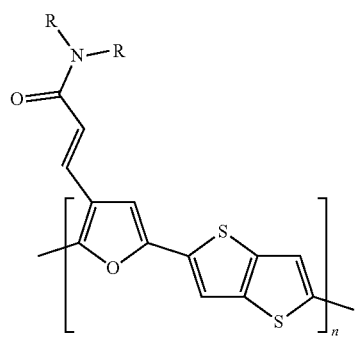
(134)
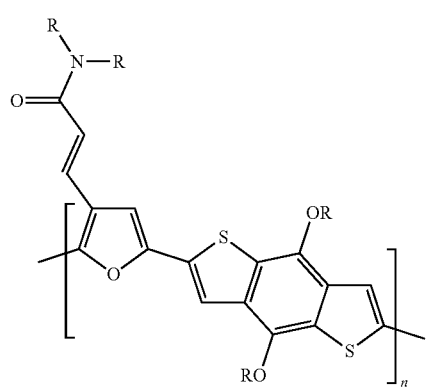
(135)
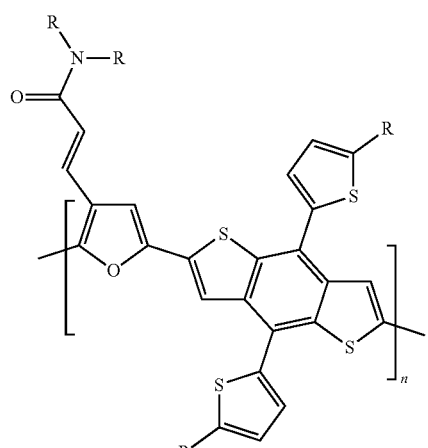
(136)
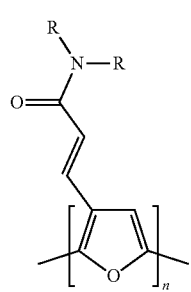
(137)
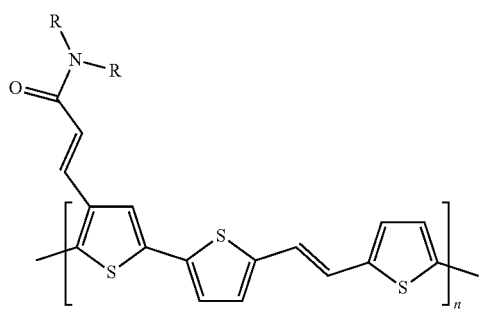
(138)
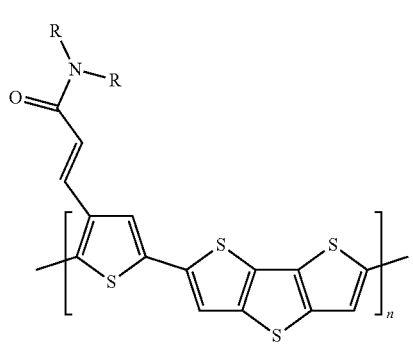
(139)
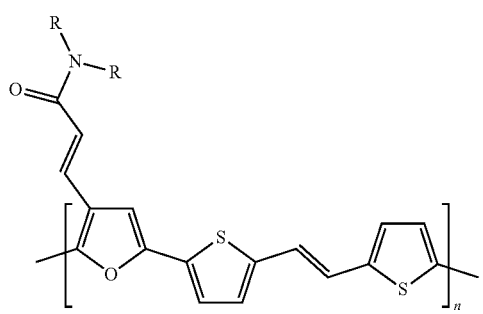
(140)
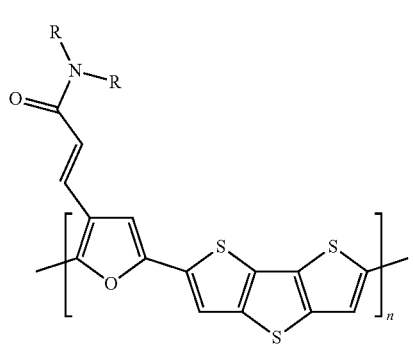
(141)
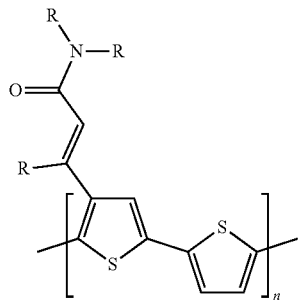

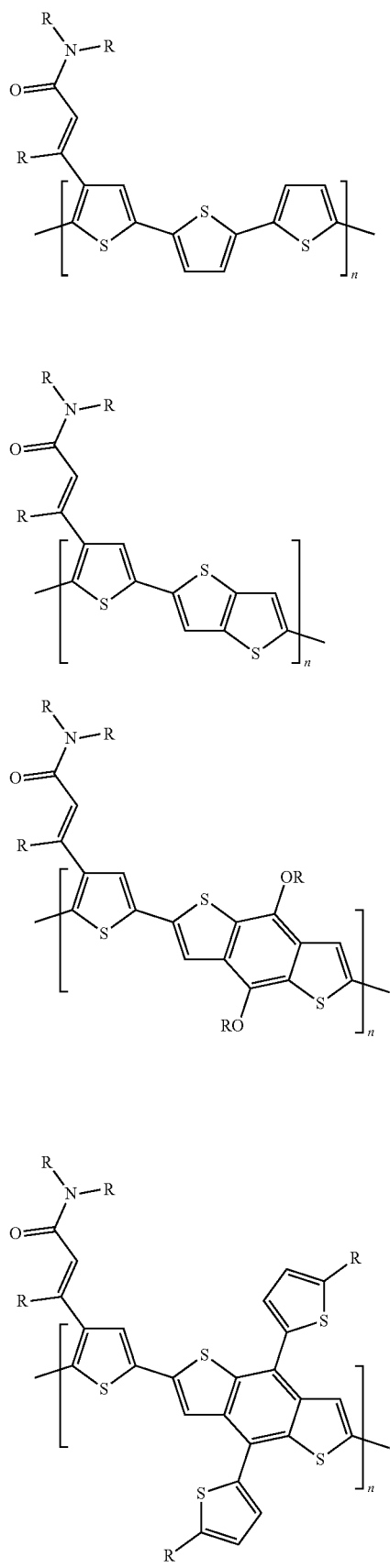
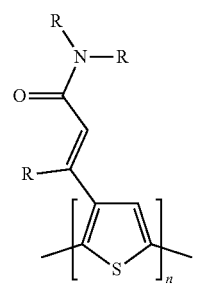
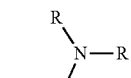
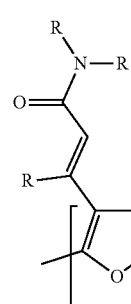
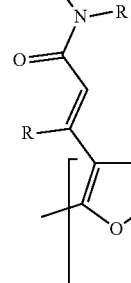
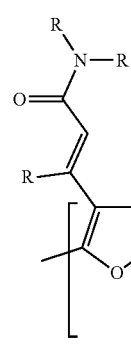

(151)
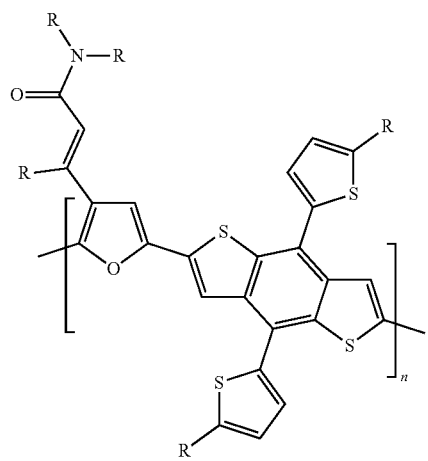
(152)
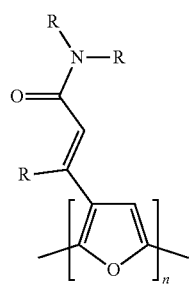
(153)
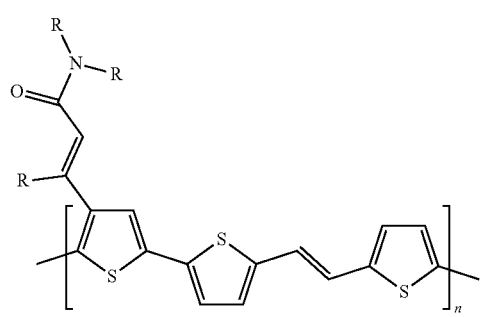
(154)
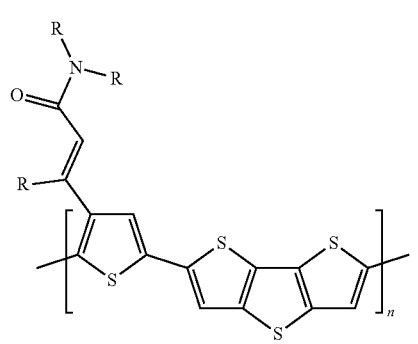
(155)
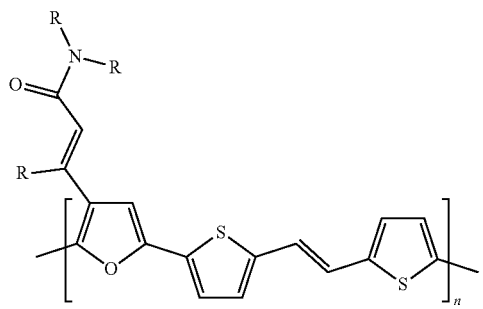
(156)
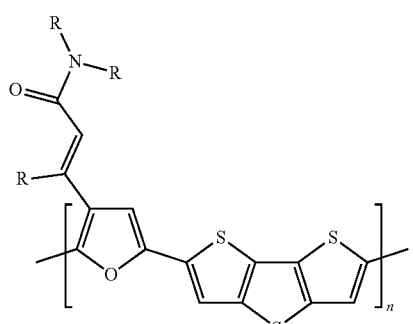
(157)
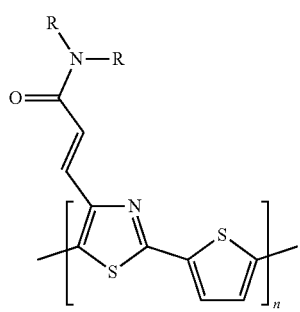
(158)
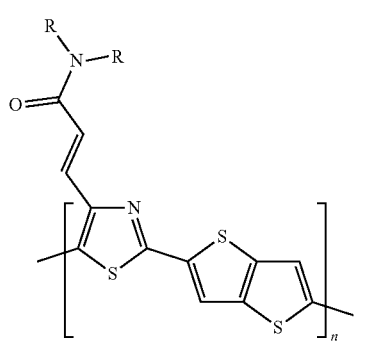
(159)
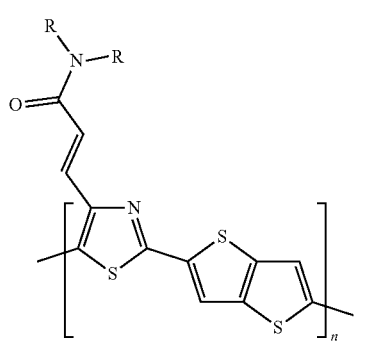

(160)
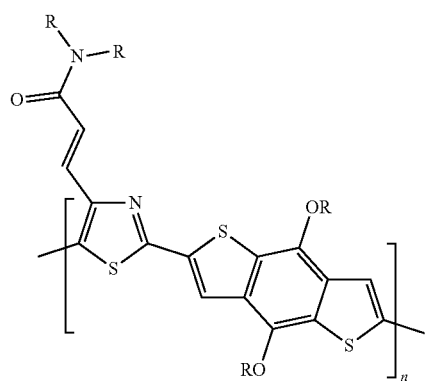
(161)
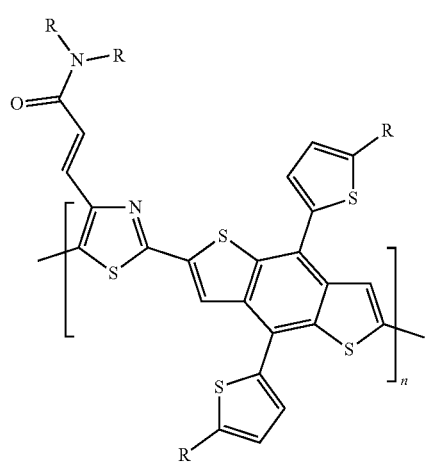
(162)
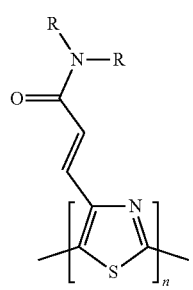
(163)
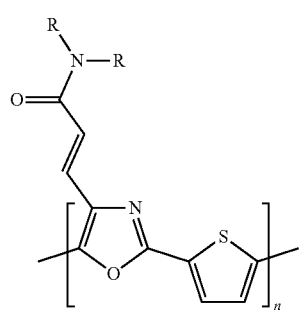
(164)
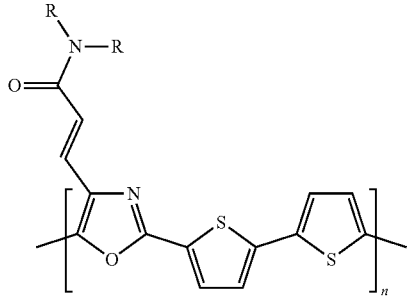
(165)
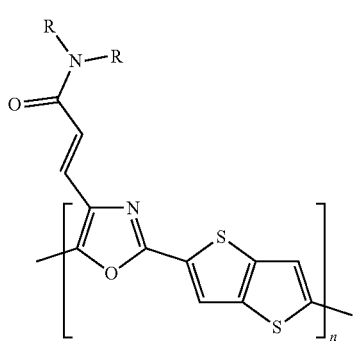
(166)
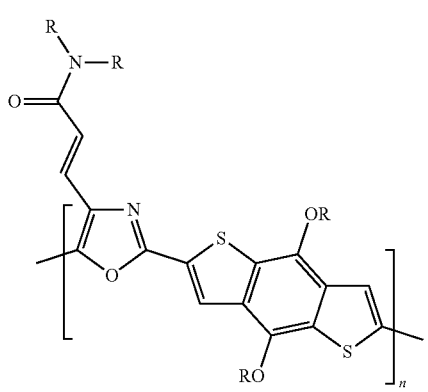
(167)
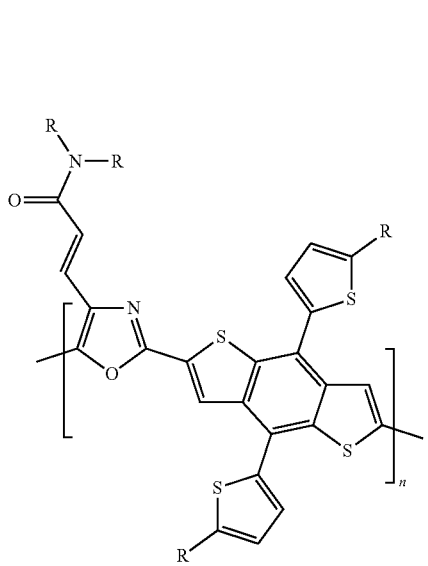

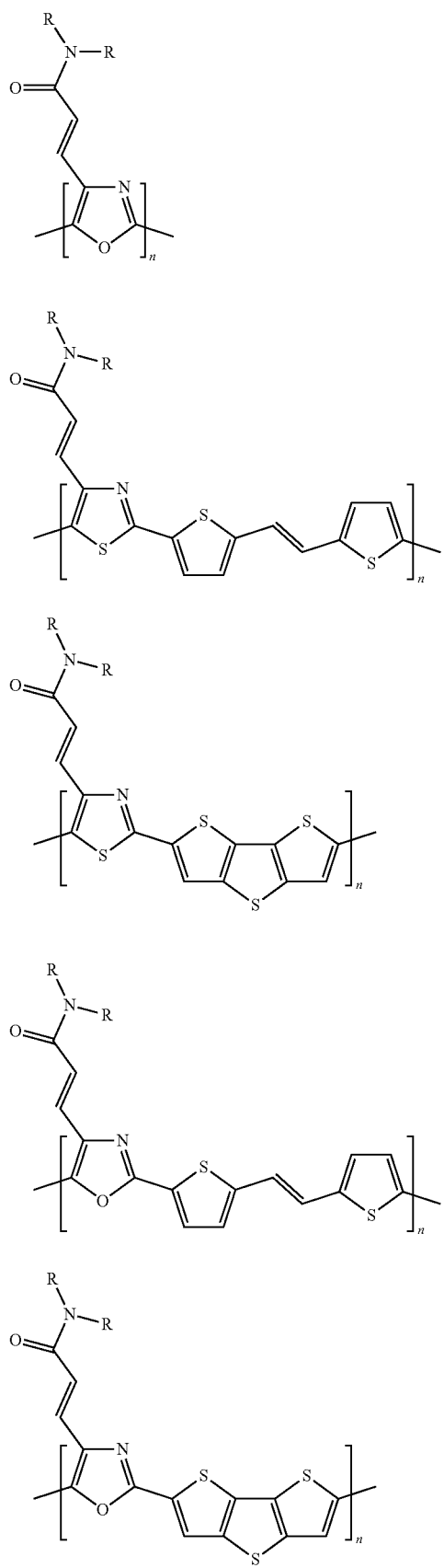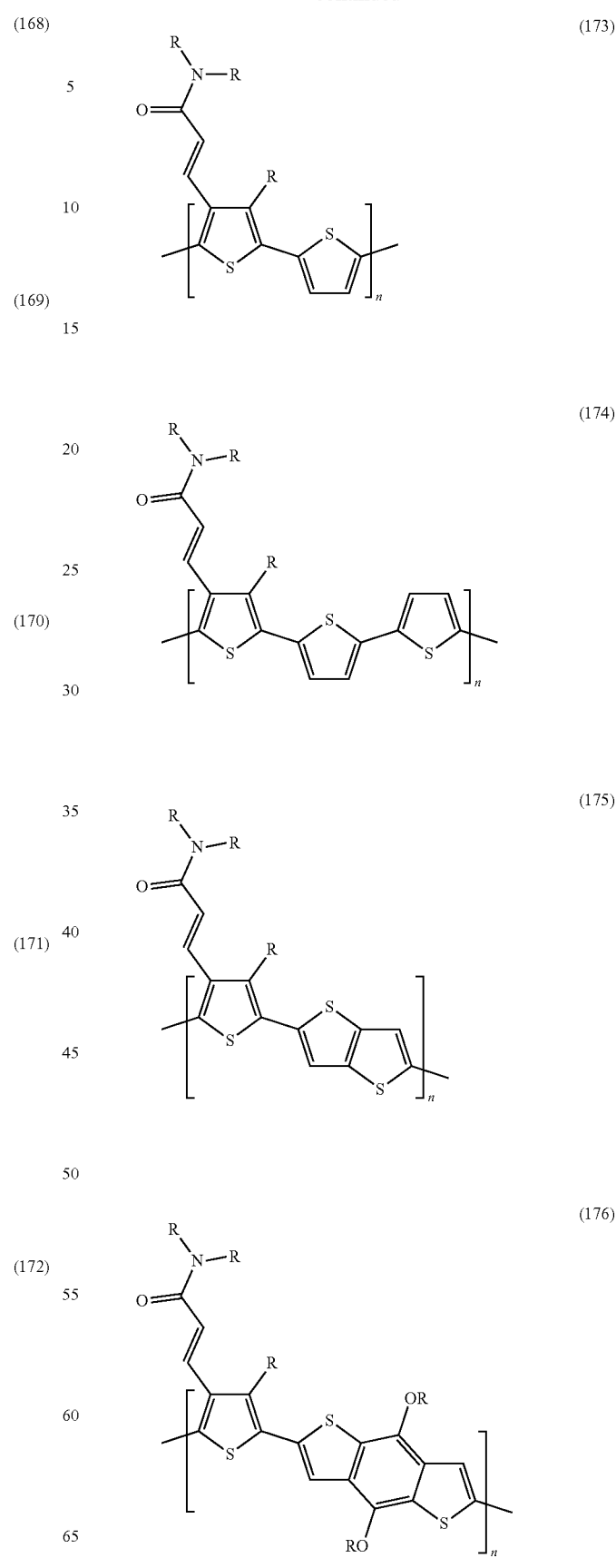

(177)
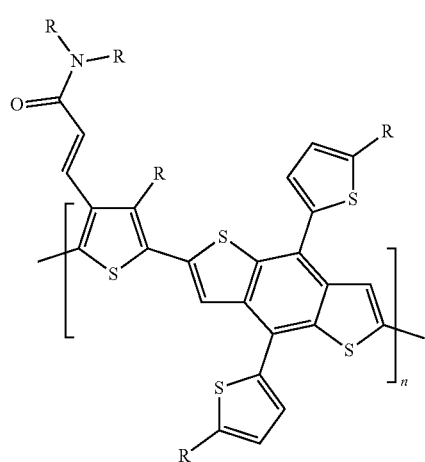
(178)
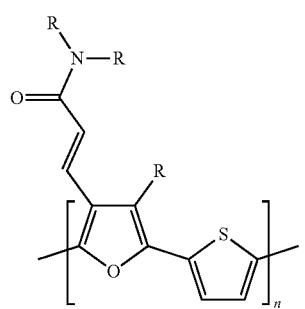
(179)
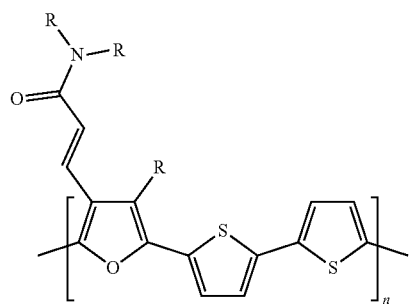
(180)
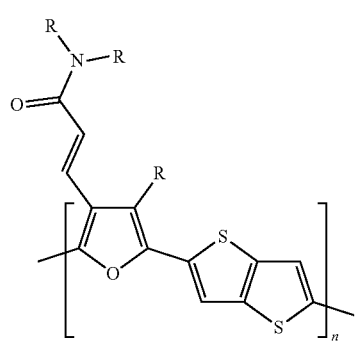
(181)
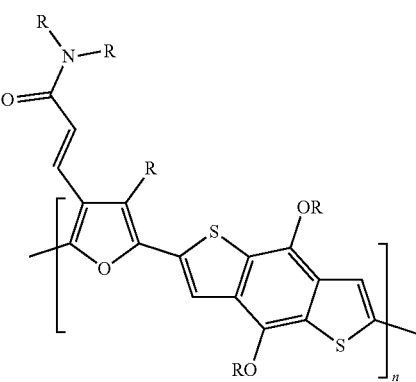
(182)
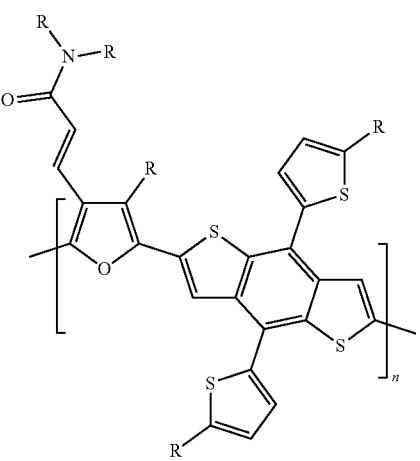
(183)
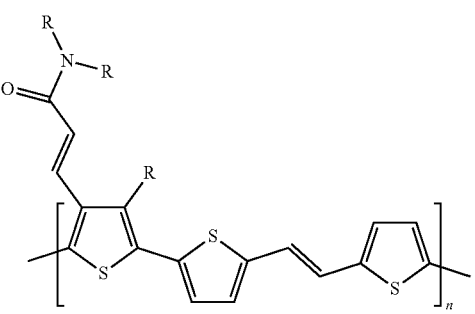
(184)
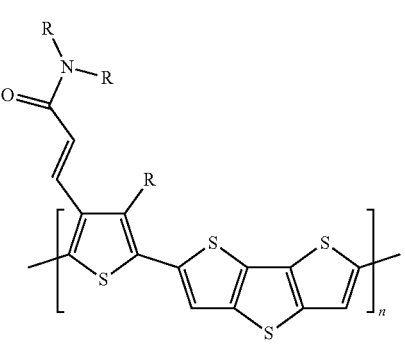

-continued

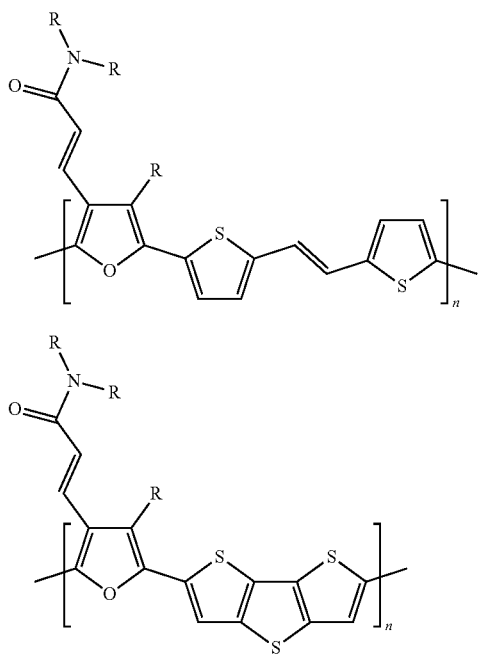

(185)

(186)

wherein:

R is independently selected from hydrogen, an optionally substituted hydrocarbon with 1 to 60 carbon atoms (such as, for example, alkyl, substituted alkyl, alkenyl, substituted alkenyl, alkynyl, substituted alkynyl, aryl, and substituted aryl), or any other suitable group;

each structure can be substituted, where is applicable, with one or more suitable groups independently selected from an optionally substituted hydrocarbon with 1 to 60 carbon atoms (such as, for example, alkyl, substituted alkyl, alkenyl, substituted alkenyl, alkynyl, substituted alkynyl, aryl, substituted aryl, alkoxy, and substituted alkoxy), cyano (CN), nitro, or halogen, or any other suitable group;

n is a number from 1 to 1,000,000;

the terminal group can be hydrogen or any other suitable group or moiety.

Compounds comprising the disclosed fused-ring moiety as defined above may preferably be selected from the group consisting of small molecules, monomers and polymers. As used herein, the term "small molecule" will be used to denote a compound comprising the fused-ring moiety and two inert chemical groups, which are inert under use condition and thus inhibit such a small molecule from being polymerized. In contrast hereto, the term "monomer" is used to denote a compound comprising said fused-ring moiety and at least one reactive chemical group, which allows such monomer to be reacted so as to form part of a polymer.

In embodiments, the monomeric, oligomeric or polymeric materials comprising moiety (I) in the present disclosure can be used in electronic devices such as, for example and without limitation, thin film transistors, photovoltaics, and sensors. The use of the present monomer, oligomer or polymer as an exemplary semiconductor in electronic devices is illustrated herein using thin film transistors (semiconductor layer in FIGS. 1-4); and as an exemplary donor-acceptor semiconductor blend layer 3 in the organic photovoltaic devices of FIGS. 5 and 6.

FIG. 1 depicts an exemplary bottom gate/top contact organic thin film transistor (OTFT) structure.

FIG. 2 depicts an exemplary bottom gate/bottom contact OTFT structure.

FIG. 3 depicts an exemplary top gate/bottom contact OTFT structure.

FIG. 4 depicts an exemplary top gate/top contact OTFT structure.

FIG. 5 depicts an exemplary organic photovoltaic device (OPV) structure where 1 is the cathode, 2 is electron transport layer, 3 is the donor-acceptor semiconductor blend layer, 4 is the hole transport layer, 5 is the transparent conductor layer, and 6 is a transparent substrate.

FIG. 6 depicts an exemplary inverted OPV structure where 1 is the cathode, 2 is electron transport layer, 3 is the donor-acceptor semiconductor blend layer, 4 is the hole transport layer, 5 is the transparent conductor layer, and 6 is a transparent substrate.

The semiconductor layer of FIGS. 1-4 has a thickness ranging for example from about 10 nanometers to about 1 micrometer with a preferred thickness of from about 20 to about 200 nanometers. The OTFT devices contain a semiconductor channel with a width, W and length, L. The semiconductor channel width may be, for example, from about 1 micrometer to about 5 millimeters, with a specific channel width being about 5 micrometers to about 1 millimeter. The semiconductor channel length may be, for example, from about 10 nanometers to about 1 millimeter with a more specific channel length being from about 20 nanometers to about 500 micrometers.

Blends, Formulations and Devices

The compounds and polymers according to the present disclosure can also be used in mixtures or polymer blends, for example together with small molecules or monomeric compounds or together with other polymers having charge-transport, semiconducting, electrically conducting, photoconducting and/or light emitting semiconducting properties, or for example with polymers having hole blocking or electron blocking properties for use as interlayers or charge blocking layers in OLED devices. Thus, another aspect of the present disclosure relates to a polymer blend comprising one or more polymers according to the present disclosure and one or more further polymers having one or more of the above-mentioned properties. In certain embodiments, these blends can be prepared by conventional methods. Typically the polymers are mixed with each other or dissolved in suitable solvents and the solutions combined.

Another aspect of the present disclosure relates to a formulation comprising one or more small molecules, polymers, mixtures or polymer blends as described above and below and one or more organic solvents.

Preferred solvents are aliphatic hydrocarbons, chlorinated hydrocarbons, aromatic hydrocarbons, ketones, ethers and mixtures thereof. Additional solvents which can be used include 1,2,4-trimethylbenzene, 1,2,3,4-tetra-methyl benzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chlorobenzotrifluoride, N,N-dimethylformamide, 2-chloro-6-fluorotoluene, 2-fluoroanisole, anisole, 2,3-dimethylpyrazine, 4-fluoroanisole, 3-fluoroanisole, 3-trifluoro-methylanisole, 2-methylanisole, phenetol, 4-methylanisole, 3-methylanisole, 4-fluoro-3-methylanisole, 2-fluorobenzonitrile, 4-fluoroveratrol, 2,6-dimethylanisole, 3-fluorobenzo-nitrile, 2,5-dimethylanisole, 2,4-dimethylanisole, benzonitrile, 3,5-dimethylanisole, N,N-dimethylaniline, ethyl benzoate, 1-fluoro-3,5-dimethoxy-benzene, 1-methylnaphthalene, N-methylpyrrolidinone, 3-fluorobenzo-trifluoride, benzotrifluoride, dioxane, trifluoromethoxy-benzene, 4-fluorobenzotrifluoride, 3-fluoropyridine, toluene, 2-fluoro-toluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluoro-benzene, 1-chloro-2,5-difluorobenzene, 4-chlorofluorobenzene, chloro-benzene, o-dichlorobenzene, 2-chlorofluorobenzene, p-xylene, m-xylene, o-xylene or mixture of o-, m-, and p-isomers. Solvents with relatively low polarity are generally preferred. For inkjet printing solvents and solvent mixtures with high boiling temperatures are preferred. For spin coating alkylated benzenes like xylene and toluene are preferred.

Examples of especially preferred solvents include, without limitation, dichloromethane, trichloromethane, chlorobenzene, o-dichlorobenzene, tetrahydrofuran, anisole, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, N,N-dimethylformamide, dimethylacetamide, dimethylsulfoxide, tetraline, decaline, indane, methyl benzoate, ethyl benzoate, mesitylene and/or mixtures thereof.

The concentration of the compounds or polymers in the solution is preferably 0.1 to 10% by weight, more preferably 0.5 to 5% by weight, with % by weight given relative to the total weight of the solution. Optionally, the solution also comprises one or more binders to adjust the rheological properties, as described for example in WO 2005/055248 A1.

After appropriate mixing and ageing, solutions can be evaluated as one of the following categories: complete solution, borderline solution or insoluble. The contour line is drawn to outline the solubility parameter-hydrogen bonding limits dividing solubility and insolubility. "Complete" solvents falling within the solubility area can be chosen from literature values such as published in J. D. Crowley et al., *Journal of Paint Technology*, 1966, 38 (496), 296. Solvent blends may also be used and can be identified as described in Solvents, W. H. Ellis, Federation of Societies for Coatings Technology, p. 9-10, 1986. Such a procedure may lead to a blend of "non"-solvents that will dissolve both the polymers of the present disclosure, although it is desirable to have at least one true solvent in a blend.

The compounds and polymers according to the present disclosure can also be used in patterned organic solar cell (OSC) layers in the devices as described above and below. For applications in modern microelectronics it is generally desirable to generate small structures or patterns to reduce cost (more devices/unit area), and power consumption. Patterning of thin layers comprising a polymer according to the present disclosure can be carried out for example by photolithography, electron beam lithography or laser patterning.

For use as thin layers in electronic or electro-optical devices, the compounds, polymers, polymer blends or formulations of the present disclosure may be deposited by any suitable method. Liquid coating of devices can be more desirable than vacuum deposition techniques. Solution deposition methods are especially preferred. The formulations of the present disclosure enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing.

Ink jet printing is particularly preferred when high resolution layers and devices need to be prepared. Selected formulations of the present disclosure may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle micro-dispensers such as those produced by Microdrop and Microfab may be used.

In order to be applied by ink jet printing or microdispensing, the compounds or polymers should be first dissolved in a suitable solvent. Solvents should fulfill the requirements stated above and generally should not have detrimental effect on the chosen print head. Additionally, solvents should have boiling points greater than 100° C., preferably greater than 140° C. and more preferably greater than 150° C. in order to prevent operability problems caused by the solution drying out inside the print head. Apart from the solvents mentioned above, suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a compound or polymer according to the present disclosure by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the compound or polymer, which reduces or prevents clogging of the jets and separation of the components during spraying. The solvent(s) may include those selected from the following list of examples: dodecylbenzene, 1-methyl-4-tert-butylbenzene, terpineol, limonene, isodurene, terpinolene, cymene, diethylbenzene. The solvent may be a solvent mixture, that is a combination of two or more solvents, each solvent preferably having a boiling point greater than 100° C., more preferably greater than 140° C. Such solvent(s) also enhance film formation in the layer deposited and reduce defects in the layer.

The ink jet fluid (that is mixture of solvent, binder and semiconducting compound) preferably has a viscosity at 20° C. of 1 to 100 mPa·s, more preferably 1 to 50 mPa·s and most preferably 1 to 30 mPa·s.

The polymer blends and formulations according to the present disclosure can additionally comprise one or more further components or additives selected for example from surface-active compounds, lubricating agents, wetting agents, dispersing agents, hydrophobing agents, adhesive agents, flow improvers, defoaming agents, deaerators, diluents which may be reactive or non-reactive, auxiliaries, colorants, dyes or pigments, sensitizers, stabilizers, nanoparticles or inhibitors.

The compounds and polymers to the present disclosure are useful as charge transport, semiconducting, electrically conducting, photoconducting or light emitting materials in optical, electrooptical, electronic, electroluminescent or photoluminescent components or devices. In these devices, the polymers of the present disclosure are typically applied as thin layers or films.

Thus, the present disclosure also provides the use of the semiconducting compound, polymer, polymers blend, formulation or layer in an electronic device. The formulation may be used as a high mobility semiconducting material in various devices and apparatus. The formulation may be used, for example, in the form of a semiconducting layer or film. Accordingly, in another aspect, the present disclosure provides a semiconducting layer for use in an electronic device, the layer comprising a compound, polymer blend or formulation according to the disclosure. The layer or film may be less than about 30 microns. For various electronic device applications, the thickness may be less than about 1 micron thick. The layer may be deposited, for example on a part of an electronic device, by any of the aforementioned solution coating or printing techniques.

The present disclosure additionally provides an electronic device comprising a compound, polymer, polymer blend, formulation or organic semiconducting layer according to the present disclosure. Preferred devices are OFETs, TFTs, ICs, logic circuits, capacitors, RFID tags, OLEDs, OLETs, OPEDs, OPVs, OPDs, solar cells, laser diodes, photoconductors, photodetectors, electrophotographic devices, electrophotographic recording devices, organic memory devices, sensor devices, charge injection layers, Schottky diodes, planarizing layers, antistatic films, conducting substrates and conducting patterns. Particularly preferred devices are OLEDs.

Especially preferred electronic device are OFETs, OLEDs, OPV and OPD devices, in particular bulk heterojunction (BHJ) OPV devices. In an OFET, for example, the active semiconductor channel between the drain and source may comprise the exemplary layer of the present disclosure. As another example, in an OLED device, the charge (hole or electron) injection or transport layer may comprise the exemplary layer of the present disclosure.

For use in OPV or OPD devices the polymer according to the present disclosure is preferably used in a formulation that comprises or contains, more preferably consists essentially of, very preferably exclusively of, a p-type (electron donor) semiconductor and an n-type (electron acceptor) semiconductor. The p-type semiconductor is constituted by a polymer according to the present disclosure. The n-type semiconductor can be an inorganic material such as zinc oxide ($ZnO_x$), zinc tin oxide (ZTO), titan oxide ($TiO_x$), molybdenum oxide ($MoO_x$), nickel oxide ($NiO_x$), or cadmium selenide (CdSe), or an organic material such as graphene or a fullerene or a substituted fullerene, for example an indene-$C_{60}$-fullerene bisadduct like ICBA, or a (6,6)-phenyl-butyric acid methyl ester derivatized methano $C_{60}$ fullerene, also known as "PCBM-$C_{60}$" or "$C_{60}$PCBM", as disclosed for example in G. Yu, J. Gao, J. C. Hummelen, F. Wudl, A. J. Heeger, Science 1995, Vol. 270, p. 1789 ff and having the structure shown below, or structural analogous compounds with e.g., a $C_{61}$ fullerene group, a $C_{70}$ fullerene group, or a $C_{71}$ fullerene group, or an organic polymer (see for example Coakley, K. M. and McGehee, M. D. Chem. Mater. 2004, 16, 4533). $C_{60}$PCBM is shown as:

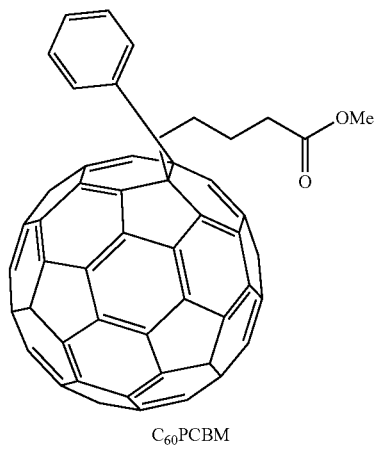 [SMILES: COC(=O)CCCCC12c3c4c5c6c7c8c9c%10c%11c%12c8c8c%13c%14c(c1c8c37)C1=CC2(c2ccccc2)C=C4CC5=CC(C=C%10CC%11=CC(C=C%14C1)C%12%13)C96]

$C_{60}$PCBM

Preferably the polymer according to the present disclosure is blended with an n-type semiconductor such as a fullerene or substituted fullerene, like for example PCBM-$C_{60}$, PCBM-$C_{70}$, PCBM-$C_{61}$, PCBM-$C_{71}$, bis-PCBM-$C_{61}$, bis-PCBM-$C_{71}$, ICMA-$c_{60}$ (1',4'-Dihydro-naphtho[2',3':1,2][5,6]fullerene-$C_{60}$), ICBA-$C_{60}$, oQDM-$C_{60}$ (1',4'-dihydro-naphtho[2',3':1,9][5,6] fullerene-$C_{60}$-Ih), bis-oQDM-$C_{60}$, graphene, or a metal oxide, like for example, $ZnO_x$, $TiO_x$, ZTO, $MoO_x$, $NiO_x$, or quantum dots like for example CdSe or CdS, to form the active layer in an OPV or OPD device. The device preferably further comprises a first transparent or semi-transparent electrode on a transparent or semi-transparent substrate on one side of the active layer, and a second metallic or semi-transparent electrode on the other side of the active layer. Further preferably the OPV or OPD device comprises, between the active layer and the first or second electrode, one or more additional buffer layers acting as hole transporting layer and/or electron blocking layer, which comprise a material such as metal oxide, like for example, ZTO, $MoO_x$, $NiO_x$, a conjugated polymer electrolyte, like for example PEDOT:PSS, a conjugated polymer, like for example polytriarylamine (PTAA), an organic compound, like for example N,N'-diphenyl-N,N'-bis(1-naphthyl)(1,1'-biphenyl)-4,4'diamine (NPB), N,N'-diphenyl-N,N'-(3-methylphenyl)-1,1'-biphenyl-4,4'-diamine (TPD), or alternatively as hole blocking layer and/or electron transporting layer, which comprise a material such as metal oxide, like for example, $ZnO_x$, $TiO_x$, a salt, like for example LiF, NaF, CsF, a conjugated polymer electrolyte, like for example poly[3-(6-trimethylammoniumhexyl)thiophena poly(9,9-bis(2-ethylhexyl)-fluorene]-b-poly[3-(6-trimethylammoniumhexyl) thiophene], or poly[(9,9-bis(3'-(N,N-dimethylamino)propyl)-2,7-fluorene)-alt-2,7-(9,9-dioctylfluorene)] or an organic compound, like for example tris(8-quinolinolato)-aluminum(III) ($Alq_3$), 4,7-diphenyl-1,10-phenanthroline.

In a blend or mixture of a polymer according to the present disclosure with a fullerene or modified fullerene, the ratio polymer:fullerene is preferably from 5:1 to 1:5 by weight, more preferably from 1:1 to 1:3 by weight, most preferably 1:1 to 1:2 by weight. A polymeric binder may also be included, from 5 to 95% by weight. Examples of binder include polystyrene (PS), polypropylene (PP) and polymethylmethacrylate (PMMA).

To produce thin layers in BHJ OPV devices the compounds, polymers, polymer blends or formulations of the present disclosure may be deposited by any suitable method. Liquid coating of devices is more desirable than vacuum deposition techniques. Solution deposition methods are especially preferred. The formulations of the present disclosure enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing. For the fabrication of OPV devices and modules area printing method compatible with flexible substrates are preferred, for example slot dye coating, spray coating and the like.

Suitable solutions or formulations containing the blend or mixture of a polymer according to the present disclosure with a $C_{60}$ or $C_{70}$ fullerene or modified fullerene like PCBM should be prepared. In the preparation of formulations, suitable solvent should be selected to ensure full dissolution of both component, p-type and n-type and take into account the boundary conditions (for example rheological properties) introduced by the chosen printing method.

Organic solvent are generally used for this purpose. Typical solvents can be aromatic solvents, halogenated solvents or chlorinated solvents, including chlorinated aromatic solvents. Examples include, but are not limited to chlorobenzene, 1,2-dichlorobenzene, chloroform, 1,2-dichloroethane, dichloromethane, carbon tetrachloride, toluene, cyclohexanone, ethylacetate, tetrahydrofuran, anisole, morpholine, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetraline, decaline, indane, methyl benzoate, ethyl benzoate, mesitylene and combinations thereof.

For use in OPV or OPD devices that comprise or contain, more preferably consists essentially of, very preferably exclusively of, a p-type (electron donor) semiconductor and an n-type (electron acceptor) semiconductor, whereas the n-type semiconductor is constituted by a polymer according to the present disclosure. The p-type semiconductor in the said OPV or OPD devices can be an organic or inorganic material. The p-type organic semiconductor material used in the disclosed OPV or OPD devices can be either small molecules or oligomers such as for example copper phthalocyanine, zinc phthalocyanine, pentacene, sexithiophenes, and any other p-type small molecule or oligomeric semiconductor (see e.g. Mishra, A. and Bäuerle, P. *Angew. Chem. Int. Ed.* 2012, 51, 2020-2067; Huang, Q. L. and Li, H. X. *Chinese Science Bulletin* 2013, 58, 2677-2686; Sun, Y., et al. *Nat Mater.* 2011, 11, 44-8; Kyaw, A. K. K., et al. *Adv. Mater.* 2013, 25, 2397-2402), and a polymer semiconductor such as for example poly(3-hexyl)thiophene and any other suitable polymer (see e.g. Thompson, B. C. and Frechet, J. M. J. *Angew. Chem. Int. Ed.* 2008, 47, 58-77; Dennler, G., et al. *Adv. Mater.* 2009, 21, 1323-1338; Cheng, Y. J., et al. *Chem. Rev.* 2009, 109, 5868-5923; Facchetti, A. *Materials Today* 2013, 16, 123-132). The p-type inorganic semiconductor material use in the said OPV or OPD devices can be p-type silicon, copper(I) sulfide ($Cu_2S$), copper(I) oxide ($Cu_2O$), copper(II) oxide (CuO), copper indium gallium selenide (CIGS), and any other suitable inorganic semiconductor. The solvents and formulation procedures that are suitable for processing OPV or OPD devices described above can also be used for the n-type semiconductor that is constituted by a polymer according to the present disclosure.

The OPV device can for example be of any type known from the literature (see e.g. Waldauf et al., *Appl. Phys. Lett.*, 2006, 89, 233517) including very preferably an OPV device where the photoactive layer comprises a p-type polymer semiconductor and an n-type polymer semiconductor (see e.g. Halls, J. J. et al. *Nature,* 1995, 376, 498-500), where the n-type polymer semiconductor is constituted by a polymer according to the present disclosure.

A first preferred OPV device according to the disclosure comprises the following layers (in the sequence from bottom to top):

optionally a substrate, a high work function electrode, preferably comprising a metal oxide, like for example indium tin oxide (ITO), serving as anode, an optional conducting polymer layer or hole transport layer, preferably comprising an organic polymer or polymer blend, for example of PEDOT:PSS (poly(3,4-ethylenedioxythiophene): poly(styrene-sulfonate), or TBD (N,N'-dyphenyl-N—N'-bis(3-methylphenyl)-1,1'biphenyl-4,4'-diamine) or NBD (N,N'-dyphenyl-N—N'-bis(1-napthylphenyl)-1,1'biphenyl-4,4'-diamine), a layer, also referred to as "active layer", comprising a p-type and an n-type organic semiconductor, which can exist for example as a p-type/n-type bilayer or as distinct p-type and n-type layers, or as blend or p-type and n-type semiconductor, forming a bulk heterojunction (BHJ), optionally a layer having electron transport properties, for example comprising LiF, a low work function electrode, preferably comprising a metal like for example aluminum, serving as cathode, wherein at least one of the electrodes, preferably the anode, is transparent to visible light, and wherein the n-type semiconductor is a polymer according to the present disclosure.

A second preferred OPV device according to the disclosure is an inverted OPV device and comprises the following layers (in the sequence from bottom to top):

optionally a substrate, a high work function metal or metal oxide electrode, comprising for example ITO, serving as cathode, a layer having hole blocking properties, preferably comprising a metal oxide like $TiO_x$ or $Zn_x$, an active layer comprising a p-type and an n-type organic semiconductor, situated between the electrodes, which can exist for example as a p-type/n-type bilayer or as distinct p-type and n-type layers, or as blend or p-type and n-type semiconductor, forming a BHJ, an optional conducting polymer layer or hole transport layer, preferably comprising an organic polymer or polymer blend, for example of PEDOT:PSS or TBD or NBD, an electrode comprising a high work function metal like for example silver, serving as anode, wherein at least one of the electrodes, preferably the cathode, is transparent to visible light, and wherein the n-type semiconductor is a polymer according to the present disclosure.

When the active layer is deposited on the substrate, it forms a BHJ that phase separates at nanoscale level. For discussion on nanoscale phase separation see Dennler et al, *Proceedings of the IEEE,* 2005, 93 (8), 1429 or Hoppe et al, *Adv. Func. Mater,* 2004, 14(10), 1005. An optional annealing step may be then necessary to optimize blend morphology and consequently OPV device performance.

Another method to optimize device performance is to prepare formulations for the fabrication of OPV(BHJ) devices that may include high boiling point additives to promote phase separation in the right way. 1,8-Octanedithiol, 1,8-diiodooctane, nitrobenzene, chloronaphthalene, and other additives have been used to obtain high-efficiency solar cells. Examples are disclosed in J. Peet, et al, *Nat. Mater.*, 2007, 6, 497 or Fréchet et al. *J. Am. Chem. Soc.*, 2010, 132, 7595-7597.

The compounds, polymers, formulations and layers of the present disclosure are also suitable for use in an OFET as the semiconducting channel. Accordingly, the present disclosure also provides an OFET comprising a gate electrode, an insulating (or gate insulator) layer, a source electrode, a drain electrode and an organic semiconducting channel connecting the source and drain electrodes, wherein the organic semiconducting channel comprises a compound, polymer, polymer blend, formulation or organic semiconducting layer according to the present disclosure. Other features of the OFET are well known to those skilled in the art.

OFETs where an OSC material is arranged as a thin film between a gate dielectric and a drain and a source electrode, are generally known, and are described for example in U.S. Pat. Nos. 5,892,244, 5,998,804, 6,723,394 and in the references cited in the background section. Due to the advantages, like low cost production using the solubility properties of the compounds according to the disclosure and thus the processibility of large surfaces, preferred applications of these FETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present disclosure preferably comprises:
a source electrode,
a drain electrode,
a gate electrode,
a semiconducting layer,
one or more gate insulator layers, and
optionally a substrate,
wherein the semiconductor layer preferably comprises a compound, polymer, polymer blend or formulation as described above and below.

The OFET device can be a top gate device or a bottom gate device. Suitable structures and manufacturing methods of an OFET device are known to the skilled in the art and are described in the literature, for example in US 2007/0102696 A1.

The gate insulator layer preferably comprises a fluoropolymer, like e.g., the commercially available Cytop 809M® or Cytop 107M® (from Asahi Glass). Preferably the gate insulator layer is deposited, e.g., by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g., FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377). Especially preferred are organic dielectric materials having a low permittivity (or dielectric constant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present disclosure, like transistors or diodes, can be used for RFID tags or security markings to authenticate and prevent counterfeiting of documents of value like banknotes, credit cards or ID cards, national ID documents, licenses or any product with monetary value, like stamps, tickets, shares, checks, etc.

Alternatively, the materials according to the disclosure can be used in OLEDs, e.g., as the active display material in a flat panel display applications, or as backlight of a flat panel display like e.g., a liquid crystal display. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The exemplary compounds, materials and films may be employed in one or more of the charge transport layers and/or in the emission layer, corresponding to their electrical and/or optical properties. Furthermore their use within the emission layer is especially advantageous, if the compounds, materials and films according to the disclosure show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Müller et al, *Synth. Metals*, 2000, 111-112, 31-34, Alcala, *J. Appl. Phys.*, 2000, 88, 7124-7128 and the literature cited therein.

According to another use, the materials according to this disclosure, especially those showing photoluminescent properties, may be employed as materials of light sources, e.g. in display devices, as described in EP 0 889 350 A1 or by C. Weder et al., *Science*, 1998, 279, 835-837.

A further aspect of the disclosure relates to both the oxidized and reduced form of the compounds according to this disclosure. Either loss or gain of electrons results in formation of a highly delocalized ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalized ionic centers in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantation of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4\text{-}CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)(SbF_6^-)$, $(NO_2^+)(SbCl_6^-)$, $(NO_2^+)(BF_4^-)$, $AgClO_4$, $H_2IrCl_6$, $La(NO_3)_3 \cdot 6H_2O$, $FSO_2OOSO_2F$, europium acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds of the present disclosure can be used as an organic "metal" in applications including, but not limited to, charge injection layers and ITO planarizing layers in OLED applications, films for flat panel displays and touch screens, antistatic films, printed conductive substrates, patterns or tracts in electronic applications such as printed circuit boards and condensers.

The compounds and formulations according to the present disclosure may also be suitable for use in organic plasmon-emitting diodes (OPEDs), as described for example in Koller et al., *Nat. Photonics*, 2008, 2, 684.

According to another use, the materials according to the present disclosure can be used alone or together with other materials in or as alignment layers in LCD or OLED devices, as described for example in US 2003/0021913. The use of charge transport compounds according to the present disclosure can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarization charge of the ferroelectric LCs. When used in an OLED device comprising a light emitting material provided onto the alignment layer, this increased electrical conductivity can enhance the electroluminescence of the light emitting material. The compounds or materials according to the present disclosure having mesogenic or liquid crystalline properties can form oriented anisotropic films as described above, which are especially useful as alignment layers to induce or enhance alignment in a liquid crystal medium provided onto said anisotropic film. The materials according to the present disclosure may also be combined with photoisomerizable compounds and/or chromophores for use in or as photoalignment layers, as described in US 2003/0021913 A1.

According to another use, the materials according to the present disclosure, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, *Proc. Natl. Acad. Sci. U.S.A.*, 1999, 96, 12287; D. Wang, X. Gong, P. S. Heeger, F. Rininsland, G. C. Bazan and A. J. Heeger, *Proc. Natl. Acad. Sci. U.S.A.*, 2002, 99, 49; N. DiCesare, M. R. Pinot, K. S. Schanze and J. R. Lakowicz, *Langmuir*, 2002, 18, 7785; D. T. McQuade, A. E. Pullen, T. M. Swager, *Chem. Rev.*, 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

Above and below, unless stated otherwise percentages are percent by weight and temperatures are given in degrees Celsius. The values of the dielectric constant ("permittivity") refer to values taken at 20° C. and 1,000 Hz.

The present disclosure will now be described in detail with respect to specific representative examples/embodiments thereof, it being understood that these examples are intended to be illustrative only and the present disclosure is not intended to be limited to the examples, materials, conditions, or process parameters recited herein. The following examples are merely illustrative of the materials, systems, methods, assemblies and devices disclosed herein and are not intended to limit the scope hereof.

Exemplary Embodiments

Exemplary embodiments of methods according to the present disclosure as well as reactants and further processes that may be used are described below.

The synthesis of exemplary polymers PTAT-R, PTABT-R, and PTATT-R is outlined in Scheme 1.

Scheme 1. The synthetic route to PTAT-R, PTATT-R, and PTABT-R.

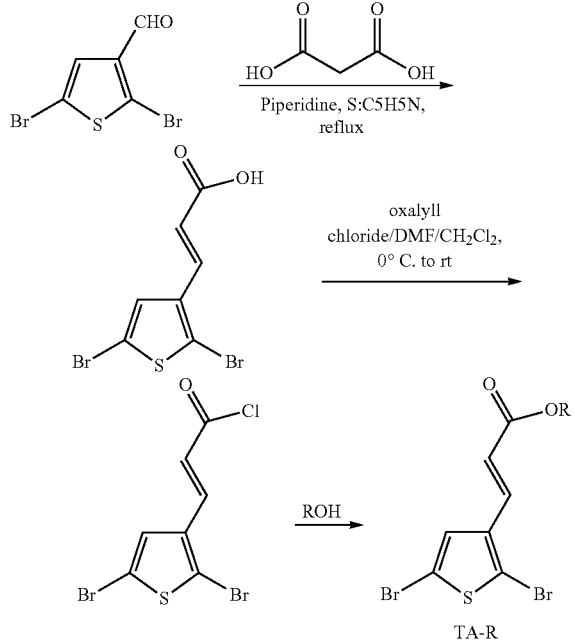

-continued

R:

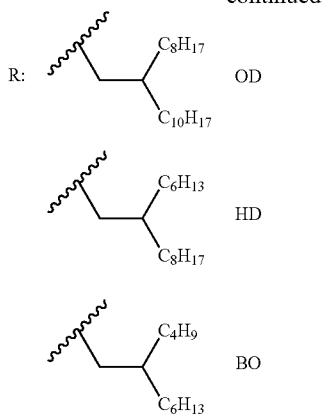

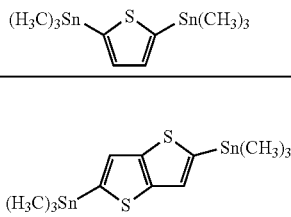

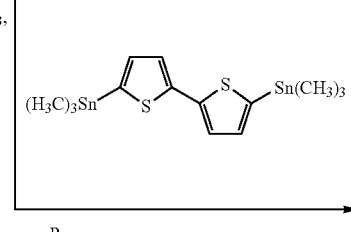

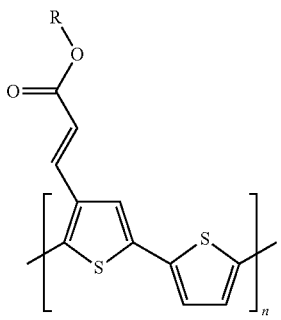

PTAT-R

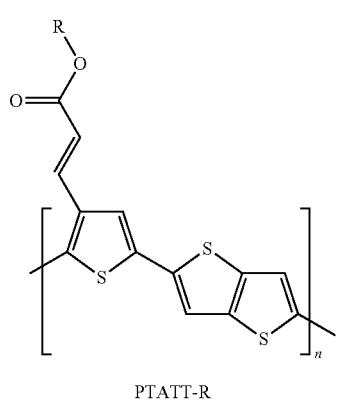

PTATT-R

-continued

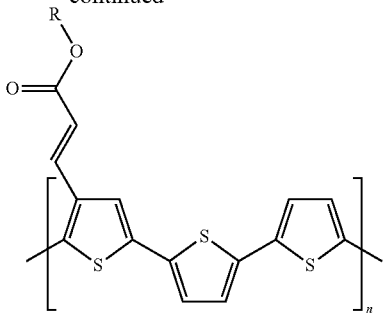

PTABT-R

EXAMPLES

Example 1

Synthesis of (E)-3-(2,5-dibromothiophen-3-yl)acrylic acid

A mixture of 2,5-dibromothiophene-3-carbaldehyde (57 mmol), malonic acid (74.1 mmol) and piperidine (0.85 mL, 8.6 mmol) in pyridine (50 mL) was heated under reflux for 18 hours. The reaction mixture was cooled to room temperature, poured in to ice-water and acidified with HCl(aq). The crude product was filtered and washed with cold water to yield the product as a white solid.

Example 2

Synthesis of alkyl (E)-3-(2,5-dibromothiophen-3-yl) acrylate (TA-R)

Oxalyl chloride (15.543 g, 120 mmol) was slowly added to a stirred mixture of (E)-3-(2,5-dibromothiophen-3-yl) acrylic acid (60 mmol) and N,N-dimethylformamide (2-3 drops) in dry $CH_2Cl_2$ (90 mL) at 0° C. under nitrogen. The reaction mixture was stirred at room temperature for an additional 2 to 5 hours and evaporated to dryness to give the corresponding acid chloride (E)-3-(2,5-dibromothiophen-3-yl)acryloyl chloride in a quantitative yield. Then, a solution of (E)-3-(2,5-dibromothiophen-3-yl)acryloyl chloride in dry $CH_2Cl_2$ (100 mL) was slowly added to a stirred solution of alcohol (60 mmol) and pyridine (4.986 mL, 62.4 mmol) in dry $CH_2Cl_2$ (100 mL) at 0° C. The reaction mixture was then stirred at room temperature for 24 hours, water was added (50 mL), the mixture was left at room temperature for 3 hours, the organic phase was separated, dried over anhydrous sodium sulfate, and evaporated to dryness to give the product TA-R.

Example 3

Synthesis of PTAT-R

A 25-mL dry two-neck round bottom flask equipped with a water condenser was charged with TA-R (0.177 mmol, 1.0 equiv.), 2,5-bis(trimethylstannyl)thiophene (0.177 mmol, 73 mg, 1.0 equiv.) and tri(o-tolyl)phosphine (P(o-tol)$_3$) (4.31 mg, 14.2 µmol, 0.08 equiv). Anhydrous chlorobenzene (5 mL) was injected through a septum, and a solution of tris(dibenzylideneacetone)dipalladium (Pd$_2$(dba)$_3$) (3.24 mg, 3.54 µmol, 0.02 equiv.) in chlorobenzene was added with a syringe. The reaction mixture was then heated at 90° C. under argon atmosphere for 24 hours. 2-Bromobenzene (0.5 mL) was added to react with the residual trimethylstannyl end group for 2 hours. After cooled down to 50° C., Pyridine (0.5 mL) was added to neutralize the mixture for 1 hours. After cooling down to room temperature, the mixture was poured into a stirring methanol (150 mL). The solid was collected by filtration, washed with acetone, dried and further purified through Soxhlet extraction using acetone, hexane, and chloroform. The polymer was obtained by precipitation of chloroform solution into methanol.

Example 4

Synthesis of PTATT-R

This polymer was synthesized using TA-R (0.177 mmol, 1.0 equiv.) and 2,5-bis(trimethylstannyl)thieno[3,2-b]thiophene (0.177 mmol, 82 mg, 1.0 equiv.) following the similar procedure the synthesis of PTAT-R in Example 3.

Example 5

Synthesis of PTABT-R

This polymer was synthesized using TA-R (0.177 mmol, 1.0 equiv.), and 5,5'-bis(trimethylstannyl)-2,2'-bithiophene (0.177 mmol, 87 mg, 1.0 equiv.) following the similar procedure the synthesis of PTAT-R in Example 3.

Example 6

Characterization of Polymers

The UV-Vis-IR absorption spectra of polymers were recorded on a Thermo Scientific model GENESYS™ 10S VIS spectrophotometer. Cyclic voltammetry (CV) data were obtained on a CHI600E electrochemical analyser using an Ag/AgCl reference electrode and two Pt disk electrodes as the working and counter electrodes in a 0.1 M tetrabutylammonium hexafluorophosphate solution in acetonitrile at a scan rate of 100 mV s$^{-1}$. Ferrocene was used as the reference, which has a HOMO energy value of −4.8 eV.

Example 7

Fabrication and Characterization of OTFT Devices

A bottom-contact, bottom-gate OTFT configuration was used. Heavily p-doped Si wafer functions as the gate electrode and a thermally grown $SiO_2$ layer (around 200 nm) with a capacitance of around 17 nF/cm$^2$ on top of the Si layer was used as the insulating dielectric. Gold source and drain electrode pairs were pre-deposited on the $SiO_2$ layer with the common photolithography method. The substrate was cleaned with DI water, acetone, and isopropanol in an ultrasonic bath, followed by $O_2$ plasma. Subsequently, the substrate was immerged in a dodecyltrichlorosilane (DTS) solution in toluene (10 mg/cm$^3$) at 70° C. for 20 minutes. After washing with toluene, the substrate was dried under a nitrogen flow. A polymer solution in chloroform (10 mg/cm$^3$) was spin coated on the substrate at 3000 rpm for 60 seconds to give a film, which was subject to thermal annealing at different temperature for 15 minutes in a glove box. OTFT devices have a channel length (L) of 30 μm and a channel width (W) of 1000 μm. The devices were characterized in air using an Agilent 4155C Semiconductor Analyzer. The carrier mobility in the saturated regime, $\mu_{sat}$, was calculated according to the equation of $I_{DS}=C_i\mu_{sat}(W/2L)(V_G-V_T)^2$, where $I_{DS}$ is the drain current, $C_i$ is the capacitance per unit area of the gate dielectric, W and L are, respectively, the semiconductor channel width and length, and $V_G$ and $V_T$ are, respectively, the gate voltage and threshold voltage. $V_T$ of the devices was determined from extrapolation of the linear fit of the $(I_{DS})^{1/2}$ versus $V_G$ curve in the saturation regime at $I_{DS}=0$.

Example 8

Fabrication and Characterization of OPV Devices

The OPV devices were fabricated in a standard device architecture with the following structure: ITO/PEDOT:PSS/donor:acceptor/LiF/Al. First, the ITO glass substrates were cleaned by sonication in DI water, acetone and isopropanol successively. Then the substrates were further cleaned in a plasma cleaner. A layer (around 40 nm) PEDOT:PSS was spin-coated onto the ITO substrates using the Al 4083 PEDOT:PSS dispersion. The substrates were then dried on a hotplate at 145° C. for 20 minutes. An active layer (around 110 nm) was spin-coated onto of the PEDOT:PSS using a solution of donor polymer:acceptor (ITIC) in chlorobenzene (CB) (12 mg mL$^{-1}$, 1:1 weight ratio). The resultant films were dried in the vacuum for 60 minutes before a layer of LiF (around 1 nm) and a layer of Al (around 100 nm) were thermal deposited onto the substrates to give the solar cell devices. The devices were characterized under 100 mW cm$^{-2}$ AM 1.5 G illumination conditions.

Example 9

Achieving Over 10% Efficiency in Organic Solar Cells Via Substituents Design

A side chain modified wide-bandgap polymer donor, PBDTTh-TA, was synthesized to blend with a narrow-bandgap non-fullerene acceptor (NFA), ITIC, in bulk heterojunction (BHJ) organic solar cell devices to obtain a complementary absorption and effectively utilize sunlight in wide wavelength range from 340 to 800 nm. Compared to a reported reference polymer donor, PBDTTh-TC, an addition of a double bond between thiophene and an ester group in PBDTTh-TA showed improved photovoltaic performance when it was blended with ITIC in o-DCB solvent. An organic solar cell device based on PBDTTh-TA:ITIC achieved a high power conversion efficiency (PCE) of 10.47%, with an open-circuit voltage ($V_{oc}$) of 0.96 V, a short-circuit current density ($J_{sc}$) of 19.43 mA/cm$^2$, and a fill factor (FF) of 0.56. In comparison, PBDTTh-TC was also used in a device under the same fabrication conditions and a PCE of 9.68% was achieved. In addition, a non-halogenated solvent xylene was used to fabricate PBDTTh-TA:ITIC device, which maintained a PCE of 9.76%. It was shown that the introduction of a double bond in PBDTTh-TC can improve the photovoltaic performance by improving the donor acceptor interaction.

Solar cell technology, which converts sunlight into electricity, is one of the most compelling technologies that utilizes renewable solar energy to meet the ever-increasing energy demand sustainably. Although traditional solar cells based on inorganic semiconductor materials such as silicon have been commercialized, their applications have been greatly limited due to their complex production processes, high costs, poor degradability of inorganic materials and/or the difficulty of flexible processing. In recent years, organic solar cells (OSCs) have attracted widespread attention due to their low cost, good processing performance, light weight, flexibility, and/or large-area printing production. In terms of the photovoltaic performance, the power conversion efficiency (PCE) has reached 18.22% recently. However, compared with the silicon based inorganic solar cells, the PCEs of some organic solar cells can be low. One of the main technologies to improve PCEs of solar cells is improve the absorption of the active layer to gain more sunlight energy during absorption. In exemplary embodiments, the present disclosure starts from a polymer donor achieving a PCE close to 10% in organic solar cell devices, to further design the structure in order to improve PCE.

PBDTTh-TC (also known as 3MT-Th), whose structure is shown below, is a donor used recently with performance because of its strong absorption. It has been reported to use 3MT-Th in organic solar cells which reached a PCE of 9.73%. The influence of the distance between thiophene and the ester side chain was investigated. The present disclosure provides a new polymer by adding a double bonding between these two groups, as well as PBDTTh-TC for comparison. The chemical geometry and electron distribution were simulated for both polymers, and it showed a smaller dihedral angle (36.81°) for PBDTTh-TA while the dihedral angle of PBDTTh-TC was 49.44°. That suggests adding doubling bond may reduce a steric hindrance effect of the ester group, and influence the intermolecular packing in the polymer thin film. Thus, PBDTTh-TA should have better π-π stacking and better mobility in the organic solar cells compared to PBDTTh-TC. The simulation also showed the molecular orbital energy levels and electron distributions for both polymers.

The theoretical (highest occupied molecular orbital) HOMO/LUMO (lowest unoccupied molecular orbital) energy levels were investigated to be −5.16/−1.97 eV for BDTTh-TA-1, −5.21/−1.81 eV for BDTTh-TA-2, −5.20/−1.74 eV for BDTTh-TC-1 and −5.18/−1.78 eV for BDTTh-TC-2, respectively. The HOMO electron distribution was more delocalized through the whole polymer backbone in PBDTTh-TA rather than the distribution in PBDTTh-TC, and the LUMO electron distribution was more delocalized around acceptor unit in PBDTTh-TA rather than the distribution in PBDTTh-TC. The results suggest that introducing a doubling bond will result in down-shifted LUMO levels and up-shifted HOMO levels, which should provide a smaller bandgap. Compared with PBDTTh-TC, a similar HOMO level of PBDTTh-TA is expected to have similar $V_{OC}$ in organic solar cell devices.

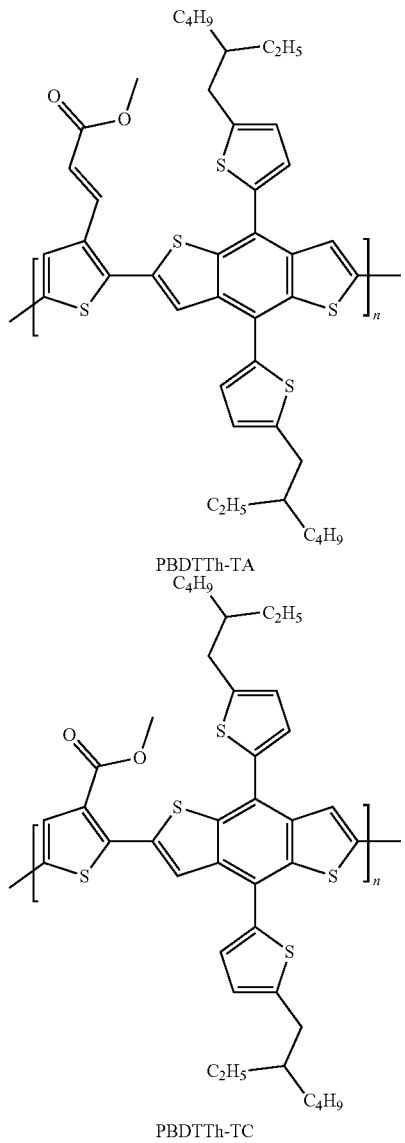

PBDTTh-TA

PBDTTh-TC

Synthesis and Characterization of Polymers:

The target polymers were prepared via Stille coupling polymerization. The polymerization afforded PBDTTh-TA in a 98% yield. Under the same reaction conditions, PBDTTh-TC was prepared in a 99% yield. The scheme and more detailed descriptions about the synthesis of the monomers and polymers and molecular weight are provided below.

The optical properties of both PBDTTh-TA and PBDTTh-TC were measured by UV-Vis spectroscopy. Above all, each polymer was dissolved in chloroform to prepare a solution with the concentration of 5 mg/mL. Then, the thin films were prepared by spin coating. The UV-Vis absorptions of diluted solution, thin film and annealed thin film were measured, and the results of thin films are shown in FIG. 7. The maximum absorptions of PBDTTh-TA and PBDTTh-TC in solution were observed at 517 nm and 510 nm. The polymer films at room temperature exhibited absorption maxima at 539 nm and 526 nm for PBDTTh-TA and PBDTTh-TC, respectively. After the thin films were annealed at 100° C. for 20 minutes, the maximum absorption peaks were shown at 541 nm and 528 nm for PBDTTh-TA and PBDTTh-TC, respectively. The data clearly demonstrates that by adding a double bonding between the thiophene and the ester group can result in a red shift of maximum absorption. The maximum absorption peak of PBDTTh-TA with a red shift would be caused by the addition of double bond which improves the planarity of the polymer backbone.

As for electrical properties, a great difference was observed between PBDTTh-TA and PBDTTh-TC. Cyclic voltammetry (CV) was used to investigate the oxidations and reductions for the polymers, and the results are shown in FIG. 8. The polymer films exhibited oxidation onsets at 0.67 V and 0.81 V for PBDTTh-TA and PBDTTh-TC, respectively. Both polymers showed no obvious reduction peaks during the CV measurements.

Based on the measurements, the basic properties of PBDTTh-TA and PBDTTh-TC were obtained, and they are shown in Table 1 below. The HOMO and LUMO levels were estimated to be −5.47 eV and −3.47 eV for PBDTTh-TA and −5.61 eV and −3.58 eV for PBDTTh-TC, respectively.

TABLE 1

Basic properties of PBDTTh-TA and PBDTTh-TC:

| Compound | $\lambda_{max}^{abs}$ Solution | $\lambda_{max}^{abs}$ Film | $E_g$ (Optical) | HOMO | LUMO |
|---|---|---|---|---|---|
| PBDTTh-TA | 517 nm | 539 nm | 2.00 eV | −5.47 eV | −3.47 eV |
| PBDTTh-TC | 510 nm | 526 nm | 2.03 eV | −5.61 eV | −3.58 eV |

Meanwhile, the organic field-effect transistor (OTFT) performances were investigated for both polymers. The average mobilities of PBDTTh-TA and PBDTTh-TC are very close; however, PBDTTh-TA polymer has a higher average threshold voltage, which means the current will be consumed more when switching the state of devices. FIGS. 9A and 9B show the transfer and output curves for the prepared OTFT devices of PBDTTh-TA, and the Table 2 shows the OTFT performance properties of PBDTTh-TA. The best mobility of PBDTTh-TA occurs at 100° C. and is $3.01 \times 10^{-3}$ cm$^2$V$^{-1}$s$^{-1}$. The average mobility is $2.67 \times 10^{-3}$ cm$^2$V$^{-1}$s$^{-1}$ with −31.29 V of average threshold voltage.

TABLE 2

OTFT performance properties of PBDTTh-TA:

| Temperature (° C.) | Best mobility (cm$^2$V$^{-1}$s$^{-1}$) | Avg mobility (cm$^2$V$^{-1}$s$^{-1}$) | Avg $I_{on}/I_{off}$ | Avg Vth (V) |
|---|---|---|---|---|
| RT | $2.06 \times 10^{-3}$ | $1.87 \times 10^{-3} \pm 1.42 \times 10^{-4}$ | 2800 | −25.79 ± 1.43 |
| 50 | $2.71 \times 10^{-3}$ | $2.22 \times 10^{-3} \pm 2.98 \times 10^{-4}$ | 4600 | −31.45 ± 4.38 |
| 100 | $3.01 \times 10^{-3}$ | $2.67 \times 10^{-3} \pm 2.35 \times 10^{-4}$ | 8200 | −31.29 ± 4.35 |
| 150 | $2.73 \times 10^{-3}$ | $2.61 \times 10^{-3} \pm 1.07 \times 10^{-4}$ | 6400 | −24.47 ± 3.10 |
| 200 | $2.49 \times 10^{-3}$ | $2.32 \times 10^{-3} \pm 1.05 \times 10^{-4}$ | 6400 | −27.51 ± 3.94 |

For the comparison, the OTFT performance of PBDTTh-TC was also determined by the semiconductor analyzer. FIGS. 10A and 10B show the power transfer (PT) and power output (PO) characteristics of OTFT devices of PBDTTh-TC, and Table 3 gives the OTFT performances under different temperatures. The best mobility of PBDTTh-TC occurs at 150° C. and is $2.83 \times 10^{-3}$ cm$^2$V$^{-1}$s$^{-1}$. The average mobility is $2.62 \times 10^{-3}$ cm$^2$V$^{-1}$s$^{-1}$ with −1.95 V of average threshold voltage.

TABLE 3

OTFT performance properties of PBDTTh-TC:

| Temperature (° C.) | Best mobility (cm$^2$V$^{-1}$s$^{-1}$) | Avg mobility (cm$^2$V$^{-1}$s$^{-1}$) | Avg $I_{on}/I_{off}$ | Avg Vth (V) |
|---|---|---|---|---|
| RT | $2.41 \times 10^{-3}$ | $2.30 \times 10^{-3} \pm 1.10 \times 10^{-4}$ | 2800 | 1.89 ± 1.24 |
| 50 | $2.34 \times 10^{-3}$ | $2.27 \times 10^{-3} \pm 0.93 \times 10^{-4}$ | 2800 | −3.60 ± 4.18 |
| 100 | $2.78 \times 10^{-3}$ | $2.26 \times 10^{-3} \pm 0.54 \times 10^{-4}$ | 2800 | −13.38 ± 10.29 |
| 150 | $2.83 \times 10^{-3}$ | $2.62 \times 10^{-3} \pm 2.32 \times 10^{-4}$ | 3250 | −1.95 ± 3.08 |
| 200 | $2.64 \times 10^{-3}$ | $2.44 \times 10^{-3} \pm 0.28 \times 10^{-4}$ | 5500 | −9.57 ± 3.12 |

The photovoltaic properties of the side chain modified polymer PBDTTh-TA were investigated in devices with an inverted structure of ITO/ZnO (35 nm)/active layer/MoO$_3$ (10 nm)/Ag (100 nm). The active layer was composed of polymer donor PBDTTh-TA (or reference PBDTTh-TC) and a non-fullerene acceptor (ITIC). Active-layer blend concentration, spin-coating rate, thermal annealing, and additives were systematically screened, and the corresponding photovoltaic parameters are presented in Tables 4 to 7, below.

TABLE 4

Summary of the photovoltaic properties of the PBDTTh-TA:ITIC devices processed at different RPMs at annealing temperature of 130° C.:

| RPM | Solvent | $J_{sc}$ (mA/cm$^2$) | $V_{oc}$ (V) | FF | PCE (%) |
|---|---|---|---|---|---|
| 600 | CB | −16.64 | 0.98 | 0.58 | 9.44 |
| 1000 | CB | −13.56 | 0.98 | 0.55 | 7.38 |

TABLE 5

Summary of the photovoltaic properties of the PBDTTh-TA:ITIC devices processed with different annealing temperatures and solvents for 10 min and 600 RPM:

| Annealing temperature | Solvent | $J_{sc}$ (mA/cm$^2$) | $V_{oc}$ (V) | FF | PCE (%) |
|---|---|---|---|---|---|
| RT | CB | −17.49 | 0.99 | 0.45 | 7.74 |
| 100 | CB | −16.88 | 0.98 | 0.56 | 9.22 |
| 130 | CB | −16.64 | 0.98 | 0.58 | 9.44 |
| 150 | DCB | −19.01 | 0.99 | 0.52 | 9.72 |
| 130 | DCB | −19.43 | 0.96 | 0.56 | 10.47 |

TABLE 6

Summary of the photovoltaic properties of the PBDTTh-TA:ITIC devices processed with different solvents at annealing temperature of 130° C. and 600 RPM:

| Solvent | $J_{sc}$ (mA/cm$^2$) | $V_{oc}$ (V) | FF | PCE (%) |
|---|---|---|---|---|
| DCB | −19.43 | 0.96 | 0.56 | 10.47 |
| CB | −20.34 | 0.97 | 0.52 | 10.19 |
| Xylene | −19.63 | 0.98 | 0.51 | 9.76 |
| CF | −18.89 | 1.00 | 0.47 | 8.90 |

TABLE 7

Summary of the photovoltaic properties of the devices processed with various additives at annealing temperature of 130° C. and 600 RPM:

| Additives | Solvent | $J_{sc}$ (mA/cm$^2$) | $V_{oc}$ (V) | FF | PCE (%) |
|---|---|---|---|---|---|
| DIO [0.5% v/v] | DCB | −15.71 | 0.99 | 0.43 | 6.69 |
| CN [0.5% v/v] | DCB | −17.39 | 0.98 | 0.55 | 9.39 |

TABLE 7-continued

Summary of the photovoltaic properties of the devices processed with various additives at annealing temperature of 130° C. and 600 RPM:

| Additives | Solvent | $J_{sc}$ (mA/cm$^2$) | $V_{oc}$ (V) | FF | PCE (%) |
|---|---|---|---|---|---|
| DIO [0.25% v/v] | DCB | −16.29 | 0.99 | 0.57 | 9.22 |
| CN [0.25% v/v] | DCB | −16.9 | 0.99 | 0.55 | 9.22 |

The optimized active-layer thickness of around 120 nm (corresponding to 600 RPM in o-DCB solvent) and optimum annealing temperature of 130° C. resulted in the highest PCE of 10.47% with an open-circuit voltage ($V_{oc}$) of 0.96 V, short-circuit current density ($J_{sc}$) of 19.43 mA/cm$^2$, and fill factor (FF) of 0.56. For the reference polymer PBDTTh-TC, the same optimized conditions were used, which resulted in a PCE of 9.68% with an open-circuit voltage ($V_{oc}$) of 0.96 V, short-circuit current density ($J_{sc}$) of 18.23 mA/cm$^2$, and fill factor (FF) of 0.55, which is as par with the best reported values of this polymer (3MT-Th: 9.73%) and (ran-PThE: 8.68%). The current density-voltage (J-V) and normalized external quantum efficiency (EQE) curves of the devices are displayed in FIGS. 11A and 11B.

It was hoped that the HOMO level of PBDTTh-TA compared to that of the reference PBDTTh-TC polymer would result in a higher Voc. However, the same $V_{oc}$ obtained (0.96 V) in both the polymer systems also means the same energy loss in PBDTTh-TA polymer of 0.66 eV (the energy loss for polymer:NFA system, $E_{loss}$ is defined as $E_{loss}=E_{gap}/q-V_{oc}$, where $E_{gap}$ is the lowest optical bandgap among the donor and acceptor components and q is the elementary charge). The improved performance of the PBDTTh-TA-based devices is ascribed to the increased $J_{sc}$ values (as can be seen from FIG. 11A and Table 8), despite lower HOMO and LUMO offset between the donor and the acceptor. Several systems with efficient charge separation despite low offsets have been reported recently and the efficiency of charge separation has been attributed to achieving an intermixed and optimized active layer morphology (characterized by PL quenching efficiency measurement).

The wavelength dependent origin of increased $J_{sc}$ can be seen in the EQE-wavelength spectrum (FIG. 11B) where PBDTTh-TA showed more pronounced EQE values in the lower wavelength region (around 400 nm) and near the ITIC absorption peak (around 700 nm). Moreover, both the donor polymers provide broader EQE spectrum from 350 to 800 nm, implying both donor and acceptor contributing to the current. The achieved $J_{sc}$ of 19.43 mA/cm$^2$ is higher than previously reported high performance OSCs with ITIC as acceptor (see Table 9 for list of high PCE BHJ solar cell employing ITIC as acceptor).

TABLE 8

Photovoltaic parameters of PBDTTh-TA:ITIC and PBDTTh-TA:ITIC:

| Active layer | Solvent | $J_{sc}$ (mA/cm$^2$) | $V_{oc}$ (V) | FF | PCE (%) |
|---|---|---|---|---|---|
| PBDTTh-TA:ITIC | DCB | 19.43 | 0.96 | 0.56 | 10.47 |
| PBDTTh-TA:ITIC | Xylene | 19.63 | 0.98 | 0.51 | 9.76 |
| PBDTTh-TC:ITIC | DCB | 18.23 | 0.96 | 0.55 | 9.68 |

TABLE 9

Photovoltaic data from literature for high PCE solar cells employing ITIC as acceptor:

| | D:A | Jsc (mA/cm$^2$) | Voc (V) | FF | PCE (%) | Extra treatment |
|---|---|---|---|---|---|---|
| Above 10% | | | | | | |
| J71:ITIC | 1:1 | 17.32 | 0.94 | 0.70 | 11.41 | NA |
| PBDBT:ITIC | 1:1 | 16.81 | 0.90 | 0.74 | 11.21 | 0.5 DIO |
| PFBZ:ITIC | 1:1.25 | 18.80 | 0.89 | 0.62 | 10.40 | NA |
| PTZ6:ITIC | 1:1 | 14.10 | 1.01 | 0.72 | 10.30 | 1.5 DIO |
| PBQ-TF:ITIC | 1:1 | 17.87 | 0.95 | 0.67 | 11.34 | 5 IPA [THF] |
| PTzBI:ITIC | 1:1 | 18.29 | 0.87 | 0.64 | 10.24 | 0.5 DBE |
| PFB-DBT:ITIC | 1:1.25 | 18.50 | 0.95 | 0.66 | 11.71 | NA |
| J61:ITIC | 1:1 | 17.97 | 0.90 | 0.65 | 10.57 | NA |
| m-PBDTPS-FTAZ:ITIC | 1:1 | 18.76 | 0.95 | 0.74 | 13.16 | NA |
| PDCBT:ITIC | 1:1 | 16.50 | 0.94 | 0.66 | 10.16 | NA |
| Below 10% | | | | | | |
| PTB7-Th:ITIC | 1:1.5 | 13.11 | 0.81 | 0.59 | 6.28 | NA |
| PTPD3T:ITIC | 1:1 | 13.54 | 0.92 | 0.68 | 8.43 | NA |
| HD-PBDT2FT:ITIC | 1:1 | 14.40 | 0.92 | 0.65 | 8.70 | 0.2 DIO |
| J61:ITIC | 1:1 | 17.43 | 0.89 | 0.61 | 9.53 | NA |

To further investigate the cause for enhanced Jsc of the PBDTTh-TA:ITIC devices compared to the reference devices, photoluminescence quenching experiments were carried out to characterize the effectiveness of exciton diffusion and charge transfer from donor to acceptor phase of the BHJ active layer. As shown in FIGS. 12A and 12B, the donors and ITIC neat films show photoluminescence (PL) emission in the regions of 600-750 and 750-850 nm, respectively. In both the PBDTTh-TC:ITIC and PBDTTh-TA:ITIC blends, effective quenching of donor PL was observed in their respective films, suggesting a highly efficient exciton diffusion from the donor phase to the donor-acceptor interface and subsequent photoinduced charge transfer from donor to acceptor (an efficient channel I photocurrent contribution by electron transfer from donor to acceptor). However, the acceptor PL quenching (contributing to channel II photocurrent by hole transfer from acceptor to donor) was slightly less efficient (around 92%) in the PBDTTh-TC:ITIC blend as compared to the same in the PBDTTh-TA:ITIC blend (around 95%). The improved quenching can be used to explain the corresponding improved photocurrent and enhanced donor-acceptor interaction ($J_{sc}$).

The hole and electron mobilities of the blend films were measured by the space charge limited current (SCLC) method using the device structures of ITO/PEDOT:PSS (30 nm)/active layer/MoO$_x$ (10 nm)/Ag (100 nm) and ITO/ZnO (35 nm)/active layer/LiF (1 nm)/Al (100 nm), respectively. As shown in Table 10, the calculated electron and hole mobilities of PBDTTh-TA:ITIC devices were 8.68×10$^{-5}$ and 2.00×10$^{-4}$ cm$^2$ V$^{-1}$ s$^{-1}$ (corresponding to hole to electron ratio, $\mu_h/\mu_e$=2.30), respectively. In comparison, the reported values of both the electron and hole mobilities of reference PBDTTh-TC:ITIC based devices were lower that of PBDTTh-TA:ITIC devices (see Table 10). The higher carrier mobility can further explain the improved J$_{sc}$ of PBDTTh-TA:ITIC based devices compared with the reference PBDTTh-TC devices.

TABLE 10

SCLC data:

| | Electron mobility [cm$^2$ V$^{-1}$ s$^{-1}$] | | Hole mobility [cm$^2$ V$^{-1}$ s$^{-1}$] | |
|---|---|---|---|---|
| | Maximum | Average [SD] | Maximum | Average [SD] |
| PBDTTh-TA neat | — | — | 8.12 × 10$^{-4}$ | 6.13 × 10$^{-4}$ [1.57 × 10$^{-5}$] |
| PBDTTh-TA:ITIC | 1.11 × 10$^{-4}$ | 8.68 × 10$^{-5}$ [1.51 × 10$^{-5}$] | 2.17 × 10$^{-4}$ | 2.00 × 10$^{-4}$ [1.90 × 10$^{-5}$] |
| PBDTTh-TC:ITIC | — | 5.24 × 10$^{-5}$ | — | 5.76 × 10$^{-5}$ |
| PBDTTh-TC:ITIC | — | 5.98 × 10$^{-5}$ | — | 4.21 × 10$^{-5}$ |
| ITIC neat | 3.0 × 10$^{-4}$ | 2.6 × 10$^{-4}$ | — | — |

SD: standard deviation from min 4 devices

Furthermore, to prove the suitability of non-halogenated solvents in soluble device processing, the devices using a non-halogenated solvent xylene were fabricated. The detailed photovoltaic data obtained from the green solvent processed devices are also presented in Table 8, which maintained a high PCE of 9.76%, promising for eco-friendly large-scale production and commercialization prospects.

Surface morphology of the PBDTTh-TA:ITIC device was characterized using AFM. A smooth film with RMS roughness of 1.02 nm suggested an intermixed morphology, which might explain substantial reduction in the blend SCLC electron and hole mobilities as compared to the neat film mobilities (see Table 10; PBDTTh-TA: 6.13×10$^{-4}$ and ITIC: 2.60×10$^{-4}$ cm$^2$ V$^{-1}$ s$^{-1}$). To obtain information about ordering and packing in thin films, grazing incidence XRD of neat and blend films were also measured (FIGS. 13A-13D). In neat film, weak intensity from both lamellar and π-π stacking at 2theta values of 4.97° (lamellar spacing: 1.77 nm) and 24.54° (π-π packing distance: 0.36 nm). However, in the blend film, none of the peaks could be seen, suggesting that the blend is mostly amorphous in nature, which would be the prominent reason for lowered mobilities in the blend.

Since stability of materials is important along with high PCE for a successful transition from lab to large scale fabrication, the long-term stability of the best performance device based on PBDTTh-TA:ITIC device was assessed in an unencapsulated device under ambient conditions. After 200 hours, the unencapsulated devices in the ambient (RH around 55-60% and temperature around 22-24° C.) retained around 88% of the initial PCE (Table 11), suggesting good stability. FF was the major contributor to the decreased PCE, which can be expected due to degradation of the interface between the blend film and top contact (MoO$_3$/Ag electrode) by the moisture and oxygen in the atmosphere.

TABLE 11

Stability data of PBDTTh-TA:ITIC device:

| | Jsc (mA/cm2) | Voc (V) | FF | PCE (%) |
|---|---|---|---|---|
| Initial | −19.43 | 0.96 | 0.56 | 10.47 |
| Shelf storage-200 hrs | −18.57 | 0.95 | 0.52 | 9.20 |

In summary, PBDTTh-TA was designed and synthesized, which has an addition of a double bond between the ester group and thiophene compared with PBDTTh-TC reported before with a PCE of 9.73%. The hypothesis that a larger separation distance of the ester group, which acts as an acceptor unit, from the polymer backbone can reduce the electron trapping effect, was strongly supported by the data above. This results in a higher PCE of 10.47% achieved in the donor-acceptor architectures of OSC devices, with a good ambient stability. In addition, a non-halogenated solvent xylene was used to replace chlorinated solvent DCB during the process, and a PCE of 9.76% can be achieved. All in all, introduction of a double bond in the substituent can be a promising method to counter the steric hindrance effect and can be used for modification of polymer donor to construct a high-performance OSC device, due to improved donor-acceptor interaction resulting in improved short circuit current density.

Density Functional Theory:

Density functional theory was calculated by Software GaussView 5.0, and calculations at the B3LYP/6-31G (d,p) level were carried out to investigate the structure geometries, molecular levels and electron distributions. To simplify the calculations, the alkyl chains were replaced with methyl chains and one repeating unit was used in the calculations.

Synthesis:

All regents and solvents used for the synthesis section were purchased from Sigma-Aldrich and Tokyo Chemical Industry. The polymers PBDTTh-TA and PBDTTh-TC were synthesized via Scheme 2, below. 1H NMR and 13C NMR were measured for intermediates and monomers by a Bruker 300 NMR spectrometer. UV-vis spectra were investigated in dilute chloroform solution (0.0375 mg/mL) as well as thin film on the glass. Polymer thin films were prepared on the glass substrates by using spin coating (2000 rpm for 60 seconds) by using 5 mg/mL chloroform solution. Cyclic voltammogram was recorded on CHI660 electrochemical workstation. The number-average (Mn) and weight-average (Mw) molecular weights were measured by high temperature gel permeation chromatography (GPC) using a calibration curve of polystyrene standards and chlorobenzene as an eluent. Organic thin film transistor (OTFT) performances were determined by Agilent 4155C Semiconductor Analyzer.

Scheme 2—Synthesis of PBDTTh-TA and PBDTTh-TC:
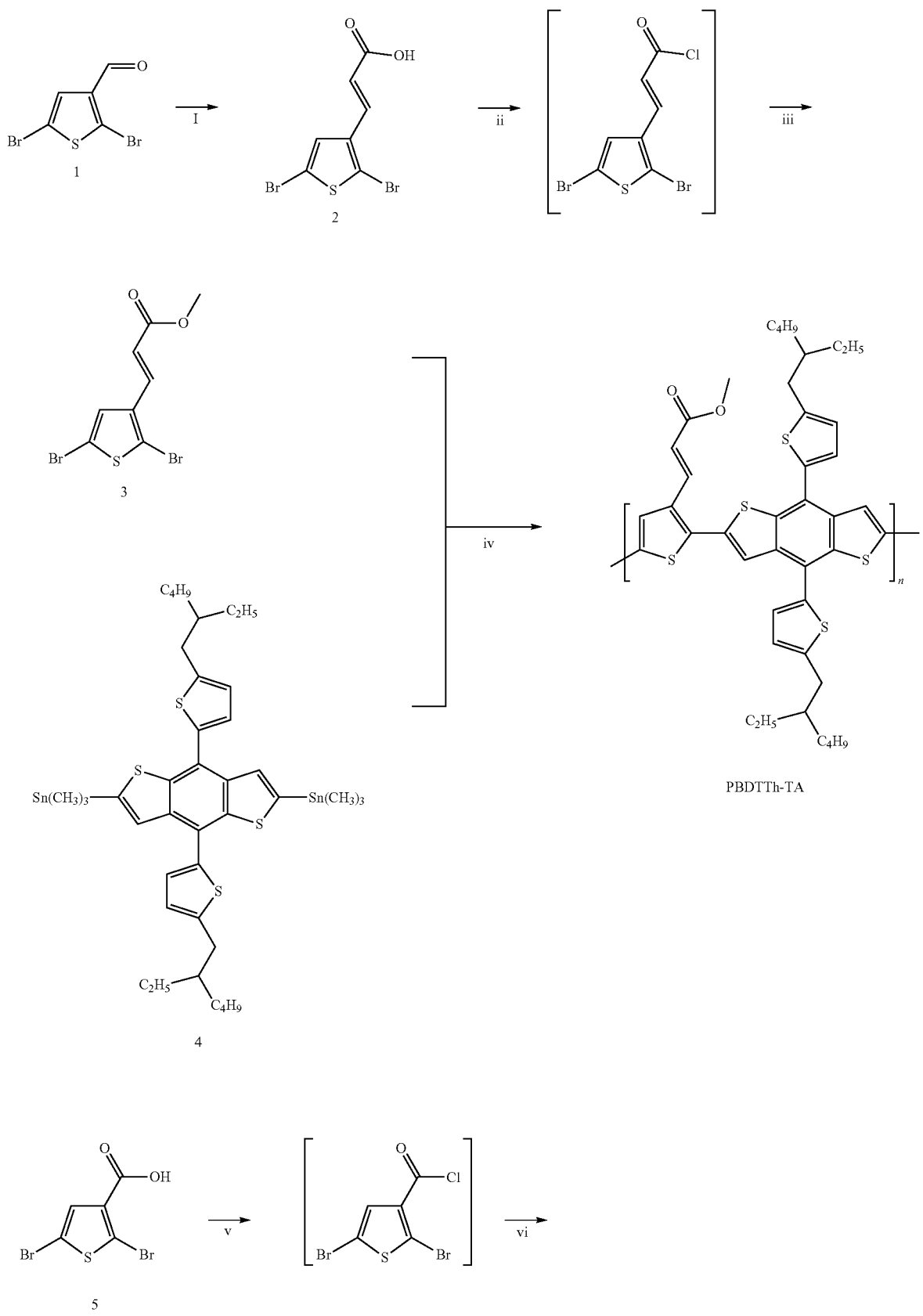

-continued

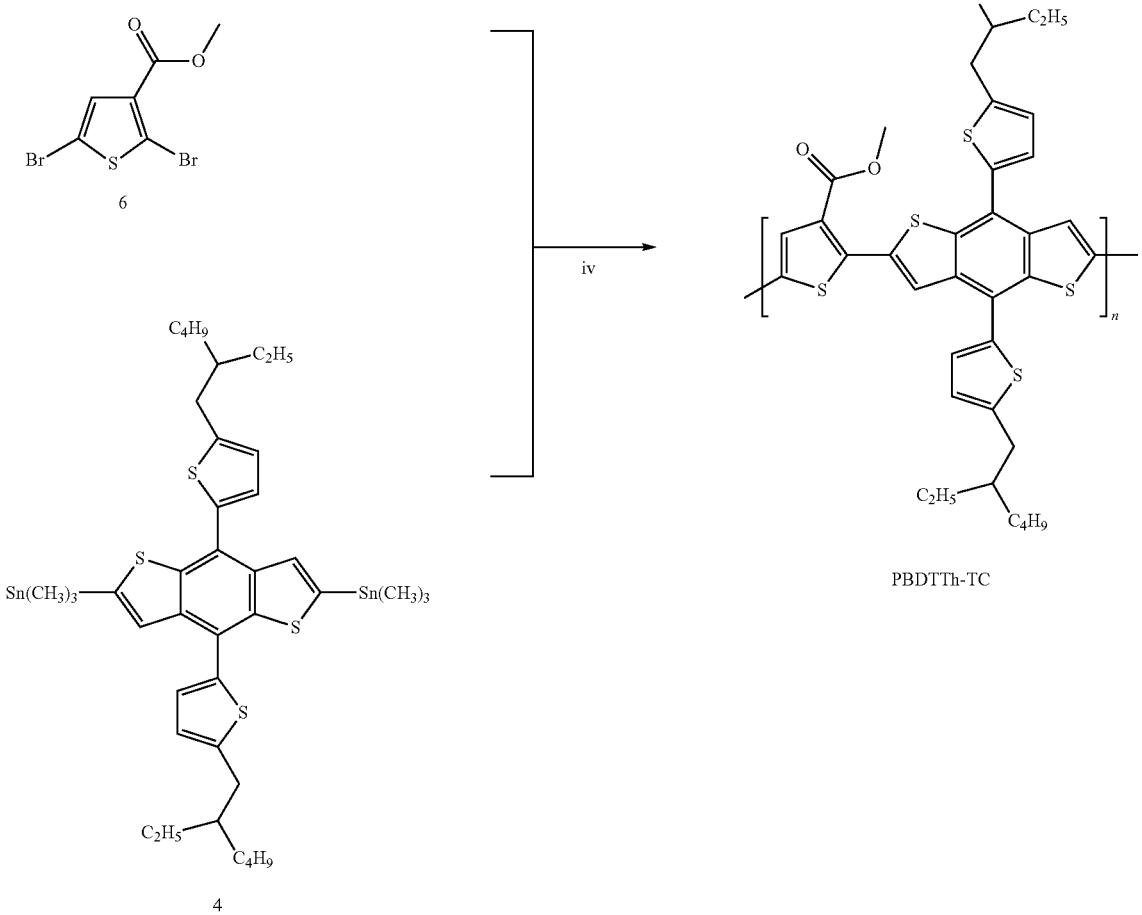

Synthesis of Monomers and Polymers:

(E)-3-(2,5-dibromothiophen-3-yl) acrylic acid (2)

2,5-dibromothiophene-3-carbaldehyde (1.74 g, 6.4106 mmol), malonic acid (0.86 g, 8.3338 mmol) were dissolved in pyridine (6 mL) and piperidine (0.1 mL, 0.9672 mmol) was added. Then, the mixture was refluxed for 18 hours. After the reaction mixture was cooled to room temperature, it was poured into ice-water and was acidified with HCl (aq). Then the mixture was filtered and was washed with chloroform to yield "2" from Scheme 2 (1.67 g, 84%) as a white solid.

$^1$H NMR (300 MHz, DMSO): δ=12.62 (s, 1H), 7.77 (s, 1H), 7.31-7.37 (d, J=18 Hz, 1H), 6.50-6.55 (d, J=15 Hz, 1H).
$^{13}$C NMR (300 MHz, DMSO): δ=167.80, 137.53, 133.96, 129.57, 122.82, 116.03, 112.79.

Methyl (E)-3-(2,5-dibromothiophen-3-yl) acrylate (3)

A solution of "2" from Scheme 2 (0.4 g, 1.2821 mmol) in anhydrous chloroform (2.5 mL) was put into an oven dried 3-neck round bottom flask under nitrogen, and then the solution was cooled to 0° C. by using an ice bath. Oxalyl chloride (0.12 mL, 1.4103 mmol) was added dropwise using a dropping funnel, followed with dimethylformamide (0.1 mL) as a catalyst. After the addition of oxalyl chloride, the reaction was allowed to warm to room temperature for 4 hours. Unreacted oxalyl chloride was removed under reduced pressure and a glass vacuum trap in a bath of mixture of acetone and dry ice (−78° C.) was used at this time. Because the intermediate product was not stable in the air, it was used in the next step immediately.

After reducing pressure for 4 hours, new anhydrous chloroform (2.5 mL) was added and the reaction was cooled to 0° C. again with an ice bath. Methanol (0.05 mL, 1.2821 mmol) was added slowly, and pyridine (0.103 mL, 1.2821 mmol) was added after that. The reaction was allowed to warm to room temperature for 24 hours. Then, water was added to halt the reaction and it was extracted with ethyl acetate. The organic solvent was removed by rotary evaporation to obtain 0.4 g (96%) of "3" from Scheme 2 as a yellow solid.

$^1$H NMR (300 MHz, CDCl3): δ=7.53-7.58 (d, J=15 Hz, 1H), 7.12 (s, 1H), 6.20-6.25 (d, J=15 Hz, 1H), 3.81 (s, 3H).
$^{13}$C NMR (300 MHz, CDCl3): δ=166.95, 136.83, 134.98, 127.60, 120.05, 116.24, 112.76, 51.89.

PBDTTh-TA:

To a 25 mL two-neck round bottom flask, "3" from Scheme 2 (54.1 mg, 0.1658 mmol), "4" from Scheme 2 (150 mg, 0.1658 mmol) and P(o-toly)$_3$ (4 mg, 0.0133 mmol) were added. After the reaction system was subjected to three cycles of purge and evacuation, anhydrous chlorobenzene (5 mL) was added to dissolve the mixture followed by adding Pd$_2$(dba)$_3$ (3 mg, 0.0033 mmol) as a catalyst. Then the reaction was stirred at 90° C. under Argon. After 24 hours, the mixture was cooled to room temperature. It was poured into methanol (100 mL) and was stirred for 1 hour. A deep red precipitate was collected after filtration. It was washed with acetone, hexane, chloroform in a Soxhlet extractor for 24 hours each to afford/yield 121 mg (98%) of PBDTTh-TA as a red solid in chloroform portion (Mn=27.4 k, Mw=47.6 k, PDI=1.74).

Methyl 2,5-dibromothiophene-3-carboxylate (6)

A solution of "5" from Scheme 2 (0.572 g, 2.0003 mmol) in anhydrous chloroform (4 mL) was put into an oven dried 3-neck round bottom flask under nitrogen, and then the solution was cooled to 0° C. by using an ice bath. Oxalyl chloride (0.19 mL, 2.2003 mmol) was added dropwise using a dropping funnel, followed with dimethylformamide (0.1 mL) as a catalyst. After the addition of oxalyl chloride, the reaction was allowed to warm to room temperature for 4 hours. Unreacted oxalyl chloride was removed under reduced pressure and a glass vacuum trap in a bath of mixture of acetone and dry ice (−78° C.) was used at this time. Because the intermediate product was not stable in the air, it was used in the next step immediately.

After reducing pressure for 4 hours, new anhydrous chloroform (4 mL) was added and the reaction was cooled to 0° C. again with an ice bath. Methanol (0.08 mL, 2.0003 mmol) was added slowly, and pyridine (0.16 mL, 2.0003 mmol) was added after that. The reaction was allowed to warm to room temperature for 24 hours. Then, water was added to halt the reaction and it was extracted with ethyl acetate. The organic solvent was removed, and the crude product was purified by column chromatography (silica gel, Hexane/dichloromethane mixture=1:1) to obtain "6" from Scheme 2 (0.136 g, 23%) as a white solid.

1H NMR (300 MHz, CDCl3): δ=7.35 (s, 1H), 3.87 (s, 3H).

PBDTTh-TC:

To a 25 mL two-neck round bottom flask, "6" from Scheme 2 (49.7 mg, 0.1658 mmol), "4" from Scheme 2 (150 mg, 0.1658 mmol) and P(o-toly)$_3$ (4 mg, 0.0133 mmol) were added. After the reaction system was subjected to three cycles of purge and evacuation, anhydrous chlorobenzene (5 mL) was added to dissolve the mixture followed by adding Pd$_2$(dba)$_3$ (3 mg, 0.0033 mmol) as a catalyst. Then the reaction was stirred at 90° C. under Argon. After 24 hours, the mixture was cooled to room temperature. It was poured into methanol (100 mL) and was stirred for 1 hour. A deep red precipitate was collected after filtration. It was washed with acetone, hexane, chloroform in a Soxhlet extractor for 24 hours each to afford/yield 118 mg (99%) of PBDTTh-TC as a red solid in chloroform portion (Mn=66.1 k; Mw=172.1 k; PDI=2.60).

Thermal Analysis:

High Temperature Gel Permeation Chromatography:

The high temperature gel permeation chromatography was measured by an Aligent PL-GPC220, using 1,2,4-trichlorobenzene solution at 110° C. with a concentration of 10 mg-ml$^{-1}$.

Characterization:

TGA measurements were carried out on TA Instruments SDT 2960 at a scan rate of 10° C. min$^{-1}$ under nitrogen. The UV-Vis absorption spectra of polymers were recorded on Cary 7000 Universal Measurement Spectrophotometer (UMS). UV data were obtained on a CHI600E electrochemical analyzer using an Ag/AgCl reference electrode and two Pt disk electrodes as the working and counter electrodes in a 0.1 M tetrabutylammonium hexafluorophosphate solution in acetonitrile at a scan rate of 100 mV s$^{-1}$. Ferrocene was used as the reference, which has a HOMO level value of −4.8 eV. NMR data was recorded with a Bruker DPX 300 MHz spectrometer with chemical shifts relative to tetramethylsilane (TMS, 0 ppm). AFM images were taken the solar cell device using Dimension 3100 scanning probe microscope. PL quenching experiment was done on Horiba PTI QuantaMaster™ 8000 Series Fluorometer, on thin films coated on glass substrates. HT-GPC result was determined by Aligent PL-GPC220 by using 1,2,4-trichlorobenzne solution at 110° C. with a concentration of 10 mg-ml$^{-1}$.

Fabrication and Characterization of OTFT Devices:

The hole mobility of the polymer was measured by the BGBC configuration for all OTFT devices. The OTFT devices fabrication was carried out as follows: First, the gold source and drain pairs were patterned on a heavily n-doped SiO$_2$/Si wafer with 300 nm thickness of SiO$_2$ by conventional photolithography and thermal deposition. Then, the small square wafers that contain a set of transistors were cut from the large wafer and were placed into an aluminum dish (or glass petri dish, in either case) with acetone and sonicated in an ultra-sonic bath for 20 min at room temperature. Subsequently, acetone was removed and 2-propanol (IPA) was added followed by ultrasonication for an additional 20 min After sonication, the wafers were dried by using nitrogen gas and treated with oxygen plasma for 2 min with low air flow. Wafers were immersed into pure ethanol, chloroform, 20 mL of a 10 mM solution of octadecanethiol in ethanol for 1 hour and pure ethanol in a covered petri dish successively. After that, wafers were immersed in 100 mL DI Water in covered petri dish, and four drops of 1:10:10 (HNO$_3$:HCl:H$_2$O) were added. The wafers were kept for one min. Wafers were removed and rinsed with deionized water. Wafers were dried with nitrogen gas and subsequently on hot plate at 120° C. for 10 min. In the next step, wafers were put in a solution of DDTS in toluene (3% DDTS in toluene) at room temperature for 20 min. The substrates were then rinsed with toluene to remove multilayers of DDTS and dried under a nitrogen flow. Then a polymer solution in chloroform (5 ml$^{-1}$ mg) was spin-coated onto the substrate at 1000 rpm for 60 seconds to obtain a polymer film, which was further subjected to thermal annealing at different temperatures for 20 min in an argon filled glove box. All the OTFT devices have a channel length (L) of 30 μm and a channel width (W) of 1000 μm and were characterized in the same glove box using an Agilent B2912A Semiconductor Analyzer. The hole and electron mobilities are calculated in the saturation regime according to the following equation:

$$I_{DS} = \frac{\mu C_i W}{2L}(V_G - V_T)^2$$

where $I_{DS}$ is the drain-source current, p is charge carrier mobility, $C_i$ is the gate dielectric layer capacitance per unit area (around 11.6 nF cm$^{-2}$), $V_G$ is the gate voltage, $V_T$ is the threshold voltage, L is the channel length (30 μm), and W is the channel width (1000 μm).

Fabrication and Characterization of Polymer Solar Cells:

Inverted polymer solar cells were fabricated in configuration ITO (150 nm), ZnO (35 nm)/Active layer/MoOx (10 nm)/Ag (100 nm). The glass ITO substrates were cleaned in an ultrasonic bath while immersed in deionized water and acetone for 20 min each at 40° C. The substrates were then taken out and cleaned by clean Q-tips dipped in acetone.

87

These substrates were then sonicated for 20 min at 40° C. in IPA. The substrates were dried with $N_2$ and placed into the air plasma cleaner for 10 min. A around 35 nm thin layer of ZnO was deposited by spin-coating a freshly prepared ZnO precursor solution (Zinc acetate (197 mg), Ethanolamine (54 µl), 2-methoxyethanol (2 ml) and stirring vigorously at 50° C. overnight,) at 3500 rpm and annealed subsequently at 200° C. for 1 h in air. Then the substrates were transferred to a nitrogen filled glove box, where the donor (PBDTTh-TA and PBDTM-TC) and acceptor ITIC blend (42 mg ml$^{-1}$ total for 1,2-DCB, 36 mg ml$^{-1}$ for CB and Xylene, 24 mg ml$^{-1}$ for CF respectively and in the ratio 1:1 (donor:acceptor)) layer was spin-coated onto the ZnO layer at various RPMs. Post annealing for 10 min (not for RT devices), the substrates were taken out and a thin layer of MoOx (10 nm) and 100 nm Ag electrode were deposited in vacuum onto the substrate at pressure less than $5.0 \times 10^{-6}$ Pa. The active area was 0.0574 cm$^2$. The current density-voltage (J-V) characteristics of the polymer solar cells were measured on an Agilent B2912A Semiconductor Analyzer with a ScienceTech SLB300-A Solar Simulator. A 450 W xenon lamp and an air mass (AM) 1.5 filter were used as the light source. EQE measurements were done in air (unencapsulated device) within 2-3 hours using QEX10 Solar Cell Quantum Efficiency Measurement System (PV measurements, Inc.).

Hole-Mobility Measurements:

The hole-mobilities were measured using the SCLC method in single carrier devices, employing a device architecture of ITO/PEDOT:PSS (30 nm)/active layer/MoO$_x$ (10 nm)/Ag (100 nm) while electron only mobilities were measured using a device ITO/ZnO (35 nm)/active layer/LiF (1 nm)/Al (100 nm).

The mobilities were obtained by taking current-voltage curves and fitting the results to a space charge limited form, where the SCLC is described:

$$J_{sclc} = \frac{9}{8}\mu\varepsilon \frac{V_{appl}^2}{d^3}$$

where $\varepsilon = \varepsilon_o \varepsilon_r$, $\varepsilon_o$ is the permittivity of free space, $\varepsilon_r$ is the relative permittivity of the material (assumed to be 3), µ is the hole mobility, $V_{appl} = V - V_{bi}$ is the applied voltage corrected for built in potential $V_{bi}$, and d is the thickness of the film.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

All cited patents, patent applications, and other references are incorporated herein by reference in their entirety.

Although the systems and methods of the present disclosure have been described with reference to exemplary embodiments thereof, the present disclosure is not limited to such exemplary embodiments and/or implementations. Rather, the systems and methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

What is claimed is:

1. A polymer semiconductor material is denoted by structure (PI):

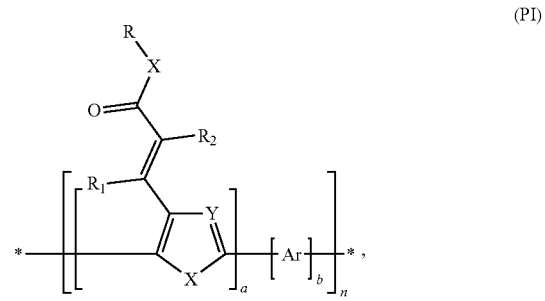

(PI)

wherein each X is independently selected from oxygen (O), sulphur (S), selenium (Se), or nitrogen (N);
R, and R$_1$ are independently selected from hydrogen, an optionally substituted hydrocarbon with 1 to 60 carbon (C) atoms, cyano (CN), nitro, or a halogen;
R2 is selected from hydrogen or a C1-C60 alkyl optionally substituted with an alkoxy, nitro, or a halogen;
Y is selected from N or —CR", wherein R" is H, an optionally substituted hydrocarbon with 1 to 60 carbon (C) atoms, cyano (CN), nitro, or a halogen;
a is an integer from 1 to 20;
each Ar is selected from the group

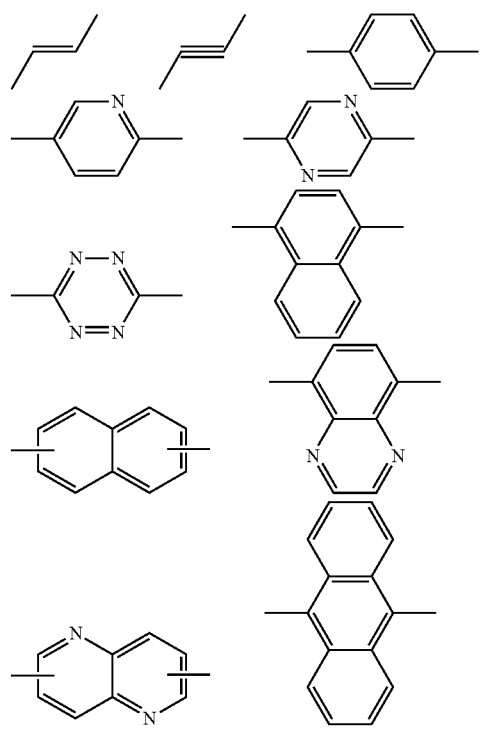

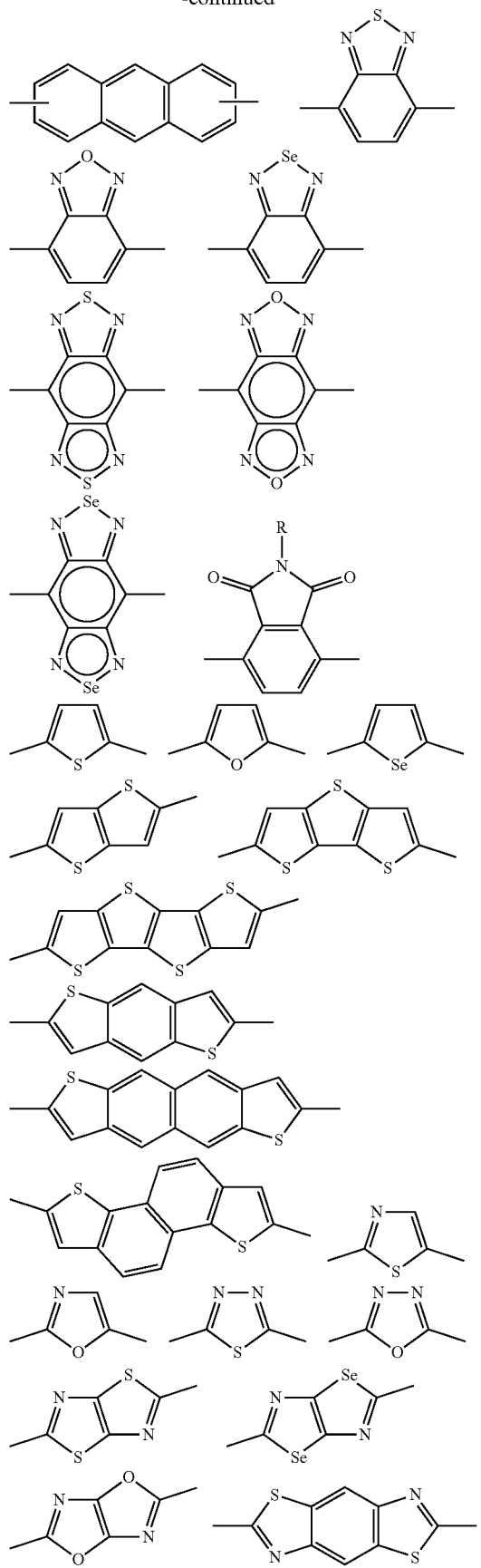
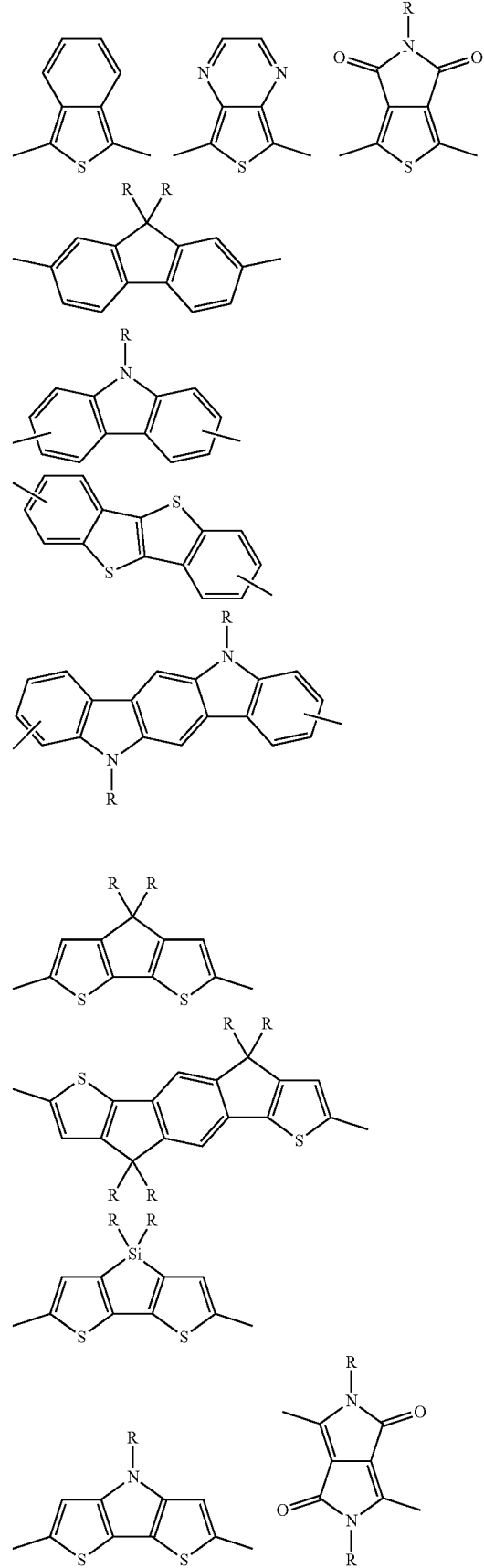

91
-continued
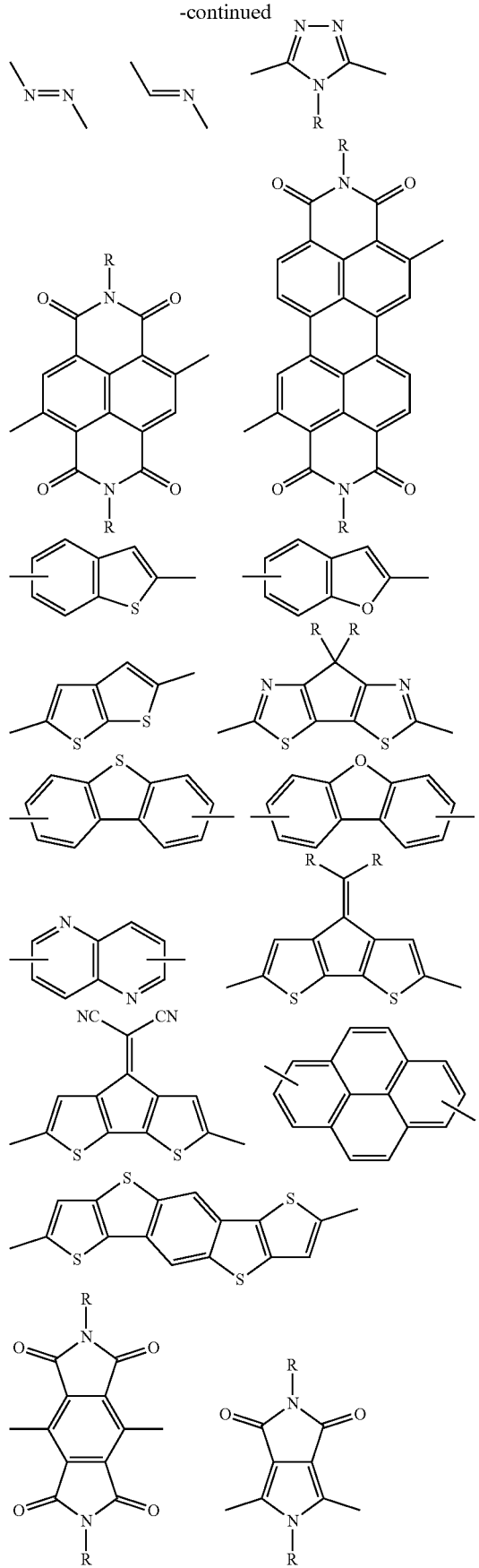
92
-continued
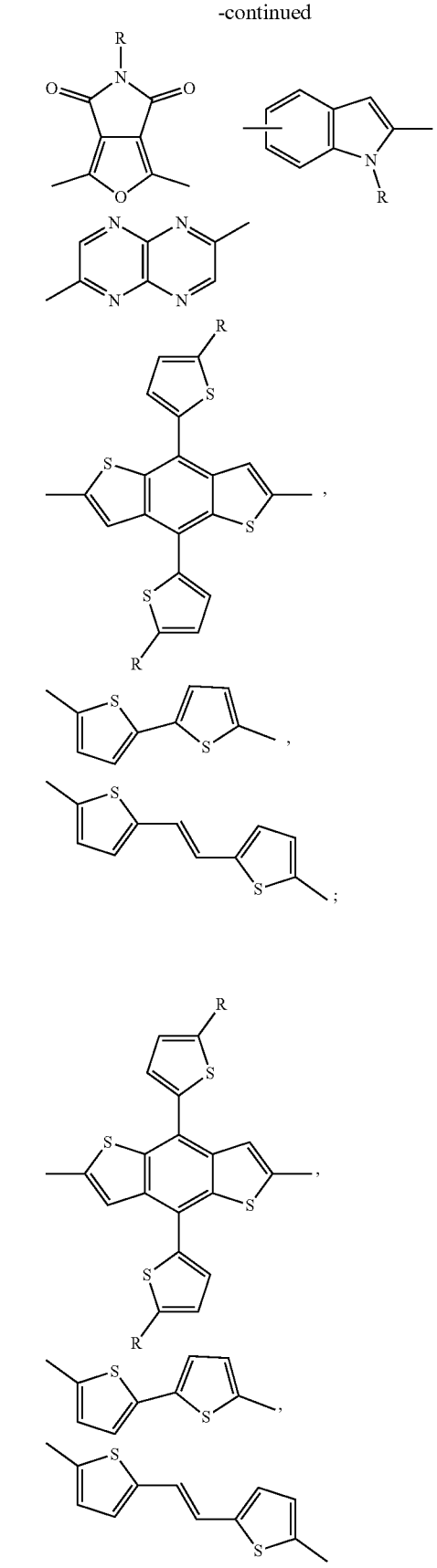

wherein R of Ar is hydrogen, an optionally substituted hydrocarbon with 1 to 60 carbon (C) atoms, cyano (CN), nitro, or a halogen, and wherein Ar can be substituted by a member of an optionally substituted hydrocarbon with 1 to 60 carbon (C) atoms, cyano (CN), nitro, or a halogen;

b is an integer from 1 to 20;

n is a number from about 1 to 1,000,000, and wherein * represents a bond to another PI unit or, if terminal, is hydrogen or a halogen group.

2. The material of claim 1, wherein structure (PI) is selected from the structures:

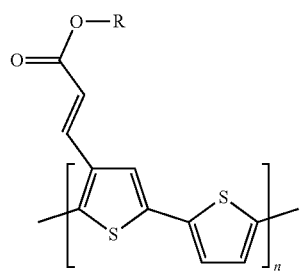
(1)

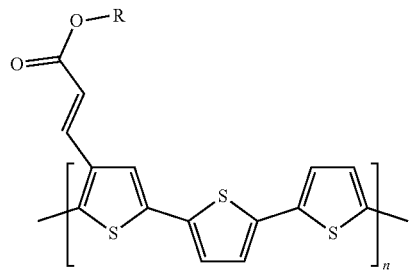
(2)

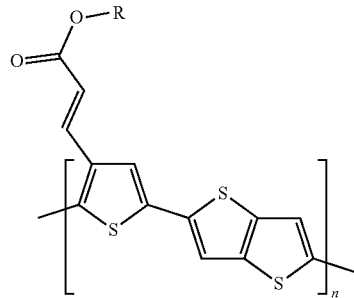
(3)

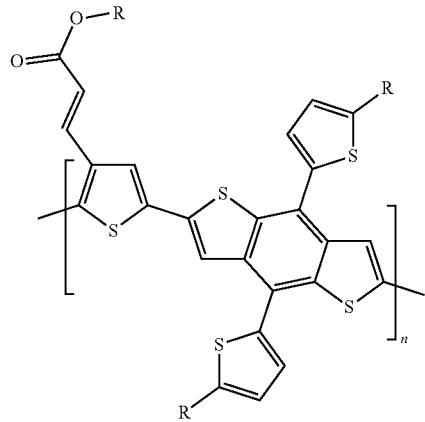
(5)

-continued

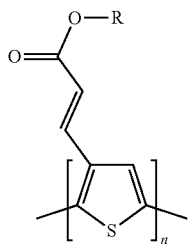
(6)

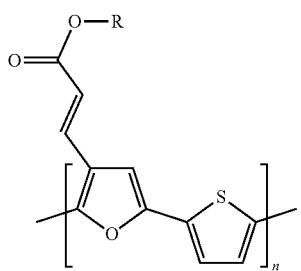
(7)

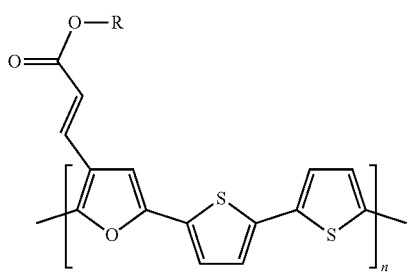
(8)

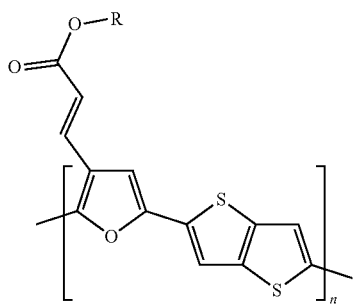
(9)

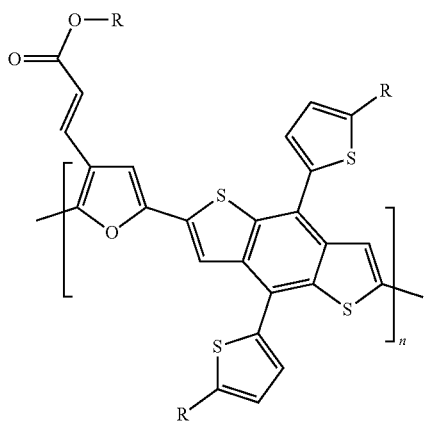
(11)

(12) 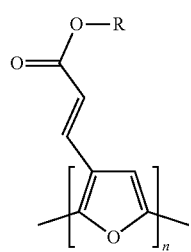
(13) 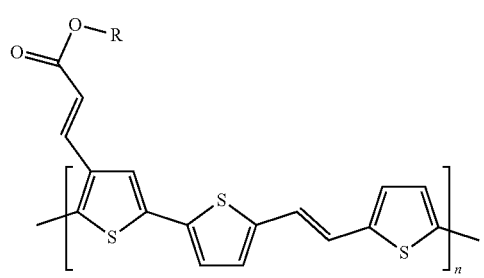
(14) 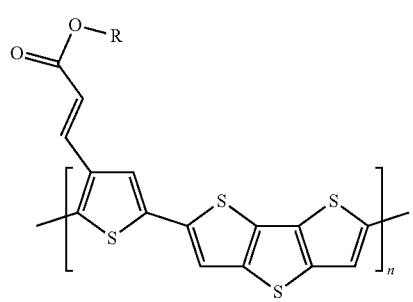
(15) 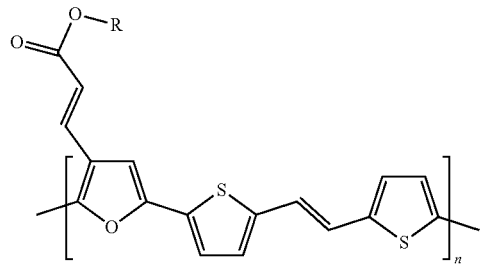
(16) 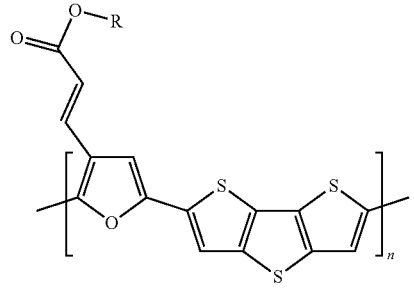
(17) 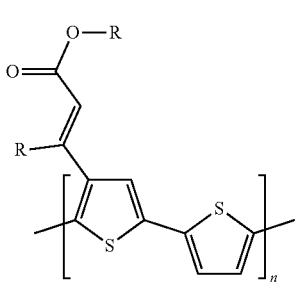
(18) 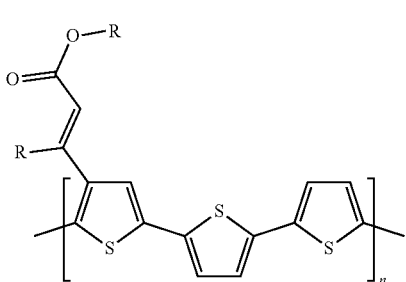
(19) 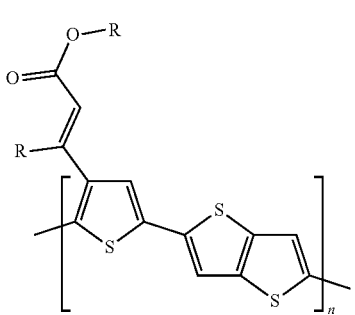
(21) 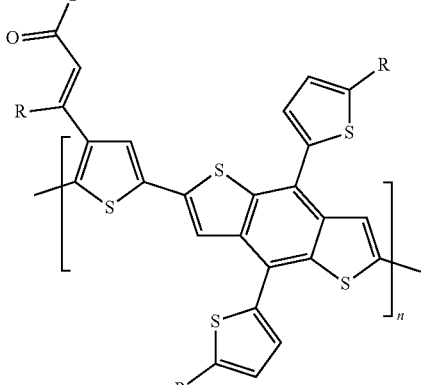
(22) 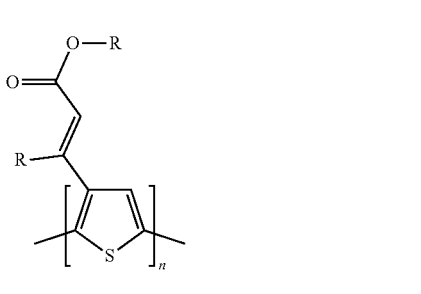

(23) 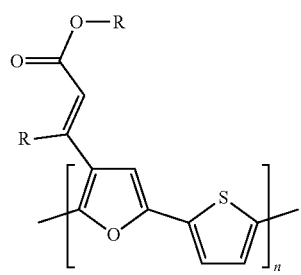
(24) 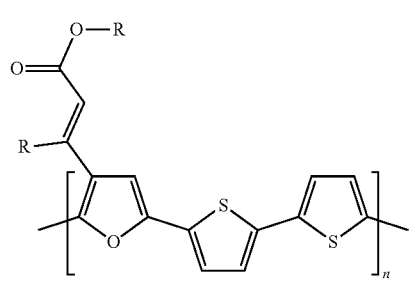
(25) 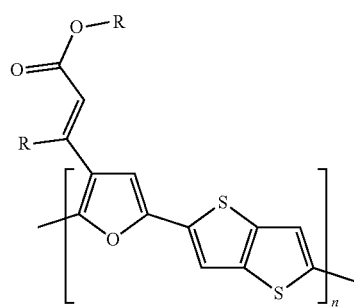
(27) 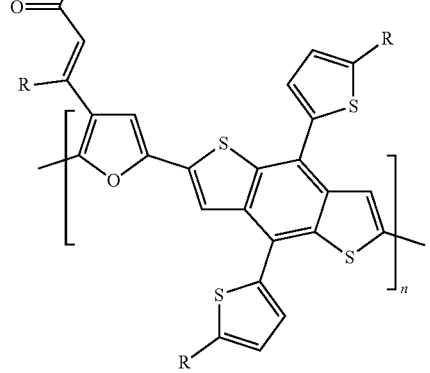
(28) 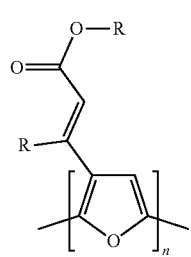
(29) 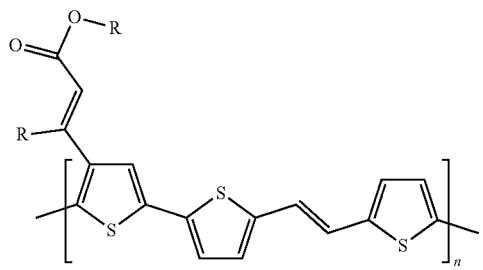
(30) 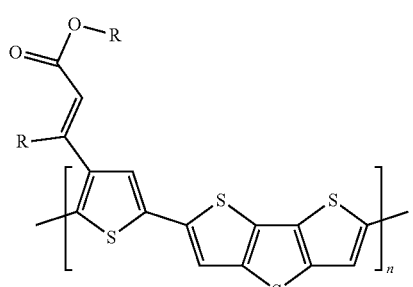
(31) 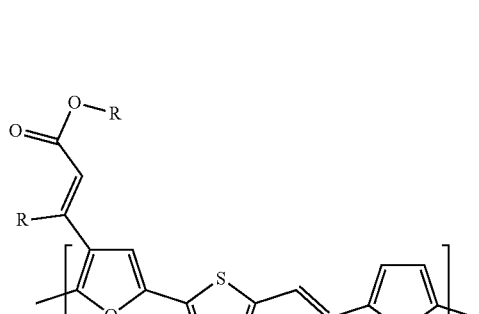
(32) 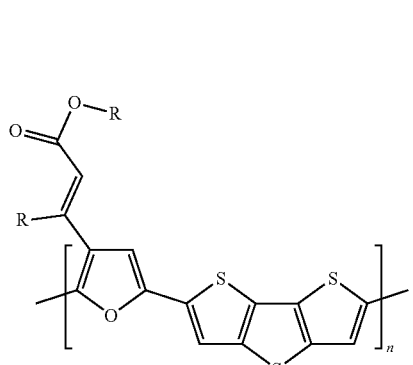
(33) 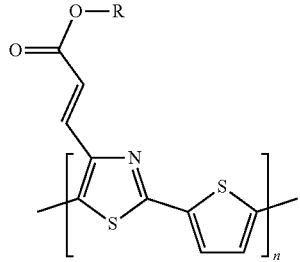

(34)
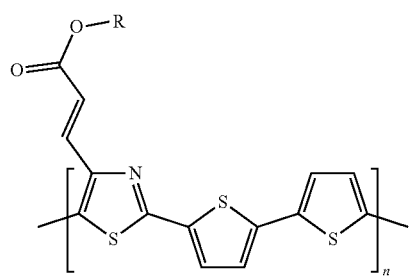
(35)
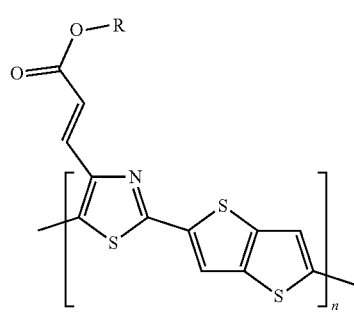
(37)
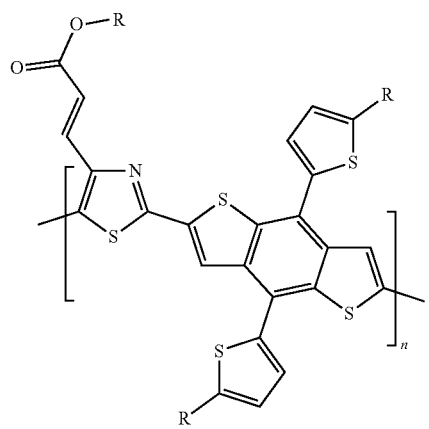
(38)
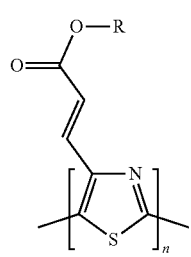
(39)
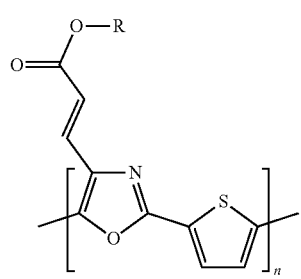
(40)
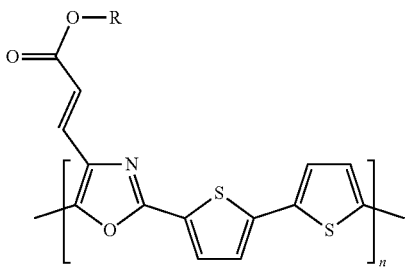
(41)
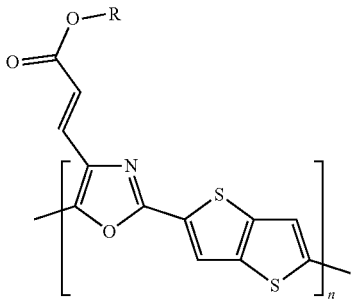
(43)
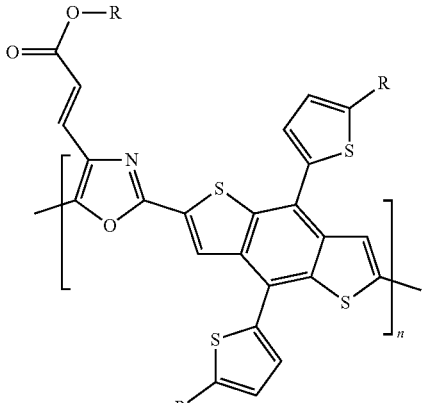
(44)
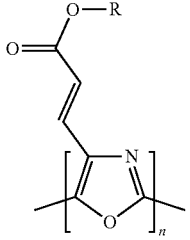
(45)
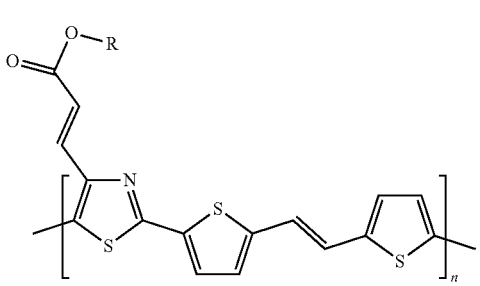

-continued
(46)
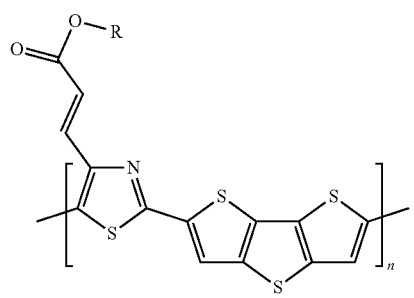
(47)
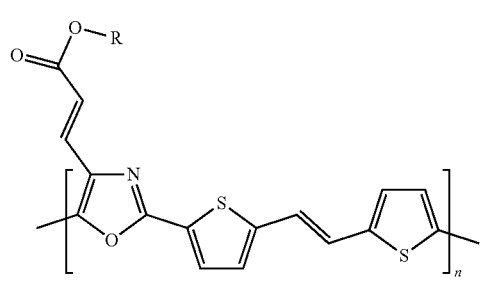
(48)
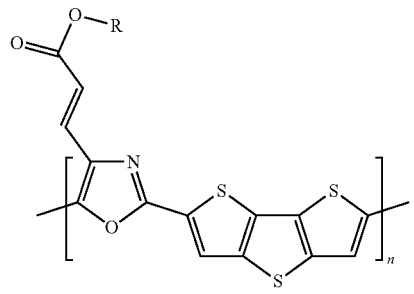
(49)
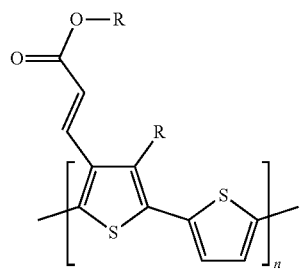
(50)
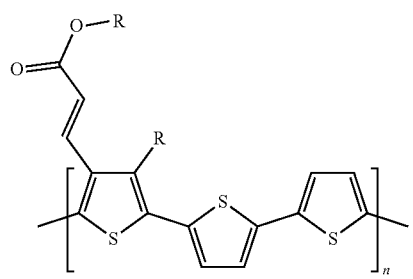
-continued
(51)
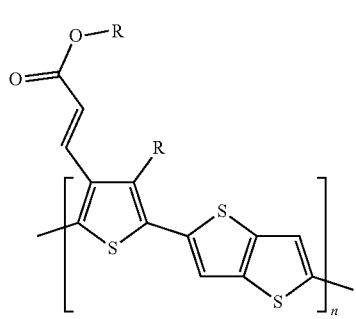
(53)
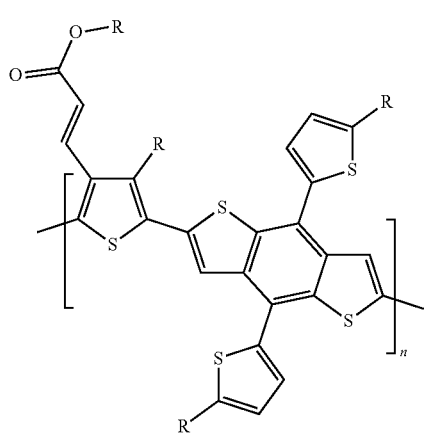
(54)
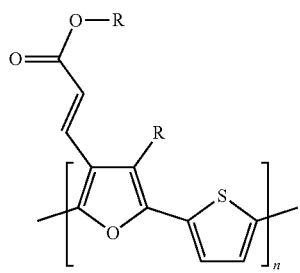
(55)
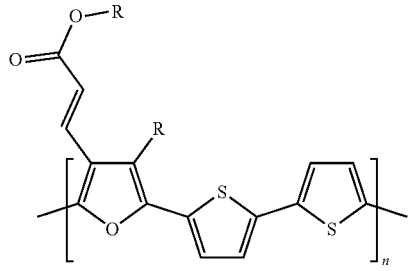
(56)
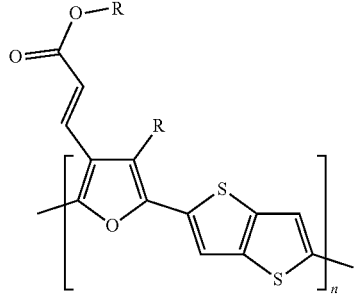

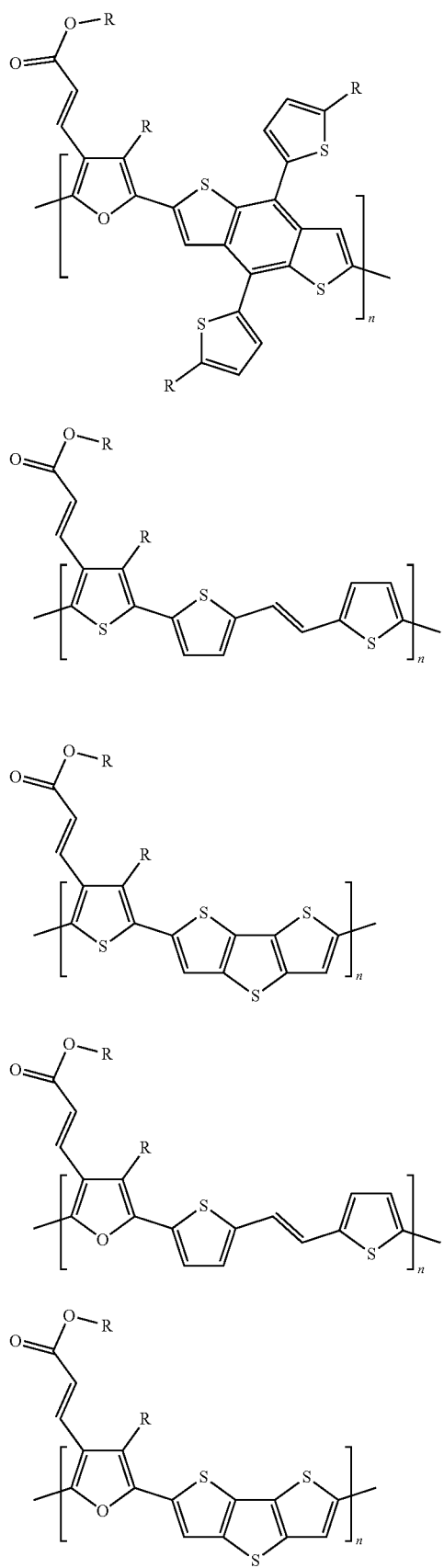
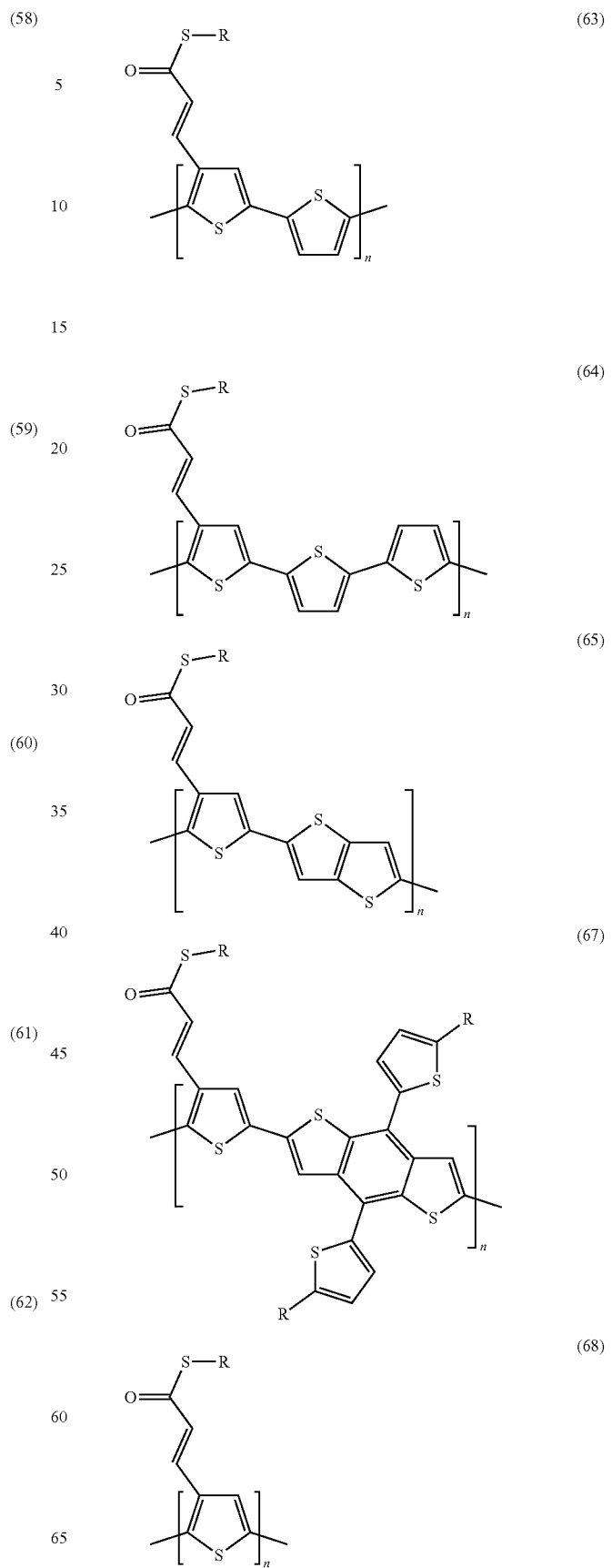

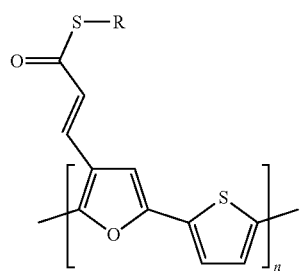
(69)
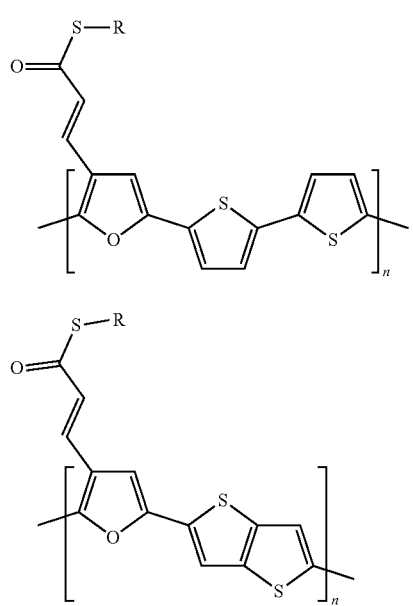
(70)
(71)
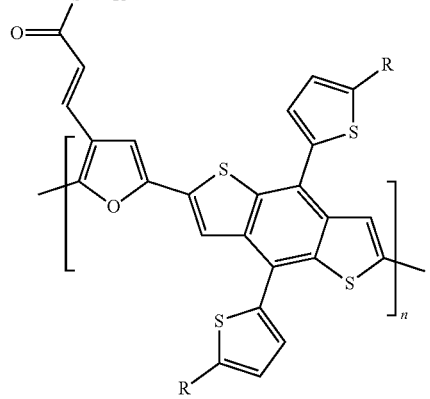
(73)
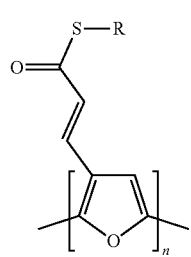
(74)
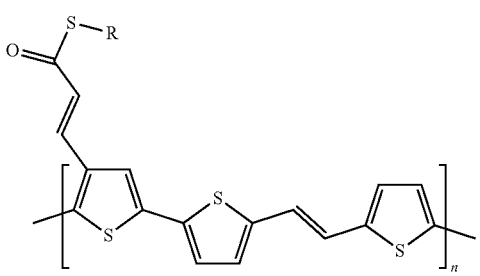
(75)
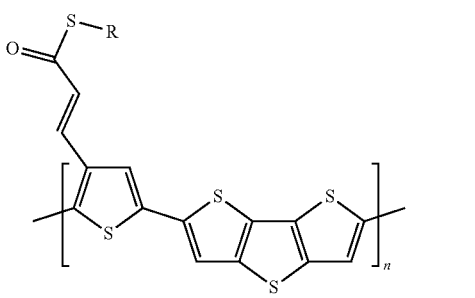
(76)
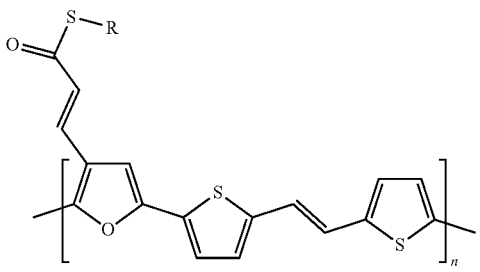
(77)
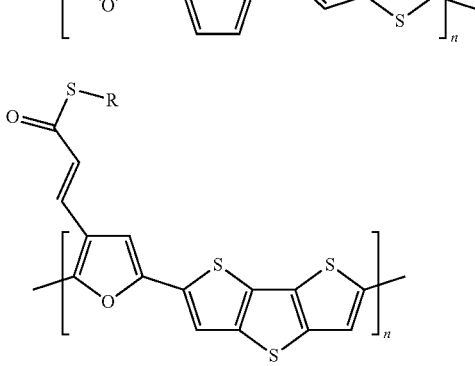
(78)
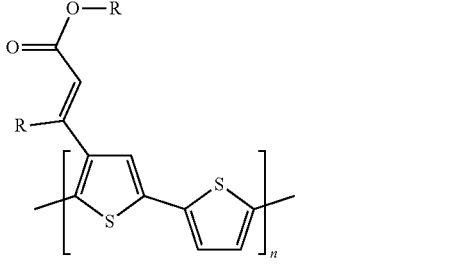
(79)

(80)
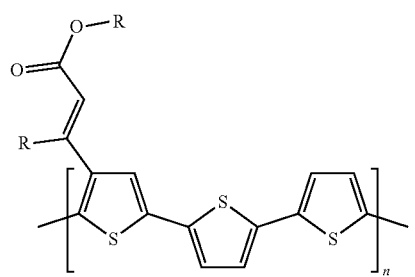
(81)
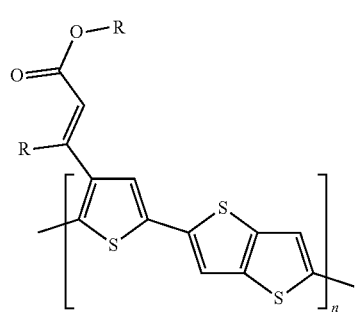
(83)
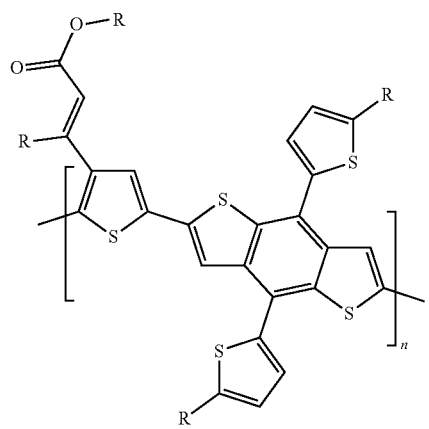
(84)
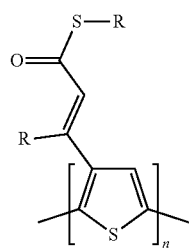
(85)
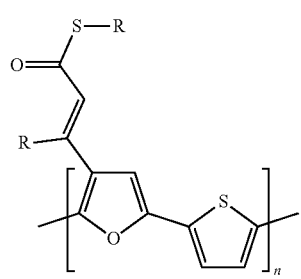
(86)
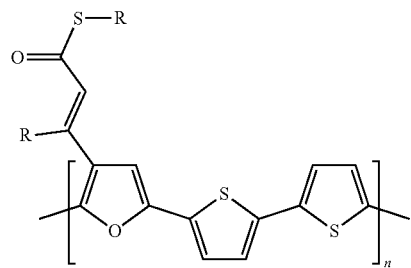
(87)
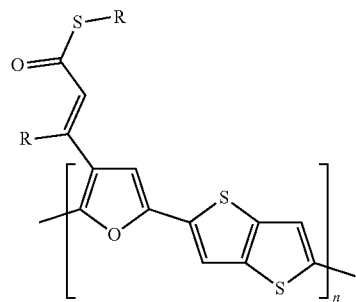
(89)
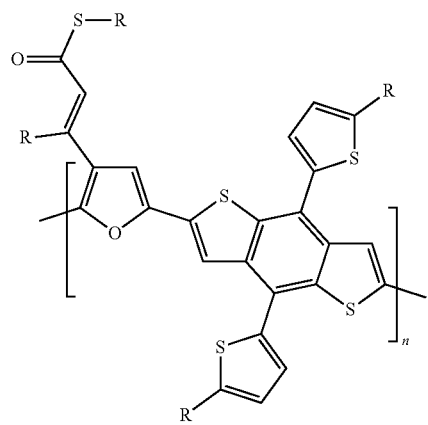
(90)
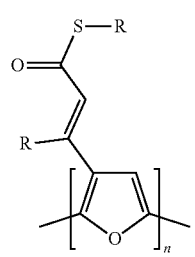
(91)
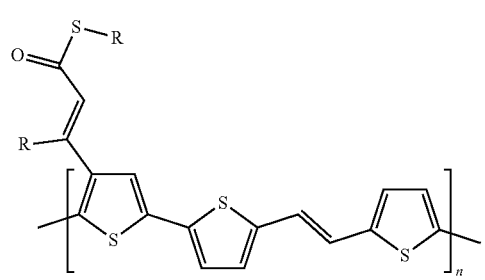

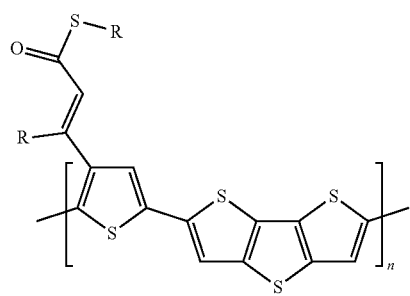
(92)
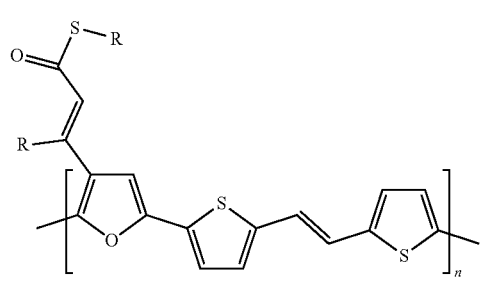
(93)
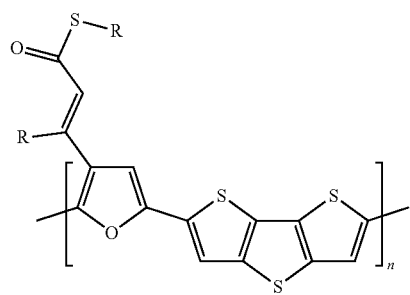
(94)
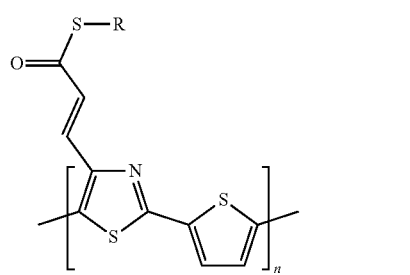
(95)
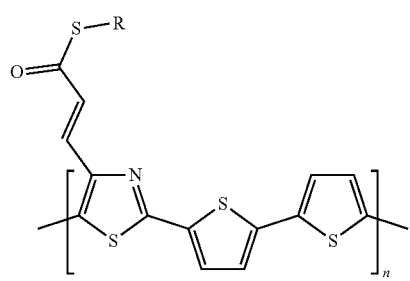
(96)
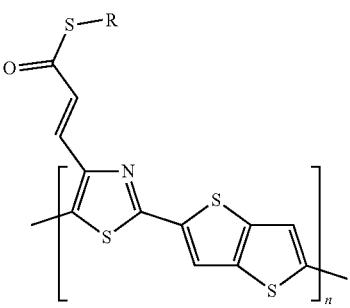
(97)
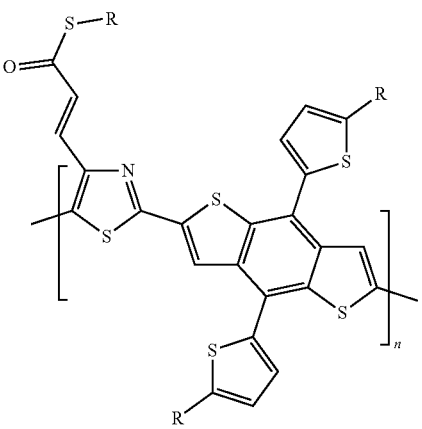
(99)
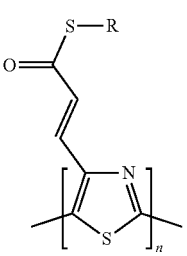
(100)
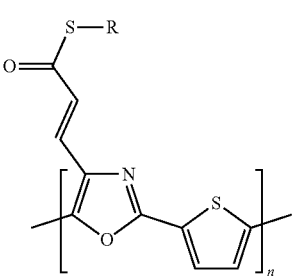
(101)
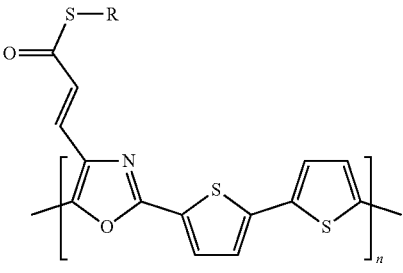
(102)

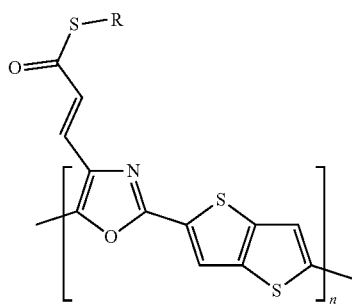
(103)
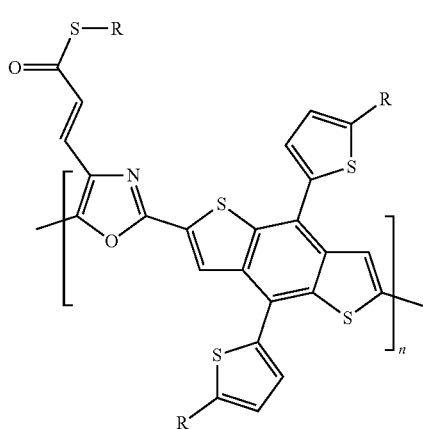
(105)
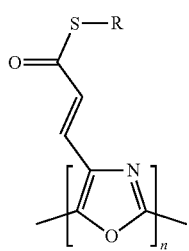
(106)
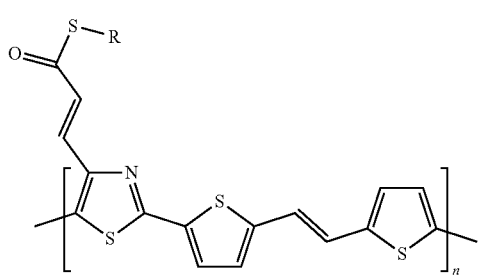
(107)
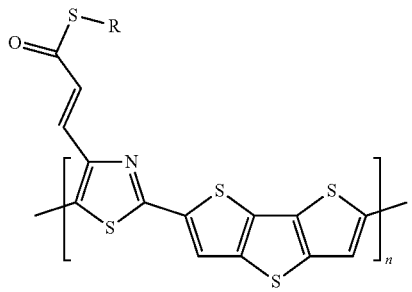
(108)
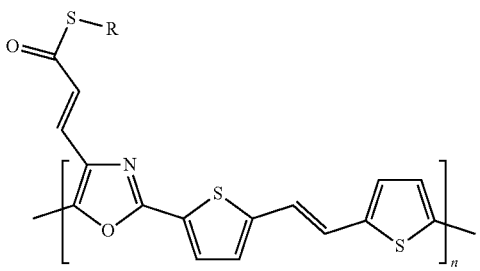
(109)
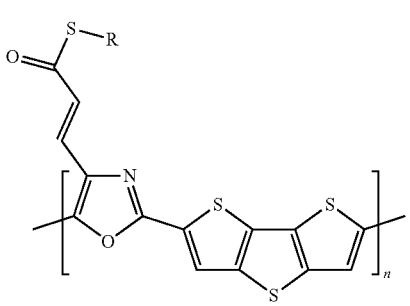
(110)
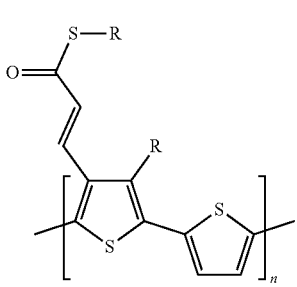
(111)
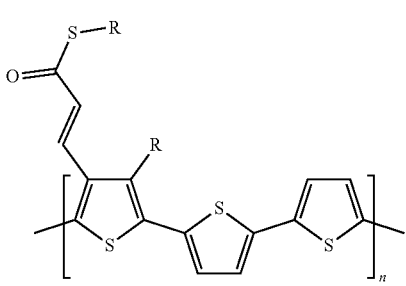
(112)
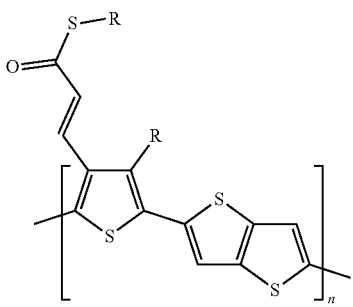
(113)

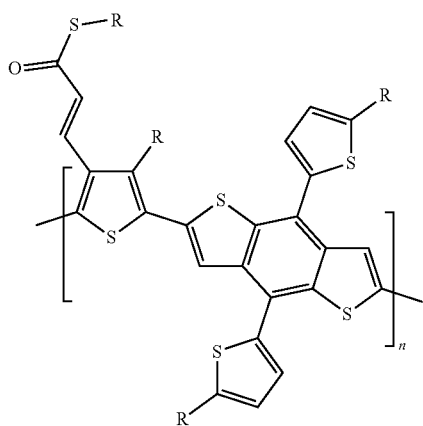
(115)
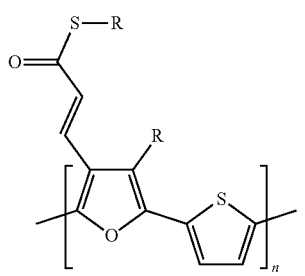
(116)
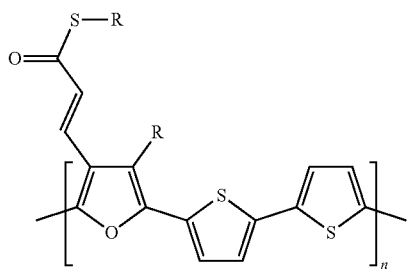
(117)
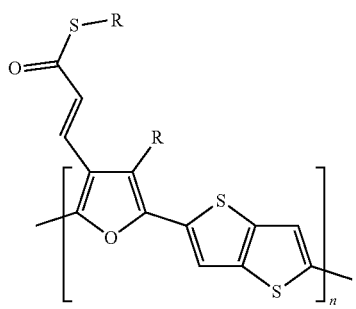
(118)
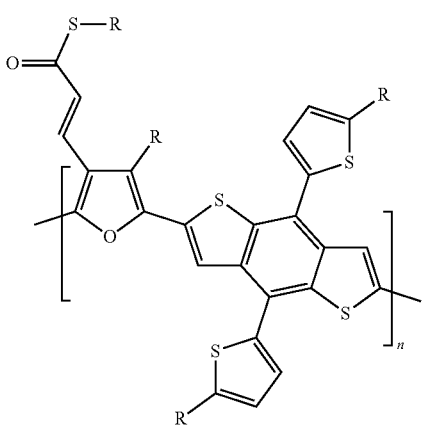
(120)
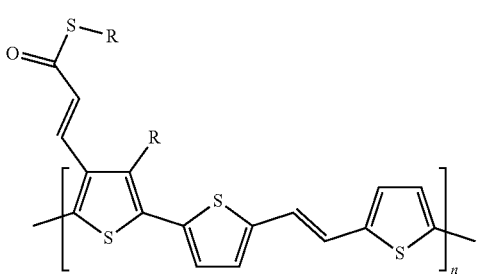
(121)
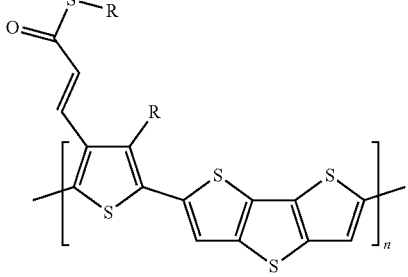
(122)
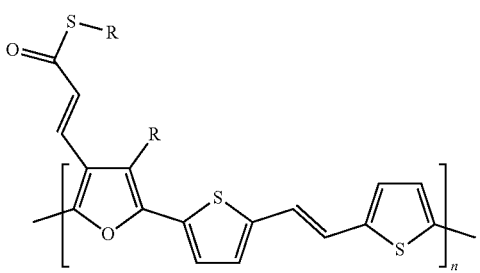
(123)
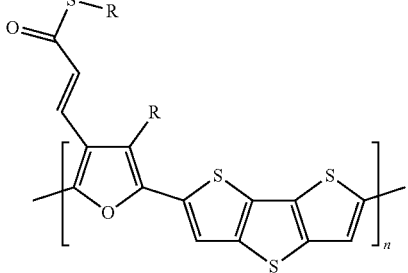
(124)

-continued
(125) 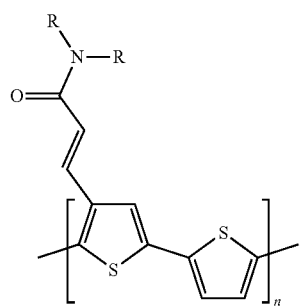
(126) 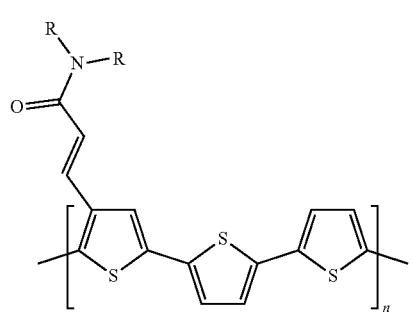
(127) 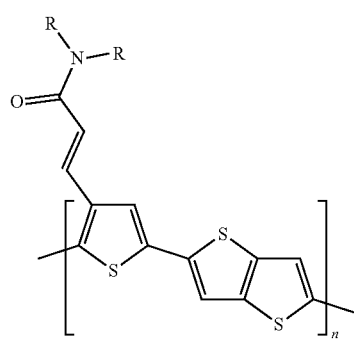
(129) 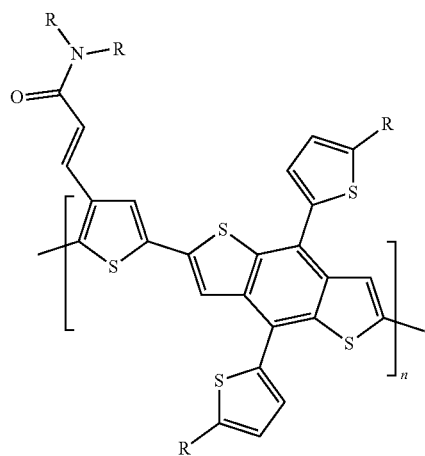
-continued
(130) 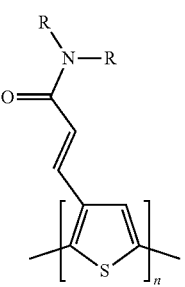
(131) 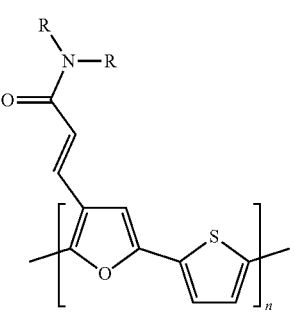
(132) 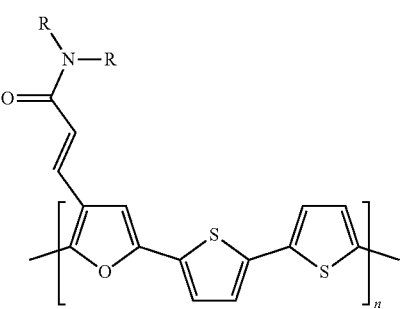
(133) 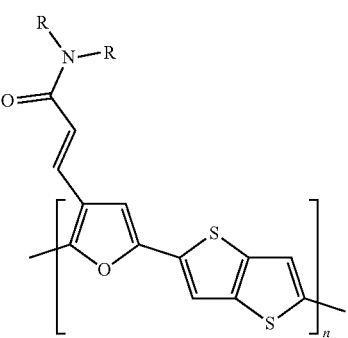

(135)
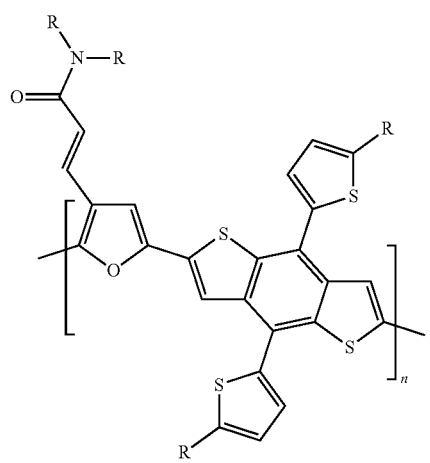
(136)
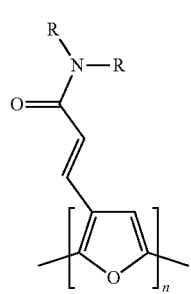
(137)
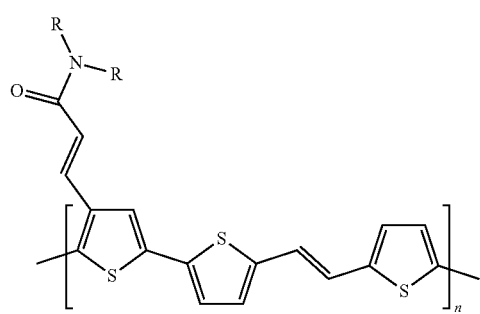
(138)
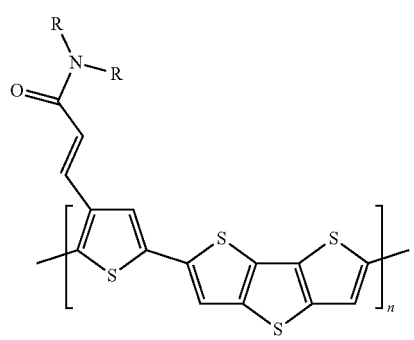
(139)
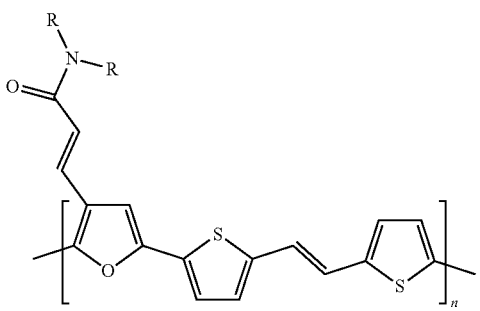
(140)
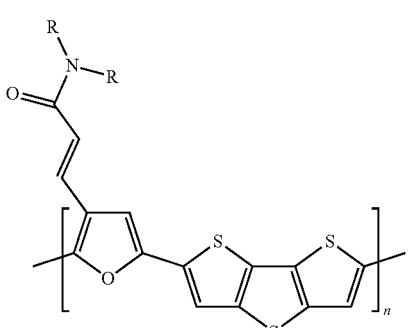
(141)
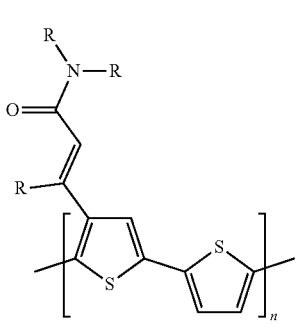
(142)
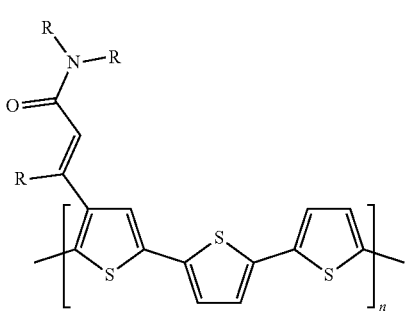
(143)
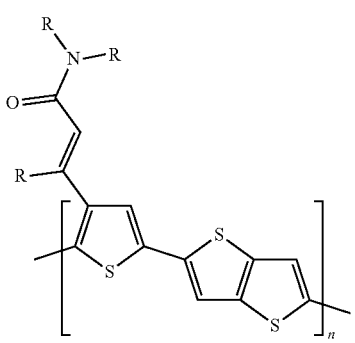

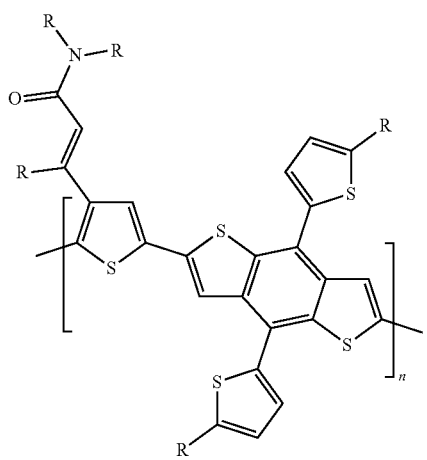
(145)
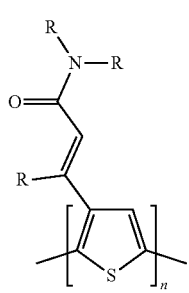
(146)
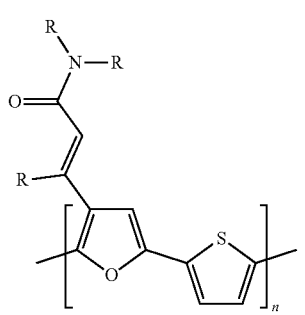
(147)
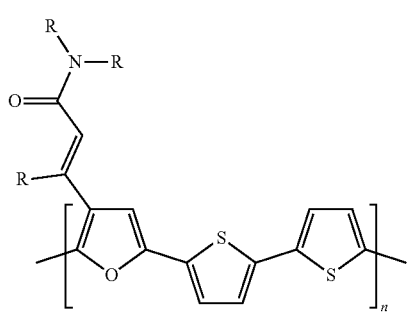
(148)
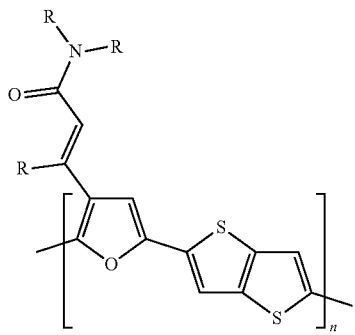
(149)
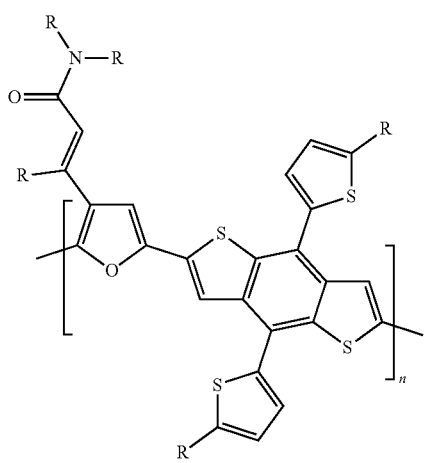
(151)
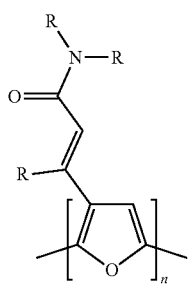
(152)
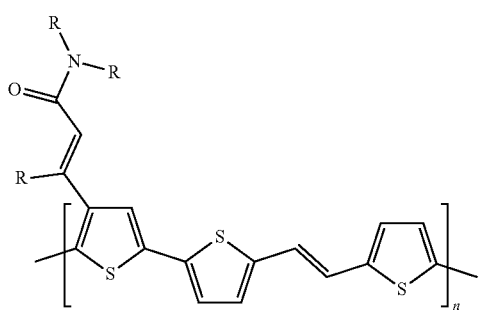
(153)

(154)
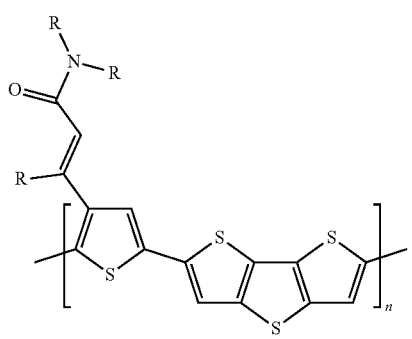
(155)
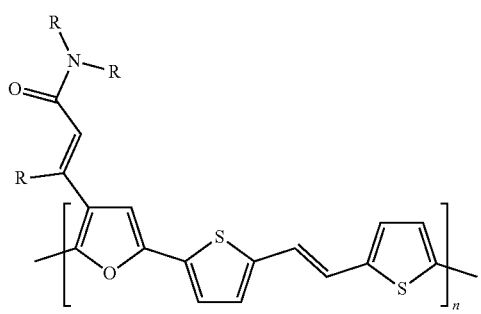
(156)
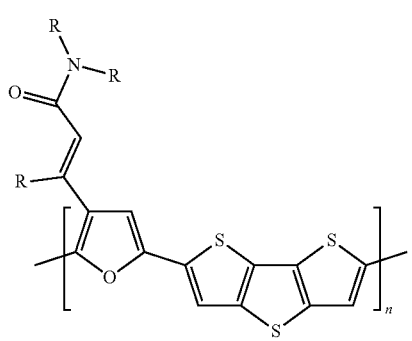
(157)
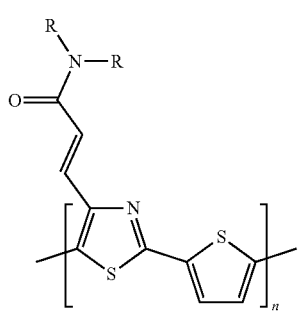
(158)
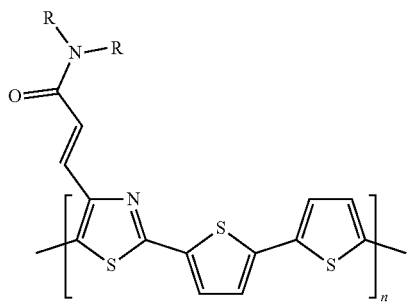
(159)
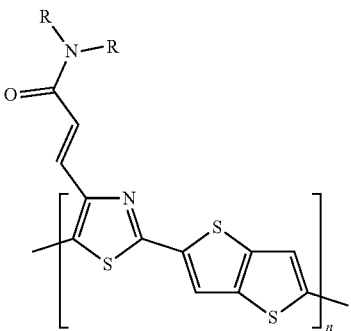
(161)
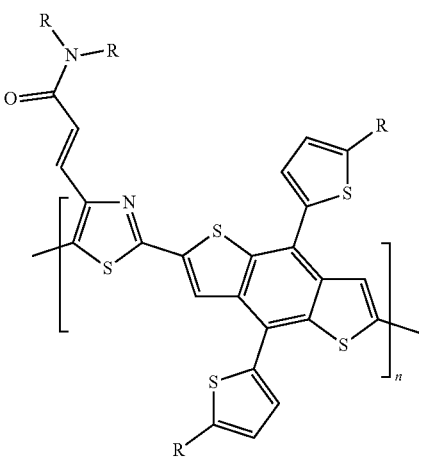
(162)
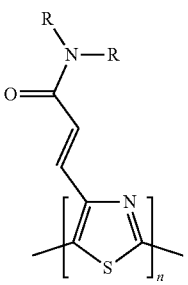
(163)
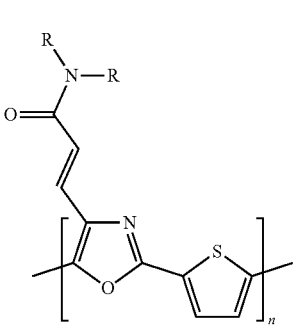

(164)
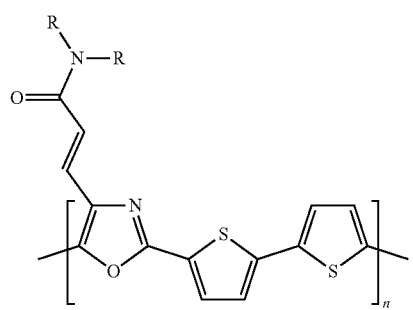
(165)
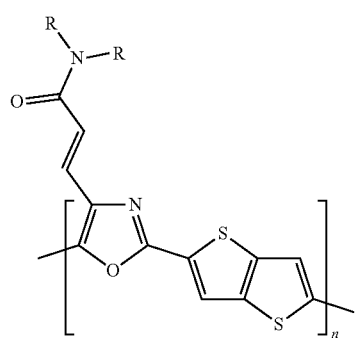
(167)
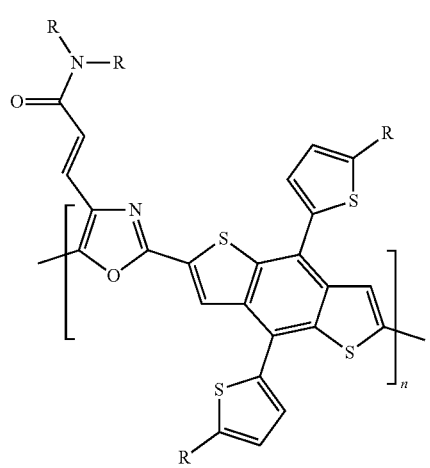
(168)
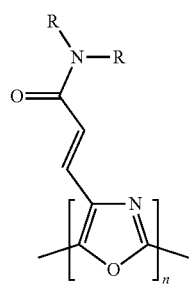
(169)
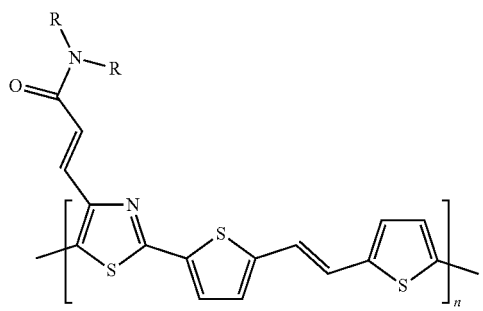
(170)
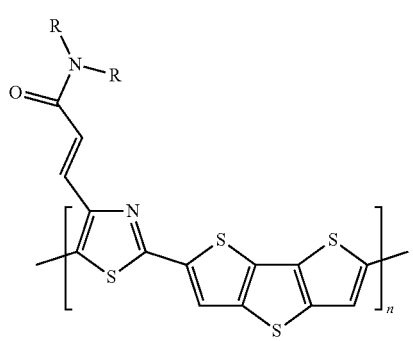
(171)
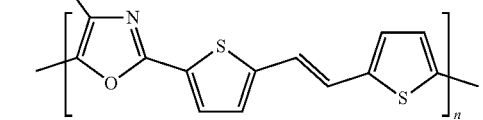
(172)
(173)
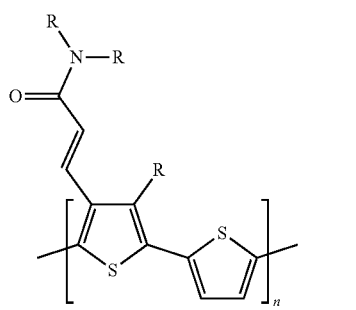

-continued
(174)
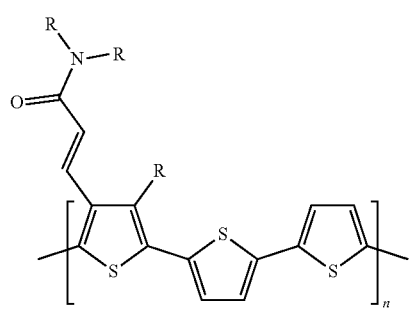
(175)
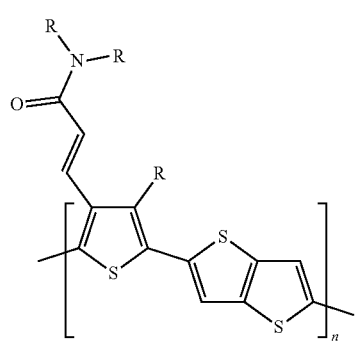
(177)
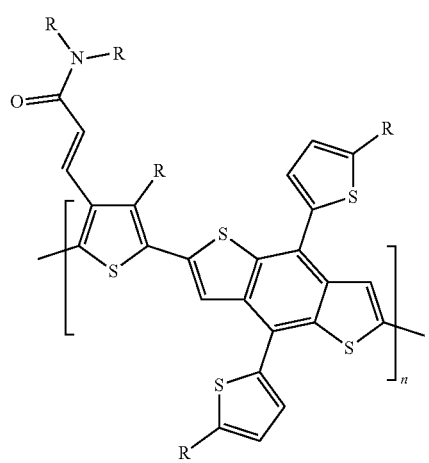
(178)
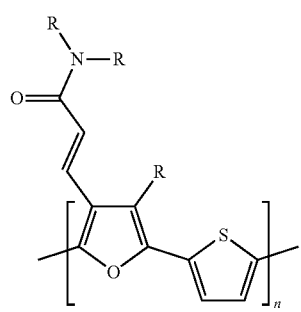
-continued
(179)
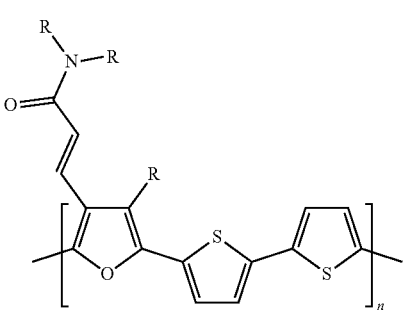
(180)
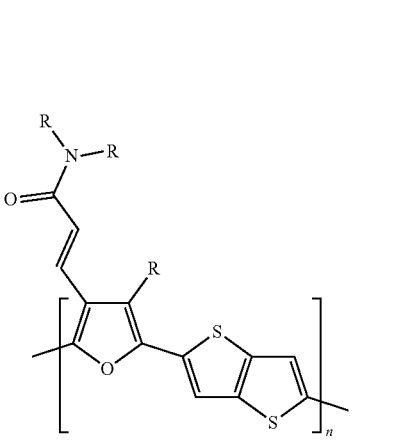
(182)
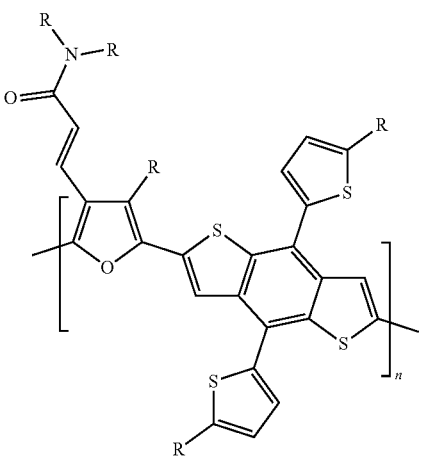
(183)
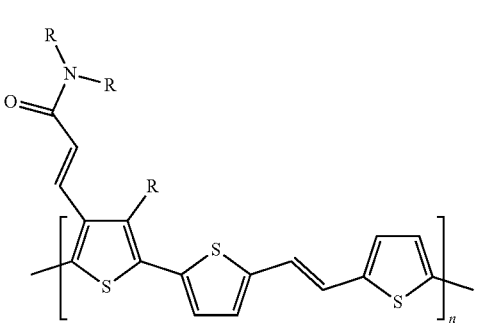

-continued (184)
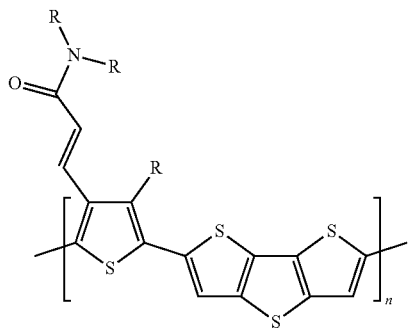

(185)
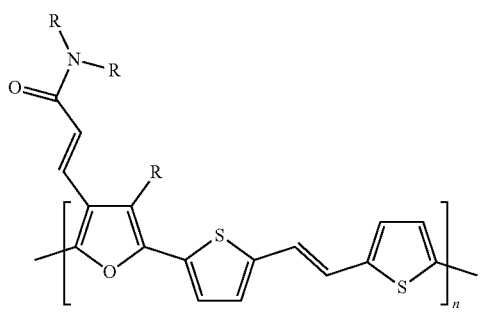

(186)
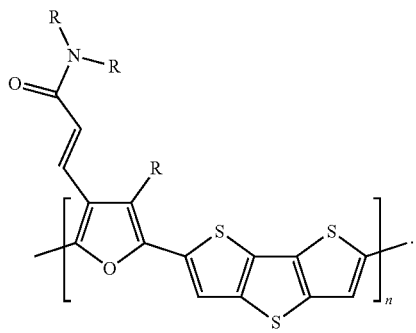

3. An electronic device comprising the material according to claim 1.

4. The electronic device according to claim 3, wherein the electronic device is selected from the group consisting of organic field effect transistors (OFET), organic thin film transistors (OTFT), integrated circuits (IC), logic circuits, capacitors, radio frequency identification (RFID) tags, devices or components, organic light emitting diodes (OLED), organic light emitting transistors (OLET), flat panel displays, backlights of displays, organic photovoltaic devices (OPV), organic solar cells (O-SC), photodiodes, laser diodes, photoconductors, organic photodetectors (OPD), electrophotographic devices, electrophotographic recording devices, organic memory devices, sensor devices, charge injection layers, charge transport layers or interlayers in polymer light emitting diodes (PLEDs), Schottky diodes, planarizing layers, antistatic films, polymer electrolyte membranes (PEM), conducting substrates, conducting patterns, electrode materials in batteries, alignment layers, biosensors, biochips, security markings, security devices, and components or devices for detecting and discriminating DNA sequences.

5. The electronic device according to claim 3, wherein the electronic device is an organic thin film transistor.

6. The electronic device according to claim 3, wherein the electronic device is an organic photovoltaic cell or organic photodiode.

7. An electronic device comprising the material according to claim 1.

8. The electronic device according to claim 7, wherein the electronic device is an organic thin film transistor.

9. The electronic device according to claim 6, wherein the electronic device is an organic photovoltaic cell or organic photodiode.

10. An electronic device comprising the material according to claim 2.

11. The electronic device according to claim 10, wherein the electronic device is an organic thin film transistor.

12. The electronic device according to claim 10, wherein the electronic device is an organic photovoltaic cell or organic photodiode.

13. A semiconductor layer comprising the material according to claim 2.

* * * * *